US008535883B2

(12) United States Patent
Cane et al.

(10) Patent No.: US 8,535,883 B2
(45) Date of Patent: Sep. 17, 2013

(54) METHODS OF DETECTING SOURCES OF MICROORGANISM CONTAMINATION

(75) Inventors: David Cane, Providence, RI (US);
Steven Giglio, West Croydon (AU);
Jiaoyang Jiang, Boston, MA (US);
Christopher P. Saint, Largs Bay (AU);
Paul T. Monis, Adelaide (AU)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 13/048,407

(22) Filed: Mar. 15, 2011

(65) Prior Publication Data
US 2011/0250604 A1    Oct. 13, 2011

Related U.S. Application Data

(63) Continuation of application No. PCT/US2009/057266, filed on Sep. 17, 2009.

(60) Provisional application No. 61/192,309, filed on Sep. 17, 2008.

(51) Int. Cl.
*C12Q 1/68* (2006.01)

(52) U.S. Cl.
USPC .......................................... 435/6.1

(58) Field of Classification Search
None
See application file for complete search history.

(56) References Cited

FOREIGN PATENT DOCUMENTS
WO    WO 2010/033670    3/2010

OTHER PUBLICATIONS

Ludwig et al. Appl Environ Microbiol. Nov. 2007;73(21):6988-93. Epub Sep. 7, 2007).*
Cane et al. (Appl Environ Microbiol. Sep. 2006;72(9):5857-63).*
Agger, S. A., et al., "Identification of sesquiterpene synthases from *Nostoc punctiforme* PCC 73102 and *Nostoc* sp. strain PCC 7120," *J. Bacteriol.* 190, 6084-6096 (2008).
Arnold, C., et al., "Vectorette PCR: A Novel Approach to Genomic Walking," PCR Methods App., 1:39-42 (1991).
Bentley, R. and Meganathan, R., "Goesmin and Methylisoborneol Biosynthesis in Streptomyces. Evidence for an Isoprenoid Pathway and Its Absence in Non-Differentiating Isolates," FEBS Lett. 125:220-222.
Cane D.E., and Watt, R.M., "Expression and Mechanistic Analysis of a Germacradienol Synthase from *Streptomyces coelicolor* Implicated in Geosmin Biosynthesis," Proc. Natl Acad. Sci USA, 100:1547-51, (2003).
Cane, D.E., et al., "Geosmin Biosynthesis in *Streptomyces avermitilis*. Molecular Cloning, Expression, and Mechanistic Study of the Germacradioneol/Geosmin Synthase," Journal of Antibiotics, 59(8):471-479 (Aug. 2006).
Gerber, N. N., "Giosmin, An Earthly-Smelling Substance Isolated from Actinomycetes," Appl. Microbiol., 13:935-8 (1965).

Giglio, S., et al., "Isolation and Characterization of the Gene Associated with Geosmin Production in Cyanobacteria," *Env. Sci. Technol.* 42, 8027-8032 (2008).
Giglio, S., et al., "Legionella Confirmation Using Realtime PCR and SYT09 is an Alternative to Current Methodology," Appl. Environ. Microbiol., 71:8944-8 (2005).
Gust, B., et al., "PCR-Targeted *Streptomyces* Gene Replacement Identifies a Protein Domain Needed for Biosynthesis of the Sesquiterpene Soil Odor Geosmin," PNAS, 100(4):1541-1546 (Feb. 2003).
He, X., et al., "Mechanism and Stereochemistry of the Germacradienol/Germacrene D Synthase of *Streptomyces coelicolor* A3(2)" *J. Am. Chem. Soc.* 126, 2678-2679 (2004).
Ho, L., et al., "Biodegradation Rates of 2-Methylisoborneol (MIB) and Geosmin Through Sand Filters and in Bioreactors," Chemosphere, 66:2210-8 (2007).
International Preliminary Report on Patentability from PCT/US2009/057266, date of issuance Mar. 31, 2011.
International Search Report for PCT/US2009/057266 Dated Feb. 17, 2010.
Izaguirre, G., et al., "Geosmin and 2-Methylisoborneol from Cyanobacteria in Three Water Supply Systems," Appl. Environ. Microbiol., 43:708-714 (1982).
Jiang, J., et al., "Biosynthesis of the Earthy Oderant Geosmin by a Bifunctinal *Streptomyces coelicolor* Enzyme," Nature Chemical Biology, 3(11):711-715 (Nov. 2007).
Jiang, J., et al., "Geosmin Biosynthesis. Mechanism of the Fragmentation-Rearrangement in the Conversion of Germacradienol to Geosmin," J. Am. Chem. Soc., 130:428-9 (2008).
Jiang, J., et al., "Geosmin Biosynthesis. *Streptomyces coelicolor* Germacradienol/Germacrene D Synthase Converts Farnesyl Diphosphate to Geosmin," J. Am. Chem. Soc., 128:8128-9 (2006).
Keegan, A. R., et al., "Cell Culture-Taqman PCR Assay for Evaluation of *Cryptosporidium parvum* Disinfection," Appl. Environ. Microbiol., 69:2505-11 (2003).
Komatsu, M., et al., "Identification and Functional Analysis of Genes Controlling Biosynthesis of 2-Methylisoborneol," PNAS, 105(21):7422-7427 (May 2008).
Lloyd, S. W., et al., "Analysis of 2-methylisobomeol and Geosmin in Catfish by Microwave Distillation—Solid-Phase Microextraction," J. Agric. Food Chem., 47:164-9 (1999).
Ludwig, Frank, et al., "Identification and Expression Analyses of Putative Sesquiterpene Synthase Genes in *Phormidium* sp. and Prevalence of goA-Like Genes in a Drinking Water Reservoir," Applied and Environmental Microbiology, 73(21):6988-6993 (Nov. 2007).
Naes, H., et al., "Effect of Photon Fluence Rate and Specific Growth Rate on Geosmin Production of the Cyanobacterium *Oscillatoria* Brevis (Kutz.) Gom," Appl. Environ. Microbiol., 49:1538-1540 (1985).
Nawrath, T., et al., "Identification of (8S,9S,10S)-8,10-dimethyl-1-octalin, a key intermediate in the biosynthesis of geosmin in bacteria," *J. Am. Chem. Soc.* 130, 430-431 (2008).

(Continued)

*Primary Examiner* — Christopher M. Babic
(74) *Attorney, Agent, or Firm* — Hamilton, Brook, Smith & Reynolds, P.C.

(57) ABSTRACT

Methods of detecting a source of a microbial contamination in a suspect sample include detecting at least one member selected from the group consisting of a microbial geosmin synthase, a microbial 2-methylisoborneol synthase and a microbial 2-methylgeranyl diphosphate synthase in the suspect sample. The method can include conducting a nucleic acid amplification assay in the presence of at least one member selected from the group consisting of at least one microbial geosmin primer and at least one microbial 2-methylisoborneol synthase primer on a sample obtained from a suspect source of the microbial contamination.

10 Claims, 19 Drawing Sheets

(56) References Cited

OTHER PUBLICATIONS

Rasmussen, J. P., et al., "Development and Field Testing of a Real-Time PCR Assay for Cylindrospermopsin-Producing Cyanobacteria," J. Appl. Microbiol. (2007).

Robinson, B.S, et al., "Rapid, Sensitive and Discriminating Identification of *Naegleria* spp. By Real-Time PCR and Melting-Curve Analysis," Applied and Environmental Microbiology, 72(9):5857-5863 (Sep. 2006).

Schrader, K. K., et al., "Novel Derivatives of 9,10-Anthraquinone arc Selective Algicidcs Against the Musty-Odor Cyanobacterium Oscillatoria Peromata," Appl. Environ. Microbiol., 69:5319-27 (2003).

Wang, C-M., et al., "Biochemistry and Molecular Genetics of the Biosynthesis of the Earthy Oderant Methylisoborneol in *Streptomyces coelicolor*," Journal of the American Chemical Society, 130(28):8908-8909 (Jul. 2008).

Cook, D., et al., "The Application of Powdered Activated Carbon for MIB and Geosmin Removal: Predicting PAC Doses in Four Raw Waters, " Water Res., 35:1325-33 (2001).

Dickschat, J.S., et al., "A Novel Type of Geosmin Biosynthesis in Myxobacteria," J. Org. Chem., 70:5174-82 (2005).

Dickschat, J.S., et al., "Biosynthesis of the Off-Flavor 2 Methylisoborneol by the Myxobacterium Nannocystis Exedens," Angew Chem. Int. Ed. Engl., 46:8287-90 (2007).

Dorgan, K.M., et al., "An Enzyme-Coupled Continuous Spectrophotometric Assay for S-Adenosylmethionine-Dependent Methyltransferases, " Anal Biochem., 350:249-55 (2006).

Gagne, F., et al., "Toxicological Effects of Geosmin and 2-Methylisoborneol on Rainbow Trout Hepatocytes," Bulletin of Environmental Contamination and Toxicology, 63:174-180 (1999).

Gerber, N. N., "Volatile Substances from Actinomycetes: Their Role in the Odor Pollution of Water," CRC Crit. Rev. Microbiol., 7:191-214 (1979).

Hayes, K., et al., "Odorous Compounds Associate with Algal Blooms in South Australian Waters, "Wat. Res., 23:115-121 (1989).

Hayes, S. J., et al., "Geosmin as an Odorous Metabolite in Cultures of a Free-Living Amoeba, Vannella Species (Gymnamoebia, Vannellidae)," J. Protozool, 38:44-47 (1991).

Lahser, F.C., et al., "A Continuous Nonradioactive Assay for RNA-Dependent RNA Polymerase Activity," Anal. Biochem., 325:247-54 (2004).

Martin, J.F., et al., "A Planktonic Oscillatoria Species from Mississippi Catfish Ponds that Produces the Off-Flavour Compound 2—Methylisoborneol," Water Res., 25:1447-1451 (1991).

Naes, H., et al.., "Transient States of Geosmin, Pigments, Carbohydrates and Proteins in Continuous Cultures of Oscillatoria Brevis Induced by Changes in Notrogen Supply," Arch Microbiol, 150:333-337 (1988).

Persson, F., et al., "Removal of Geosmin and MIB by Biofiltration—an Investigation Discriminating Between Adsorptionand Biodegradation," Environ. Technol., 28:95-104 (2007).

Saadoun, I.M., et al., "Environmental and Nutritional Factors Affecting Geosmin Syntheses by Anabaena Sp," Water Res., 35:1209-18 (2001).

Schnurer, J., et al., "Fungal Volatiles as Indictors of Food and Feeds Spoilage," Fungal Genet. Biol., 27:209-17 (1999).

Schrader, K.K., et al., "Cyanobacteria and Earthy/Musty Compounds Found in Commercial Catfish (*Ictalurus Punctatus*) Ponds in the Mississippi Delta and Mississippi—Alabama Blackland Prairie," Water Res., 39:2807-14 (2005).

Schulz, S., et al., "Identification and Syntheses of Volatiles Released by the Myxobaterium Chondromyces Crocatus," Tetrahedron, 60:3863-3872 (2004).

Sugiura, N., et al., "Significance fo Attached Cyanobacteria Relevant to the Occurrence of Musty Odor in Lake Kasumigaura," Water Research, 32:3549-3554 (1998).

Van Der Ploeg, M., et al., "Geosmin Production by Cyanobacteria (Blue-Green Algae) in Fish Ponds at Auburn, Alabama," Journal of the World Aquaculture Society, 22:207-216 (1991).

Watson, S.B., "Cyanobacterial and Eukaryotic Algal Odour Compounds: Signals or By-Products? A Review of Their Biological Activity," Phycologia, 42:332-350 (2003).

\* cited by examiner

```
NPUNMOD     MVMQPFELPEFYMPWPARLNPNLEAARSHSKAWAYQMGILGSKEEAESSVIWDERTFDAH
NJ2         --MQPFELPEFYMPWPARLNPNLEAARSHSKAWAYQMGILGSKEEAESSVIWDERTFDAH
ZP_00109187 --MQPFELPEFYMPWPARLNPNLEAARSHSKAWAYQMGILGSKEEAESSVIWDERTFDAH
SCO6073     MTQQPFQLPHFYLPHPARLNPHLDEARAHSTTWAREMGML------EGSGVWEQSDLEAH
SAV2163     -MTQPFQLPHFYMPYPARLNPHLDEARAHSTRWARGMGML------EGSGIWEQSDLDAH
             *.***.**.**.* ******.*.. **.**. **   **.*         *.* .*:*    ::**

NPUNMOD     DYALLCSYTHPDAPGTELDLVTDWYVWVFFDDHFLEIYKRTQDMAGAKEYLGRLPMFMP
NJ2         DYALLCSYTHPDAPGTELDLVTDWYVWVFFDDHFLEIYKRTQDMAGAKEYLGRLPMFMP
ZP_00109187 DYALLCSYTHPDAPGTELDLVTDWYVWVFFDDHFLEIYKRTQDMAGAKEYLGRLPMFMP
SCO6073     DYGLLCAYTHPDCDGPALSLITDWYVWVFFDDHFLEKYKRSQDRLAGKAHLDRLPLFMP
SAV2163     DYGLLCAYTHPDCDGPALSLITDWYVWVFFDDHFLETFKRTQDREGGKAYLDRLPLFMP
             **.***:*****.  *  *:.**********.******  :**:**  ..* .*.***:***

NPUNMOD     IYPTETPPVPTNPVECGLADLWSRTAFTKSVDWRLRFFESTKNLLEESLWELANINQDRV
NJ2         IYPTETPPVPTNPVECGLADLWSRTAFTKSVDWRLRFFESTKNLLEESLWELANINQDRV
ZP_00109187 IYPTETPPVPTNPVECGLADLWSRTAFTKSVDWRLRFFESTKNLLEESLWELANINQDRV
SCO6073     LDDAAGMPEPRNPVEAGLADLWTRTVPAMSADWRRRFAVATEHLLNESMWELSNINEGRV
SAV2163     LDLSAPVPEPENPVEAGLADLWARTVPAMSADWRKRFAVSTEHLLNESLWELSNINEGRI
             :    :   * * ****.******:**.  .*:.****:.*.  :*:.**:**:***:.*:

NPUNMOD     ANPIEYIEMRRKVGGAPWSADLVEHAVFIEIPADIASTRPMRVLKDTFADGVHLRNDLFS
NJ2         ANPIEYIEMRRKVGGAPWSADLVEHAVFIEIPADIASTRPMRVLKDTFADGVHLRNDLFS
ZP_00109187 ANPIEYIEMRRKVGGAPWSADLVEHAVFIEIPADIASTRPMRVLKDTFADGVHLRNDLFS
SCO6073     ANPVEYIEMRRKVGGAPWSAGLVEYAT-AEVPAAVAGTRPLRVLMETFSDAVHLRNDLFS
SAV2163     ANPVEYIEMRRKVGGAPWSAGLVEYAT-AEVPAAVAGSRPLRVLMETFSDGVHLRNDLFS
             ***:***************.***.*. .*:**. .*.**:***..**:*.********

NPUNMOD     YQREVEDEGENANCVLVLERFLNVSTQEAANLTNELLTSRLYQFDNTAVTELPPLFEEYG
NJ2         YQREVEDEGENANCVLVLERFLNVSTQEAANLTNELLTSRLYQFDNTAVTELPPLFEEYG
ZP_00109187 YQREVEDEGENANCVLVLERFLNVSTQEAANLTNELLTSRLYQFDNTAVTELPPLFEEYG
SCO6073     YQREVEDEGELSNGVLVLETFFGCTTQEAADLVNDVLTSRLHQFEHTAFTEVPAVALEKG
SAV2163     YQREVEEEGELSNGVLVLETFFGCTTQEAAETVNDILTSRLHQFEHTALTEVPALALEKG
             ******:***.:*.*****.*:.  :*****.: *: :*****:**::**.**:*.. * *

NPUNMOD     LDPVARVNVLLYIKGLQDWQSGGHEWHMRSSRYMNKGGDNSPTSTVLGGPTGLGTSAARI
NJ2         LDPVARVNVLLYIKGLQDWQSGGHEWHMRSSRYMNKGGDNSPTSTVLGGPTGLGTSAARI
ZP_00109187 LDPVARVNVLLYIKGLQDWQSGGHEWHMRSSRYMNKGGDNSPTSTVLGGPTGLGTSAARI
SCO6073     LTPLEVAAVGAYTKGLQDWQSGGHEWHMRSSRYMNKG---ERPLAGWQALTGPGTSAADV
SAV2163     LTPPEVAAVAAYARGLQDWQSGGHEWHMRSSRYMNEG---ALSQKRPFGLSAIGTSAADL
              * *  .  . *  .**********.********:*      . :. * * .****.:
```

Figure 2A

```
NPUNMOD       ESLYAALGLGRIKSFTHVPYQPVGPVTLPKFYMPFTTSLNPHLNAARKHSKEWARQMGML
NJ2           ESLYAALGLGRIKSFTHVPYQPVGPVTLPKFYMPFTTSLNPHLNAARKHSKEWARQMGML
ZP_00109187   ESLYAALGLGRIKSFTHVPYQPVGPVTLPKFYMPFTTSLNPHLNAARKHSKEWARQMGML
SCO6073       GALLADAVAQRARSYTYVPFQKVGPSVIPDIRMPYPLELSPALDGARRHLSEWCREMGIL
SAV2163       RGLLADAGAERLRRYTHVPFQKVGPSRIPDFHMPFQVELSPHLEGARARLTPWMHSTGML
               .* *      * : :*:**:* ***  :*.: **: .*.* *:.**  :  * :. *:*

NPUNMOD       ESLPGIPDAVIWDDHKFDVADVALCGALIHPNGSGLELNLTACWLVWGTYADDYFPALYG
NJ2           ESLPGIPDAVIWDDHKFDVADVALCGALIHPNGSGLELNLTACWLVWGTYADDYFPALYG
ZP_00109187   ESLPGIPDAVIWDDHKFDVADVALCGALIHPNGSGLELNLTACWLVWGTYADDYFPALYG
SCO6073       SEG------VWDEDKLESCDLPLCAAGLDPDATQDQLDLASGWLAFGTYGDDYYPLVYG
SAV2163       QEG------VWDEDKLTAYDLPLCSAGLDPDATPDELDLSSRWLAWGTYGDDYYPMVFG
               ..           :**:.*;    *:.**.*  :.*:.:   :*:*:: **,:***,***:* ::*

NPUNMOD       NNRNMAGAKVFNARLSAFMPLDDSTPSEVPTNPVEAGLADIWSRTAGPMSANARTQFRRA
NJ2           NNRNMAGAKVFNARLSAFMPLDDSTPSEVPTNPVEAGLADIWSRTAGPMSANARTQFRRA
ZP_00109187   NNRNMAGAKVFNARLSAFMPLDDSTPSEVPTNPVEAGLADIWSRTAGPMSANARTQFRRA
SCO6073       HRRDLAAARLTTTRLSDCMPLDG-EPVPPPGNAMERSLIDLWVRTTAGMTPEERRPLKKA
SAV2163       PRRDLAAAKLCTRRLSACMPVDG-EEVPAPVNGMERGLIDLWAITTAEMTPDERRTFRAS
               .*::*.*:: . *** **:*.   *  *  :* .* *:* *:. *:.: *   ::  :

NPUNMOD       IQDMTDSWVWELANQIQNRIPDPIDYVEMRRKTFGSDLTMSLSRLAQGSEIPQEIYRTRT
NJ2           IQDMTDSWVWELANQIQNRIPDPIDYVEMRRKTFGSDLTMSLSRLAQGSEIPQEIYRTRT
ZP_00109187   IQDMTDSWVWELANQIQNRIPDPIDYVEMRRKTFGSDLTMSLSRLAQGSEIPQEIYRTRT
SCO6073       VDDMTEAWLWELSNQIQNRVPDPVDYLEMRRATFGSDLTLGLCRAGHGPAVPPEVYRSGP
SAV2163       VDVMTESWVWELSNQLQHRIPDPIDYLEMRRATFGADLTLSLCRVGHGPKVPPEIYRSGP
               :: **::*:***:** :*:***:**:**** ***:.***.:.*. :*.  :* .:*;**:  .

NPUNMOD       MRSLDNSAADFACLTNDVFSYQKEIEFEGEIHNCVLVVQNFLNCDLPQAVEVVNNLMTSR
NJ2           MRSLDNSAADFACLTNDVFSYQKEIEFEGI------------------------------
ZP_00109187   MRSLDNSAADFACLTNDILFLSERNRIRGRNP----------------------------
SCO6073       VRSLENAAIDYACLLNDVFSYQKEIEYEGEIHNAVLVVQNFFGVDYPAALGVVQDLMNQR
SAV2163       VRSLENAAVDYGMLINDVFSYQKEIEYEGEVHNAILVVQNFFGCDYPTALGVINDLMTQR
               :***:*:*  *:. * **:: .:: . . .*

NPUNMOD       ALQFQLIVATELPVLFDDFDLDASTREKLLGYVKKLEQWMCGVLKWHITVDRYKEFELRN
NJ2           ------------------------------------------------------------
ZP_00109187   ------------------------------------------------------------
SCO6073       MRQFEHVVAHELPVVYDDFQLSEEARTVMRGYVTDLQNWMAGILNWHRNVPRYKAEYLAG
SAV2163       MHQFEHVAAHELPLLYKDFKLPQEVRDIMDGYVVELQNWMSGILKWHQDCHRYGAADLAR

NPUNMOD       SLAGRLLSGPRGLGTSARRIGSLIGQGSLKSLLGQ  (SEQ ID NO: 15)
NJ2           ----------------------------------   (SEQ ID NO: 25)
ZP_00109187   ----------------------------------   (SEQ ID NO: 26)
SCO6073       RTHGFLPDRIPAPPVPRSSPALTH----------   (SEQ ID NO: 27)
SAV2163       RAHGFVPDRAPSAPFTAWAAPVAR----------   (SEQ ID NO: 28)
```

Figure 2B

```
N. punctiforme    ------------------------------------------------------------
A. laxa           ------------------------------------------------------------
Phormidium calc.  ------------------------------------------------------------
Nostoc sp (UTAH)  ------------------------------------------------------------
SCO6073           DYGLLCAYTHPDCDGPALSLITDWYVWVZFDDDHFLEIYKRTQDMAGAKEYLGRLPMFMP
SAV2163           DYGLLCAYTHPDCDGPALSLITDWYVWVZFDDDHFLELYKRSQDMAGAKKYLDGLPAFMP
                                               *********  ***:::*  . *  *:.* ***

N. punctiforme    IYPTHTPFVPTNPVECGLADLWSRTAFTKSVDWRLRFFGSTKNLLEESLWELAYINQDRV
A. laxa           IYPRDNPLVPTNPVERGLADLWSRTAFTKSVEWRRRFFKSTKNLLDESMWELANINQNRI
Phormidium calc.  IHSTETMPAPTNPVERGLADLWSRTALITKSVEWRVRFSESTKNLLEESLWEIANTNQNRV
Nostoc sp (UTAH)  VQPQETPEPTNAVERGLVDLWDRTIPNASQDWVIRFSESTINLLKESQWELANISQNRV
SCO6073           LDDAAGMPEPRNPVEAGLADLWTRTVPAMSADWRRRFAVATEHLLNESMWELSNINEGRV
SAV2163           LDDLSAPVPEPENPVEAGLADLWARTVPAMSADWKRKRFAVSTEHLLNESLWELSNINEGRI
                    *.**  **.*** ** .   :     .  : *:.  .  **.: :: ::.

N. punctiforme    ANPIEYIEMRRKVGGAPWSADLVEHAVFIEIPADIASTRPMRVLKDTFADEVHLRNDLFS
A. laxa           ANPIEYIBMRRKVGGAPWSADLVEHAAFVEVPAKIAATRPMRVLKDTFADGVHLRNDLFS
Phormidium calc.  SNPIEYIEMRRKVGGAPWSADLVEHAAFVEVPAQIAATRPMRVLKDTFADGVHLHNDLFS
Nostoc sp (UTAH)  ANPIEYIEMRRKVGGAPWSANLVEHAVGADIPAAIAPTRPMRVLKDTFSDGVHLRNDLFS
SCO6073           ANPVEYIEMRRKVGGAPWSAGLVEYAT-ABVPAAVACTRPLRVLMETFSDAVHLRNDLFS
SAV2163           ANPVEYIEMRRKVGGAPWSAGLVEYAT-ABVPAAVAGSRPLRVLMETFSDGVHLRNDLFS
                   ** *******:*******.***:*    :  **   :** *** :**:. **:***:*.

N. punctiforme    YOREVEDEGENANCVLVLERFLNVSTQEAANLTNELLTSRLYQFDNTAVTELPPLFEEYG
A. laxa           YOREVEDEGENSNCVLVIEKFLNVSTQEAANLTNELLNSRLYQFDNTAVTELPSLFEEYG
Phormidium calc.  YOREVEDEGENANCVLVLERFLDVTTQEAANLTNELLSSRLYQFDNTAVTELPPLFEEHG
Nostoc sp (UTAH)  VEEBEGENANCILVLERFLDVSTQEAANLTNDLLTSRVQOPENIFVTELPSLFEEYS
SCO6073           LORSVEDEGELSNGVLVLETFPGCTTQEAADLVNDVLTSRLHQFEHTAFTEVPAVALEKG
SAV2163           LORSVEEEGELSNGVLVLETFPGCTTQEAAFTVNDILTSRLHQFEHTALTEVPALALEKG
                   . :  * ***.**:**:*:*  . .*** *  : :*: .:::                *

N. punctiforme    LDPVARVNVLLYIKGLQDWQSGGHEWHMRSSRYMNE------------- (SEQ ID NO: 14)
A. laxa           VDPVERVNVLLYIKGLQDWQSGGHEWHMRSSRYMNE------------- (SEQ ID NO: 13)
Phormidium calc.  LDPAARMSVVLYIKGLQDWQSGGHEWHMRSSRYMNK------------- (SEQ ID NO: 11)
Nostoc sp (UTAH)  LSPDERLKVLHAKGLQDWQSGGHEWHMRSSRYMNE------------- (SEQ ID NO: 12)
SCO6073           LTPLEVAAVGAYTKGLQDWQSGGHEWHMRSSRYMNKGERPLAGWQALTGPG--TSAADV (SEQ ID NO: 33)
SAV2163           LTPPEVAAVAAYARGLQDWQSGGHEWHLRSSRYMNEGALSQKRPFGLSAIG--TSAADL (SEQ ID NO: 34)
                   .*  :    * .*************:*******
```

Figure 5

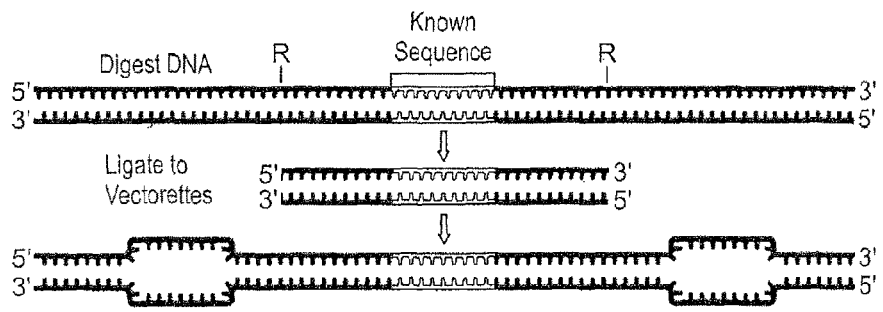
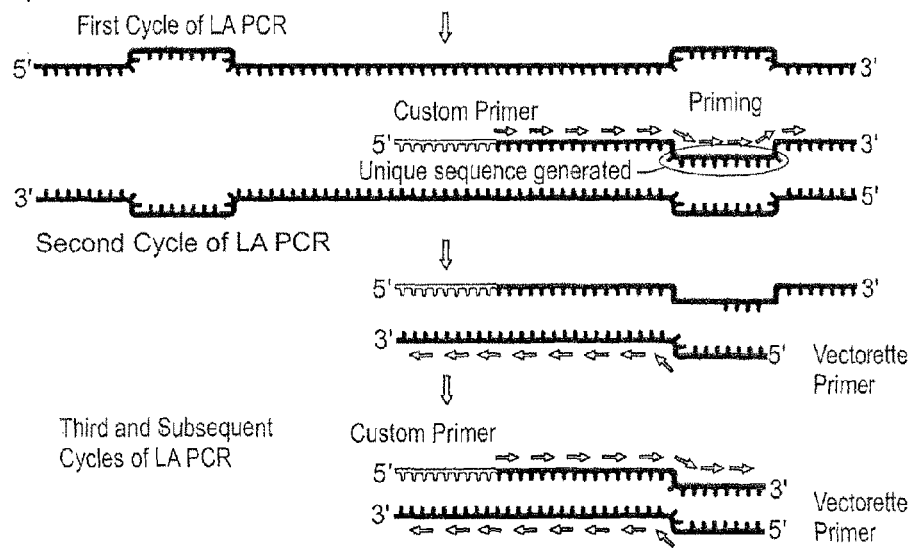
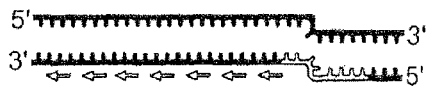
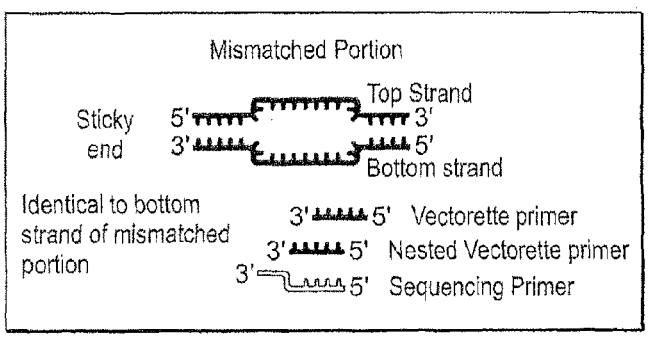
Figure 11

```
CLUSTAL W (1.83) multiple sequence alignment

Q1CYZ7|Q1CYZ7_MYXXD   MSTAKNKQPFELPDFYVPWPARLNPNLEGARVHSKAWARELGIIGRPKDGSAPEIWSEAK  60
Q09A24|Q09A24_STIAU   ------------------------------------------------------------
Q9X839|CYC2_STRCO     ----MTQQPFQLPHFYLPHPARLNPHLDEARAHSTTWAREMGMLE------GSGVWEQSD  50
Q82L49|Q82L49_STRAW   -----MTQPFQLPHFYMPYPARLNPHLDEARAHSTRWARGMGMLE------GSGIWEQSD  49
Q2J565|Q2J565_FRASC   ------MQPFTLPEFYVPYPARLNPNLEQARVHSRAWADEMEMIDSPQH--GTAIWTEAD  52
Q0RBQ4|Q0RBQ4_FRAAA   ------MQPFTLPEFYVPYPARLSPHLEQAREHSREWARAMEMIDTPQH--GIAIWTERD  52
Q3WJX6|Q3WJX6_9ACTO   ------MQPFTLPEFYLPYPRRLNPNLEHARVHSRAWAGEMEMIDVPQD--GVAIWSGQD  52
A4FEI8|A4FEI8_SACEN   ------MQPFQQPEFYMPYPARLNPNLERAREHSKAWACAMDIDVPQE--GTLIWDEND  52
A4FGS3|A4FGS3_SACEN   MPAPQQRQPYRLPAFYLPRPARLNPDLEAARARSRRWAEEMGMLGSRAEPEGEQVWTRED  60

Q1CYZ7|Q1CYZ7_MYXXD   FDAMDYALLCAYTHPEAPGPELDLVIDWYVWVFYFDDHFLELYKRPQDQVGAKAYLDRLP  120
Q09A24|Q09A24_STIAU   ---MDYALLCAYTHPEAPSLELDLVTDWYVWVFYFDDHFLDVYKRTQDQVGAREYLDRLP  57
Q9X839|CYC2_STRCO     LEAHDYGLLCAYTHPDCDGPALSLITDWYVWVFFFDDHFLEKYKRSQDRLAGKAHLDRLP  110
Q82L49|Q82L49_STRAW   LDAHDYGLLCAYTHPDCDGPALSLITDWYVWVFFFDDHFLETFKRTQDREGGKAYLDRLP  109
Q2J565|Q2J565_FRASC   FDAHDYALLCAYTHPDSVSRKLDLVTDWYVWVFYFDDHFLELYKRSHDMAGARAYLDRLP  112
Q0RBQ4|Q0RBQ4_FRAAA   LDAHDYALLCAYTHPDATADRLNLITDWYVWVFYFDDHFLELYKRSHDLAGARAYLDRLP  112
Q3WJX6|Q3WJX6_9ACTO   FDSHDYALLCAYTHPDADEARLDLITDWYVWVFYFDDHFLEVYKGRDVAGARRYLDRLR  112
A4FEI8|A4FEI8_SACEN   FDSHDYALLCAYTHPDADGPMLDLITDWYVWVFYFDDHFVELYKRNPDLAGAKEYLDRLP  112
A4FGS3|A4FGS3_SACEN   FDRHDYALLCAYAHPDASAPALELITGWYVWAFFFDDHFLARYKRTGDVDGARAHLLGLA  120

Q1CYZ7|Q1CYZ7_MYXXD   LFMPVDPAATPPPPTNPVEAGLLDLWNRTVPSRSMAWRRRFFESTKHLLDESSWELSNIS  180
Q09A24|Q09A24_STIAU   AFMPVDLSAAPPTPTNPVERGLADLWARTVPTKSEAWRRRFFESTKSLLEESNWELNNIS  117
Q9X839|CYC2_STRCO     LFMPLDDAAGMPEPRNPVEAGLADLWTRTVPAMSADWRRRFAVATEHLLNESMWELSNIN  170
Q82L49|Q82L49_STRAW   LFMPLDLSAPVPEPENPVEAGLADLWARTVPAMSADWRKRFAVSTEHLLNESLWELSNIN  169
Q2J565|Q2J565_FRASC   AFMPVDGEITE-TPTNPVERGLADLWTRTVPERSADWRRRFAVSTKNLLDESLWELANIN  171
Q0RBQ4|Q0RBQ4_FRAAA   AFMPVDGEITE-EPSNPVERGLADLWTRTVPARSADWRARFAVSTRNLLDESLWELENIN  171
Q3WJX6|Q3WJX6_9ACTO   LFMPVEGAVTA-EPANPVERGLADLWSRTVPDRTPAWRRRFATSTRHLLDESLWELANID  171
A4FEI8|A4FEI8_SACEN   AFMPVEGPITA-EPTNPVERGLADLWQRTVPARTADWRRRYAENTKHLLDESLWELSNIS  171
A4FGS3|A4FGS3_SACEN   ELMPVGPSDAAPAATGPVERGLADLWVRTAPEVPARWLVRFAASTRELLENRLRELTGTS  180

Q1CYZ7|Q1CYZ7_MYXXD   DRRVSNPIEYIEMRRKVGGAPWSANLVEHAVFAEVPDRVAASRPMRVLKDTFSDAVHLRN  240
Q09A24|Q09A24_STIAU   ERRVSNPIEYIEMRRKVGGAPWSADLVEHAVFAEIPARIAASRPMTVLKDTFSDGVHLRN  177
Q9X839|CYC2_STRCO     EGRVANPVEYIEMRRKVGGAPWSAGLVEYAT-AEVPAAVAGTRPLRVLMETFSDAVHLRN  229
Q82L49|Q82L49_STRAW   EGRIANPVEYIEMRRKVGGAPWSAGLVEYAT-AEVPAAVAGSRPLRVLMETFSDGVHLRN  228
Q2J565|Q2J565_FRASC   AGRLANPIEYVEMRRKVGGAPWSANLVEHAADAEVPAQVAATRPLQVLRDTFADAVHLRN  231
Q0RBQ4|Q0RBQ4_FRAAA   AARLSNPIEYIEMRRKVGGAPWSANLVEHAADAEVPARVAATRPLQVLRDTFADAVHLRN  231
Q3WJX6|Q3WJX6_9ACTO   ENRLANPVEYIEMRRKVGGAPWSANLVEHAADAEVPDAIAATRPAQVLRDTFSDAIHLRN  231
A4FEI8|A4FEI8_SACEN   RNRLSNPIEYIEMRRKVGGAPWSANLVEHAVDSEVPAAIASARPMQVLRDTFSDAVHLRN  231
A4FGS3|A4FGS3_SACEN   RCGVPNPVDHIAMRREAGGASWSAALVEYAAGSEVPDVVARSRPMRVLRDSFCDGVHLRN  240

Q1CYZ7|Q1CYZ7_MYXXD   DLFSYEREILEEGELSNGVLVMEKFLNISPPSAAHLVNEVLTSRLQQFENTVLTELPSLF  300
Q09A24|Q09A24_STIAU   DLFSYQREIQEEGELANCVLVFEKFLNVDAQRAANLVNEVLTSRLQQFENTALTELPSLF  237
Q9X839|CYC2_STRCO     DLFSYQREVEDEGELSNGVLVLETFFGCTTQEAADLVNDVLTSRLHQFEHTAFTEVPALA  289
Q82L49|Q82L49_STRAW   DLFSYQREVEEEGELSNGVLVLETFFGCTTQEAAETVNDILTSRLHQFEHTAVTELPAVL  288
Q2J565|Q2J565_FRASC   DLFSYQREVEEEGELSNGVLVIERFLDIDTQAAADTVNDLLTSRLHQFEHTAATELPAVL  291
Q0RBQ4|Q0RBQ4_FRAAA   DLFSYEREVTEEGELSNGVLVLERFLDCPTQQAADAVNDLLTSRLHQFEHTALTELPPVL  291
Q3WJX6|Q3WJX6_9ACTO   DLFSYQREVQEEGELSNGVLVLERFLDCPTQQAADAVNDLLTSRLHQFEHTALTELPPVL  291
A4FEI8|A4FEI8_SACEN   DLFSYQREVQDEGELSNSVLVFEKFLDCSTQDAADTVNDLLTSRLHQFEHTALTEVPALL  291
A4FGS3|A4FGS3_SACEN   DIFSYPRETSEEGELGNGVLVVERFFDTDPQEAADTVNDLLTSRLHQFENVTLTELPAMF  300

Q1CYZ7|Q1CYZ7_MYXXD   VEFGLNPVEQAQVLTYVRGLQDWQSGGHEWHMRSSRYMNKGSGGAG--------------  346
Q09A24|Q09A24_STIAU   EENALNPVERAHVLTYVRGLQDWQSGGHEWHMRSSRYMNKGAGGAGDTD-----------  286
Q9X839|CYC2_STRCO     LEKGLTPLEVAAVGAYTKGLQDWQSGGHEWHMRSSRYMNEGALSQKRPFG----------  338
Q82L49|Q82L49_STRAW   LEKGLTPPEVAAVAAYARGLQDWQSGGHEWHLRSSRYMNEGALSQKRPFG----------  338
Q2J565|Q2J565_FRASC   EEHGVDPGSRLEVLAYVKGLQDWQSGGHEWHLRSSRYMNRAVAPESGE------------  339
Q0RBQ4|Q0RBQ4_FRAAA   DEHAIDPAGRLAALAYIKGLQDWQSGGHEWHLRSSRYMNREATPDAVPPGLGPLAGLGGT  351
Q3WJX6|Q3WJX6_9ACTO   DEHGVPTARRDVLAYVKGLQDWQAGGHEWHMRSSRYMNAESGATGPVP-----------  340
A4FEI8|A4FEI8_SACEN   DENGVDPQGRLAVLGYVKGLQDWQSGGHEWHIRSSRYMNEGLVEQSALAGQSAPGQPALP  351
A4FGS3|A4FGS3_SACEN   EEHGLSPVERADVLDYVKGLQDWQSGAHEWHLRSGRYAVPGGAEPREPRR----------  350
```

Figure 12A

```
Q1CYZ7|Q1CYZ7_MYXXD    ------------GFFLGPNGLGTSAARLPQSPTALGLTRLKNFSHVPYQPVGPVKLPKFY  394
Q09A24|Q09A24_STIAU    ------------GLPLGLSGLGLSAVRPPFSASALGLNRFKSFTHTPYMPVGPVKLPKFY  334
Q9X839|CYC2_STRCO      ----------------LTGPGTSAADVGALLADAVAQRARSYTYVPFQKVGPSVIPDIR  382
Q82L49|Q82L49_STRAW    ----------------LSAIGTSAADLRGLLADAGAERLRRYTHVPFQKVGPSRIPDFH  381
Q2J565|Q2J565_FRASC    ----------LSGLLG-LTGLGTSAARIVPSLVTTTPRRIRSFTHIPHQIVGPLRHPDFC  388
Q0RBQ4|Q0RBQ4_FRAAA    GSLVPAA--GLPGIPG-IPSLGTSAIQVLPSLLATAPRRIRSFANVPFRLVGPTPLPEFY  408
Q3WJX6|Q3WJX6_9ACTO    ----------GSLPGDATGLGTSAVRIAASLLATAPARMRAFTHVPHQVVGPVKLPAFY  389
A4FEI8|A4FEI8_SACEN    QSAPDGTGPATQPVLGGPTGLGTSAARIVQSLLSTAPQRIRSFTHTPYEPAGPIRMPEIY  411
A4FGS3|A4FGS3_SACEN    ------------FLSGPHGLGTSSSHLGSLLRTVRPGLPIPHGQLRYARIA---VPAMS  394

Q1CYZ7|Q1CYZ7_MYXXD    MPYSTKPSPHLDAARRDSKAWARRMGMLDVLPGVPGGYIWDDHKFDVADVALCGALIHPH  454
Q09A24|Q09A24_STIAU    MPYSTSVSPHLDAARRHSKEWARQMGMLDSLPGLPGVYIWDDHKFDVADVALCGALIHPE  394
Q9X839|CYC2_STRCO      MPYPLELSPALDGARRHLSEWCREMGILS--EG-----VWDEDKLESCDLPLCAAGLDPD  435
Q82L49|Q82L49_STRAW    MPFQVELSPHLEGARARLTPWMHSTGMLQ--EG-----VWDEDKLTAYDLPLCSAGLDPD  434
Q2J565|Q2J565_FRASC    MPFSTGQSPHLDASRRENIIWARAVGMLDPIPG-----IWDEHKLRAFDFALCSAGIHPD  443
Q0RBQ4|Q0RBQ4_FRAAA    LPYTTGLSPHLDSSRRAIIPWARSMGMLDRVPG-----IWDEHKLWSYDFALCSAGIHPD  463
Q3WJX6|Q3WJX6_9ACTO    MPFTTGESRHLAAARHNIVEWSAAVGFLDPVPG-----IWDEHXLRAADFALCSAAIHPN  444
A4FEI8|A4FEI8_SACEN    MPFDLSLSPHLDVCRENTAAWARAMGIFDDVPR-----VWDENQMRGYDLPLCSAGLDPD  466
A4FGS3|A4FGS3_SACEN    SPHPVRTNPQVGTVRAHAKEWARRMGMLDSGG------VWTANVFDAADFGQFSAMAHPD  448

Q1CYZ7|Q1CYZ7_MYXXD    ATAAQLNLSSCWLVWGTYADDYFPAFYGHTKDMAGAKVFNARLALFVPEDAGAVVPPPTN  514
Q09A24|Q09A24_STIAU    ASAEQLNLTACWLVWGTYADDYFPAFYGYTRDMAGAKLFNARLSAFMPDGPCTAVP--TN  452
Q9X839|CYC2_STRCO      ATQDQLDLASGWLAFGTYGDDYYPLVYGHRRDLAAARLTTTRLSDCMPLD-GEPVPPPGN  494
Q82L49|Q82L49_STRAW    ATPDELDLSSRWLAWGTYGDDYYPMVFGPRRDLAAAKLCTRRLSACMPVD-GEEVPAPVN  493
Q2J565|Q2J565_FRASC    ATLPELNLTTDWLTWGTYADDYYPVIFGRTRDILGAKVCNARLSEFMPLD-SPVTAVPAN  502
Q0RBQ4|Q0RBQ4_FRAAA    ATADELDLTTAWLTWGTYGDDYYPVIFGASRNLAAAKLCNERLRLFMPVD-GPLTEPPVN  522
Q3WJX6|Q3WJX6_9ACTO    ATAAELDLTTGWLTWGTYADDLYPVLYGRTRDLAGARACTERLKELMPVE-PGPLPVPVG  503
A4FEI8|A4FEI8_SACEN    ATPEELDLSAAWLTWGTYGDDYYPRVFGRTLDMAGARACNARLKELMPVE-SAPATAPVT  525
A4FGS3|A4FGS3_SACEN    SPGPELELVNDWHVWGWFDDFFTEVFKRSRNRAGAEAFLARLPGFMPAD-TRRTPAPAN  507

Q1CYZ7|Q1CYZ7_MYXXD    PVERGLADLWARTTEGVTPASRSLFRKAILDMTESWVWELANQIQNRIPDPIDYVEMRRQ  574
Q09A24|Q09A24_STIAU    PVEHGLADLWARTAGPMTDNARRLFRKAIQDMTASWLWELANQIQNRIPDPVDYVEMRRK  512
Q9X839|CYC2_STRCO      AMERSLIDLWVRTTAGMTPEERRPLKKAVDDMTEAWLWELSNQIQNRVPDPVDYLEMRRA  554
Q82L49|Q82L49_STRAW    GMERGLIDLWAITTAEMTPDERRTFRASVDVMTESWVWELSNQLQHRIPDPIDYLEMRRA  553
Q2J565|Q2J565_FRASC    ALERGLADLWTRTTETMAPGARETFRGTVEVMIDSWLWELANQAQNRIPDPIDYIEMRRA  562
Q0RBQ4|Q0RBQ4_FRAAA    ALERGLADLWERTGAGMEPAARATFRRTIEVMIDSWLWELANQAHNRIPDPVDYLEMRRA  582
Q3WJX6|Q3WJX6_9ACTO    GLERGLADLWPRTTRDMTPDSRRTFRRTVCIMLDSWQWELANQAQNRIPDPVDYIEMRRR  563
A4FEI8|A4FEI8_SACEN    PLERGLADLWARTAGPMPVETRRRFRAAVDTMIDSWLWELHNQHLNRIPDPVDYFEMRRR  585
A4FGS3|A4FGS3_SACEN    PVERGLADLWARSTPVLAPRLRRRFPEHVRNFVGSWLWELDNLIQNRVSDPVDYLRMRRR  567

Q1CYZ7|Q1CYZ7_MYXXD    TFGSDLTMSLSRLAHG---DALPPEVFHTRPIRSLENSAADYACLINDVFSYQKEIEFEG  631
Q09A24|Q09A24_STIAU    TFGSDLTMSLSRLAHG---DAIPQEIFHTRPVRGLENSAADYACLTNDIFSYQKEIEYEG  569
Q9X839|CYC2_STRCO      TFGSDLTLGLCRAGHG---PAVPPEVYRSGPVRSLENAAIDYACLLNDVFSYQKEIEYEG  611
Q82L49|Q82L49_STRAW    TFGADLTLSLCRVGHG---PKVPPEIYRSGPVRSLENAAVDYGMLINDVFSYQKEIEYEG  610
Q2J565|Q2J565_FRASC    TFGSDLTMSLARLARLAQEQTVPPEIYRTRPIQALENAAADYACLLNDVFSYQKEIQFEG  622
Q0RBQ4|Q0RBQ4_FRAAA    TFGSDLTMSLCRLAR---WHSVPAEVFGTRPLRALENAAADYACLLNDIFSYQKEIQFEG  639
Q3WJX6|Q3WJX6_9ACTO    TFGSDLTMSLSRLGHG---RSVPPEIYGTRPIRALENSAADYSCLLNDIFSYQKEIQFEG  620
A4FEI8|A4FEI8_SACEN    TFGSDLTISLAKFSHG---EAVPPEIYRTRTIRNMENSAIDYATMLNDVFSYRKEIEYEG  642
A4FGS3|A4FGS3_SACEN    TGGSAFRGALARHTLG---AGLAPAVFDTPEMRALHENWADVGPLRNDLFSYHKEVDRET  624

Q1CYZ7|Q1CYZ7_MYXXD    ELNNGVLVVQRFLDLDPARAVSVVNDLMTARMQQFEYIIANELEPLARNFNLDGKAQDKL  691
Q09A24|Q09A24_STIAU    ELNNGVLVVQRFLEIEPPQAVEIVNDLMTARMRQFEHTVKMELPLLIRSTGLDAKAQEKL  629
Q9X839|CYC2_STRCO      EIHNAVLVVQNFFGVDYPAALGVVQDLMNQRMRQFEHVVAHELPVVYDDFQLSEEARTVM  671
Q82L49|Q82L49_STRAW    EVHNAILVVQNFFGCDYPTALGVINDLMTQRMHQFEHVAAHELPLLYKDFKLPQEVRDIM  670
Q2J565|Q2J565_FRASC    EIHNCVLVVENFLDCDRERALAVVNDLMTSRIRQFEHIVAHELPALFDSFALDASARQAL  682
Q0RBQ4|Q0RBQ4_FRAAA    EIHNCVLVVENFLDCDRGRAVEVVNALMTARMRQFEHVVDRELPDLFDRLDLDGEARAAI  699
Q3WJX6|Q3WJX6_9ACTO    EIHNCVLVFQNFLGCGAERAIGVVNDLMTARLREFEHVVDVELPALFDTYELTEEARDVL  680
A4FEI8|A4FEI8_SACEN    EVHNAVLVVRNFLDCDQDRAFEIVGDLMTARMKQFQYTVDDELPVLCEDFGLSSESRAVL  702
A4FGS3|A4FGS3_SACEN    EVTNGVLAVQRFFDCGLQQAAAVVADLAEVRLRRFTAVAEQELPALAHRFEPGRAPREEL  684
```

Figure 12B

```
Q1CYZ7|Q1CYZ7_MYXXD    KQYVQKLQWWMSGVLIWHQTVDRYKEFELRASRK----------LAPRLSSGPTGLGTS 740
Q09A24|Q09A24_STIAU    RTYVEKLQRWMCGVLRWHMTVDRYKEFELRNTRKPRRGGWEDPRDGAPPRPASRRSLGAT 689
Q9X839|CYC2_STRCO      RGYVTDLQNWMAGILNWHRNVPRYKAEYLAGRTHGFL---------PDRIPAPPVPRSSP 722
Q82L49|Q82L49_STRAW    DGYVVELQNWMSGILKWHQDCHRYGAADLARRAHGFV---------PDRAPSAPFTAWAA 721
Q2J565|Q2J565_FRASC    LGYARELQNWLAGILRWHEGTHRYEESELRYHPAAG----------VRPFGGPTGLGTS 731
Q0RBQ4|Q0RBQ4_FRAAA    VSYARELQNWLAGILRWHQGTHRYEEAELRYHPAAD----------RRPFGSPTGLGTS 748
Q3WJX6|Q3WJX6_9ACTO    RGYVGELKSWLAGVLRWHQGTRRYDEAELRHHPAVG----------VRPFGGPVGLGTS 729
A4FEI8|A4FEI8_SACEN    TRYADELRDWMSGILNWHRECVRYKDEDLRHDAVSQG---------LAALLRGPSGLGTS 753
A4FGS3|A4FGS3_SACEN    DRYVRGLHDWLAGELAWSQVTGRYREPSVSAVGADLP---------------AAPLGITGA 730

Q1CYZ7|Q1CYZ7_MYXXD    AARITSLFANLRSGA------ 755   (SEQ ID NO: 16)
Q09A24|Q09A24_STIAU    GAEVEKKLEKSGSST------ 704   (SEQ ID NO: 17)
Q9X839|CYC2_STRCO      ALTH----------------- 726   (SEQ ID NO: 18)
Q82L49|Q82L49_STRAW    PVAR----------------- 725   (SEQ ID NO: 19)
Q2J565|Q2J565_FRASC    SAHVRPRPAAAAGAAGDSEM- 751   (SEQ ID NO: 20)
Q0RBQ4|Q0RBQ4_FRAAA    AADVR-RLASR---------- 758   (SEQ ID NO: 21)
Q3WJX6|Q3WJX6_9ACTO    AADIRRALSGKSGQPTALTGS 750   (SEQ ID NO: 22)
A4FEI8|A4FEI8_SACEN    AVELR---------------- 758   (SEQ ID NO: 23)
A4FGS3|A4FGS3_SACEN    AG------------------- 732   (SEQ ID NO: 24)
```

Figure 12C

Sequences

Geosmin synthases
*Streptomyces scabies* geosmin synthase (translation of nt
2284449-2282248)
MTQPFALPHFYLPYPARLNPHLEEARAHSSVWAREMGMLEGSGVWNQADLDAHDYGLLCA
YTHPDCDGPALSLITDWYVWVFFFDDHFLELYKRSQDRPGGKAHLDRLPLFMPLDLSTPV
PEPRNPVEAGLADLWARTVPSMSMDWRRRFAVATEHLLNESMWELSNINEGRIANPVEYI
EMRRKVGGAPWSAGLVEYATAEVPESVADTRPLRVLMETFSDAVHLRNDLFSYQREVEEE
GENSNGVLVLETFFGCGTQQAAETVNDILTSRLHQFEDTALTEVPAIAVEKGLTPGEVAA
VAAYTKGLQDWQSGGHEWHMRSSRYMNEGATSARGPLDLGGAVLSGPALVTRAGHGTSAA
DVGALLATAAAQRLRAHTHQPYQKVGPSLLPDFHMPFRVALCPHLDGARPRLTAWAHAMG
ILSEGVWDEERLAAADLPLCSAGLDPDATPEQLDLSSAWLAWGTYGDDYYPLVFGHRRDL
AAARLTTARLSDCMPLDGERAPLPSNAMERALVDLWTRTTAAMTPDERRGLKESVDKMTE
SWVWEVFNQIHHRVPDPVDYLEMRRATFGSDLTLSMCRMGHGPQIPPEVYRSGPVRSLEN
AAIDYGCLINDVFSYQKEIEYEGEVHNAILVVQNFFGCDYPAALGVVHDLMTQRMRQFEH
VVAHELPVVYDDFRLSREARDIMGGYVTDLQNWMAGILNWHRNVDRYKPEFLARRAHNFV
PDRPPTLSLTPLRT                              SEQ ID NO: 78

*Streptomyces peucetius* geosmin synthase (spterp13)
MAQPFVLPDFYVPYPARLNRHVEEARRHSKKWARRMGMLEGSGIWEESDLDAHDYALLCA
YTHPDCDADALGLVTDWYVWVFFFDDHFLEVFKRSQDLAGGKAYLDRLPAFMPMDLSRGT
PEPRNPVEAGLADLWQRTVPSMSPAWRTRFAEATEHLLNESMWELTNIDAGRVANPVEYI
EMRRKVGGAPWSAGLVEYAAQAEVPESVAGARPLRVLRDSFSDAVHLRNDLFSYQREVED
EGENSNGVLVLERFLGCGTQEAAEVVNDLLTSRVQQFENTALTEVPALCVQKGLAPAECA
AIAAYTKGLQDWQSGGHEWHMRSSRYMNEGVETERSRFEGVLATSALDIRTLFGRPAAAR
MRTLTHRPQQVGPSWLPDFDLPFPLSLSPHLEQARAASVAWAGRMGLLGDIWDEAKLTGF
DFALCSAGLDPDATPEELELSAEWLTWGTYGDDYYPLVFGRARALEGARLCNERLKACMP
VDEPAAGAAVAVAPMERSLADLWARTAGPMSPGARSSLRSAIDVMLDSWLWELHNQAQHR
VPDPVDYIEMRRLTFGSDLTMSLCRLRHEGELPPELYASGPVRGLENAAMDYACLINDLF
SYQKEIEYEGEVHNAVLVVQTFFDCDRPTAAAMTDALMRSRLEQFLHTKEHELPLVCEEF
GLDEGGSAALGTYVRELEDWLAGILNWHRKVRRYKEEDLRGGAVPRRLGAPTGLGTSAAR
LSLPSRLSGVGV                                SEQ ID NO: 79

Figure 13A

*Saccharopolyspora erythraea* geosmin synthase 3
>tr|A4FJE8|A4FJE8_SACEN Terpene synthase, Saccharopolyspora
erythraea (strain NRRL 23338)
MQPFRLPEFYVPWPARLNPHLETAREHSKAWAREMGMLPGGPLGDDQAVWDEATFDAHDY
ALLCAYTHPDATAHELGLVTDWYVWVFYFDDHFLEYYKRTRDLTGAREYLAGLAAFMPAE
LTAEQPTAKNPVEWGLVDLWARSVPIMSADWLRRFSESTRNLLEDCVWELTNITHGQVPN
PIDYVEMRRRVGGAPWSADLVELAARVEVPAQIARTRPMSVLKDTFADAVHLRNDIFSYQ
RETEEEGELNNGVLVFERFLDCGPQEAADTTNELLTSRLQQFENTALTEVPPLCEEYGLD
PAERAAVLTYVKGLQDWQSGGHEWHLRSSRYMNDGALAGARSPFGGPTGLGTSAAHNALA
RVRPGIRRHREQHSHAPFAPVGHLPLPEIYMPFPVRMSPHLDAARQHAVDWAREMGMFDS
VPGSEVGGVWNERRFVGFDFPHCAAMIHADAGPEQLDLSSDWLAWGTYGDDFFPVVFGAT
RNLAAAKVCNDRLSAFMPIDGGGVPEPANVLERGLADLWRRTAGPMPADSRRQFRKAVED
MTSSWLWELANQTQNRIPDPVDYIEMRRRTFGSDTMSLSRLANAAVVPAEIYRTRVMRE
LEWSAQDYACFTNDLFSYQKEIEFEGEVHNMVLVVENFLGVDRLTARDVVADLMKARMRQ
FERILAEELPTLIDEFELDEAARTALTRQCDELKDWTSGILEWHRRCVRYTDAELRRTRS
EHHHGTGPEPHLPLRRRLSGPTGIGTSAARLARRGSSATGLNR    SEQ ID NO: 43

Figure 13B

2-Methylisoborneol synthases

*Streptomyces* sp. Mg1 2-methylisoborneol synthase (B4VFG0)
>tr|B4VFG0|B4VFG0_9ACTO Putative uncharacterized protein
OS=Streptomyces sp. Mg1
MPEPDPVRVEEVSRRIKEWAVDEVELYPPEWEDQFDGFSVGRYMVACHPDAPTVDHLMIA
TRLMVAENVVDDCYCEDHGGSPVGLGGRLLLAHTALDALHTTREYAPDWEESLHSDAPRR
AYRSAMEYFTREATASQADRYRHDMARLHLGYLAEAAWAQTDYVPQVWEYLAMRQFNNFR
PCPTITDTVGGYELPADLHAQAAVQRVIALAGNATTIVNDLYSYTKELASPGRHLNLPVV
VAEHEGGDVRDAYLKAVEVHNDLMHAFEAEAAELAAACPVPSVLRFLRGVAAWVDGNHYW
HQTNTYRYSLPDFW                          SEQ ID NO: 29

*Streptomyces ambofaciens* 2-methylisoborneol synthase (A3KI17)
>tr|A3KI17|A3KI17_STRAM Putative cyclase OS=Streptomyces
ambofaciens ATCC 23877
MPDSGPLGPHSPDHRPTPATTVPDAPASKPPDVAVTPTASEFLAALHPPVPIPSPSPPSG
SASAAADTPDATTVGSALQRILRGPTGPGTAALALSVRHDPPSLPGSPAPAEPAAGRAVP
GLYHHPVPEPDPARVEEVSRRIKRWAEDEVQLYPEDWEGEFDGFSVGRYMVACHPDAPTV
DHLMLATRLMVAENAVDDCYCEDHGGSPVGLGGRLLLAHTAIDPFHTTAEYAPPWRESLT
SDAPRRAYRSAMDYFVRAATPSQADRYRHDMARLHLGYLAEAAWAQTDHVPEVWEYLAMR
QFNNFRPCPTITDTVGGYELPADLHARPDMQRVIALAGNATTIVNDLYSYTKELDSPGRH
LNLPVVIAERERLSERDAYLKAVEVHNELQHAFEAAAAELAKACPLPTVLRFLKGVAAWV
DGNHDWHRTNTYRYSLPDFW                    SEQ ID NO: 30

*Streptomyces scabies* 2-methylisoborneol synthase partial
sequence (translation of nt 572020-570920)
DDALRRILRAPTGPGTASLVVADRFAPPLPSPVSRAPVEPAAGRAVPGLYHHPVPEPDPV
RVEEVSRRIKRWAEEEVQLYPEEWEGQFDGFSVGRYMVACHPDAPTTDHLMLATRLMVAE
NAVDDCYCEDHGGSPVGLGGRLLLAHTALDHFHTTAEYAPAWQESLASDAPRRAYRSAMD
HFVGAATPSQADRYRHDMARLHLGYLAEAAWAQTGHVPEVWEYLAMRQFNNFRPCPTITD
TVGGYELPADLHARPDMQRVIALAGNATTIVNDLYSYTKELDSPGHHLNLPVVIAERERL
PVRDAYLKAVEVHNELQHAFEAASAELAEACPLPAVLRFLKGVAAWVDGNHDWHRTNTYR
YTLPDFW                                 SEQ ID NO: 31

Figure 13C

*Streptomyces griseus 2-methyl isoborneol synthase*
>tr|B1VVB4|B1VVB4_STRGG Putative uncharacterized protein
OS=Streptomyces griseus subsp. griseus (strain JCM 4626 / NBRC
13350)
MPVPELPPPRSSLPEAVTRFGASVLGAVAARAHDSEATVGGPSGGRPLPSPPAGLSFGPP
SPAAPSADVPAPEAPGRGADLERLLCGPHGLGTAGLRLTPGKERPVPATAREGRPIPGLY
HHPVPEPDEARVEEVSRRIKAWALDEVSLYPEEWEEQFDGFSVGRYMVGCHPDAPTVDHL
MLATRLMVAENAVDDCYCEDHGGSPVGLGERLLLAHTALDPLYTAREYQPGWAASLHADA
PRRAYRSAMDYFVRAAGPSQADRLRHDMARLHLGYLAEAAWAQQDQVPEVWEYLAMRQFN
NFRPCPTITDTVGGYELPADLHAQAAMQKVIALASNATTIVNDLYSYTKELAAPGRHLNL
PVVIAEREGLSDQDAYLKSVEIHNELMHAFESEAAALAAACPVPSVQRFLRGVAAWVDGN
HHWHRSNTYRYSLPDFW                    SEQ ID NO: 32

METHODS OF DETECTING SOURCES OF MICROORGANISM CONTAMINATION

RELATED APPLICATIONS

This application is a continuation of International Application No. PCT/US2009/057266, which designated the United States and was filed on Sep. 17, 2009, published in English, which claims the benefit of U.S. Provisional Application No. 61/192,309, filed on Sep. 17, 2008. The entire teachings of the above applications are incorporated herein by reference.

GOVERNMENT SUPPORT

The invention was supported, in whole or in part, by a grant GM30301 from the National Institutes of Health. The Government has certain rights in the invention.

BACKGROUND OF THE INVENTION

Geosmin and 2-methylisoborneol are volatile organic compounds frequently found as contaminants in drinking water and fish raised by aquaculture methods. Although not toxic to humans, geosmin and 2-methylisoborneol are generally associated with an undesirable musty or muddy taste and odor in the sources in which they are present. Geosmin and 2-methylisoborneol are generated by a variety of microorganisms, including several species of cyanobacteria, as products of pathways that include geosmin synthase and 2-methylisoborneol synthase. Currently, geosmin and 2-methylisoborneol are detected after their production by an unpleasant odor in a source. Early detection of sources of microbial contamination, for example, prior to an unpleasant odor, may be important in developing effective remediation plans for reducing or eliminating geosmin and 2-methylisoborneol contamination in natural resources, including water, food sources and other materials. Thus, there is a need to develop new, improved and effective methods for detecting microbial sources of geosmin and 2-methylisoborneol contamination.

SUMMARY OF THE INVENTION

The present invention generally relates to methods and compositions for detecting a source of a microbial contamination in a suspect sample.

In an embodiment, the invention is a method of detecting a source of a microbial contamination in a suspect sample, comprising the step of detecting at least one member selected from the group consisting of a microbial geosmin synthase, a microbial 2-methylisoborneol synthase, and a microbial 2-methylgeranyl diphosphate synthase in the suspect sample.

In another embodiment, the invention is a method of identifying a source of a microbial contamination, comprising the step of conducting a nucleic acid amplification assay in the presence of at least one member selected from the group consisting of at least one microbial geosmin primer, at least one microbial 2-methylisoborneol synthase primer and at least one microbial 2-methylgeranyl diphosphate synthase primer on a sample obtained from a suspect source of the microbial contamination.

In a further embodiment, the invention is a method of detecting at least one member selected from the group consisting of a geosmin producing microorganism and a 2-methylisoborneol producing microorganism in a sample, comprising the steps of amplifying at least one nucleic acid in the sample in the presence of at least one member selected from the group consisting of a geosmin synthase primer, a 2-methylisoborneol synthase primer and a 2-methylgeranyl diphosphate synthase primer to thereby generate amplified products; and detecting at least one member selected from the group consisting of a geosmin synthase nucleic acid, a methylisoborneol synthase nucleic acid, and a 2-methylgeranyl diphosphate synthase nucleic acid in the amplified products.

In an additional embodiment, the invention is an isolated nucleic acid comprising at least one member selected from the group consisting of SEQ ID NO: 7, SEQ ID NO: 8, SEQ ID NO: 9 and SEQ ID NO: 10.

In yet another embodiment, the invention is an isolated polypeptide comprising at least one member selected from the group consisting of SEQ ID NO: 11, SEQ ID NO: 12, SEQ ID NO: 13, SEQ ID NO: 14 and SEQ ID NO: 15.

The methods and compositions of the invention can be employed to detect sources of microbial contamination. Advantages of the claimed invention include, for example, the ability to more rapidly and reliably predict contamination consequent to microorganisms, such as algal blooms associated with geosmin and 2-methylisoborneol contamination; and the detection of microbial organisms that produce geosmin and/or 2-methylisoborneol before the levels of these compounds become detectable by sensory stimuli, such as smell and taste.

BRIEF DESCRIPTION OF THE DRAWINGS

FIGS. 2A and 2B depict an alignment of proteins (SEQ ID NOS.: 15 and 25-28) from *Nostoc punctiforme* (published ZP_00109187, experimental NJ2, and experimental NPUN-MOD), *Streptomyces coelicolor* A3(2) (SCO6073) and *Streptomyces avermitilis* (SAV2163). Black boxed residues indicate conserved terpene synthase motifs; the boxed isoleucine residue near the carboxy-terminus of the ZP_00109187 sequence in FIG. 2B identifies the site of a sequencing error ("*" indicates exact sequence match, ":" indicates moderate match, "." Indicates low match)

FIG. 5 depicts alignments of amino (N)-terminal domains of protein sequences (SEQ ID NOS.: 11-14, 33 and 34) derived from the PCR products obtained from geosmin-producing organisms. Conserved magnesium binding domains, such as DDHFLE (SEQ ID NO.: 37) and NDLFSYQRE (SEQ ID NO.: 44), are indicated in the blacked background. SCO6073 and SAV2163 are protein sequences derived from *S. coelicolor* and *S. avermitilis* respectively. ("*" indicates exact sequence match, ":" indicates moderate match, "." Indicates low match).

FIG. 11 depicts a schematic of a vectorette approach to determine the sequence of cyanobacterial 2-methylisoborneol synthase genes.

FIGS. 12A, 12B and 12C depict a ClustalW alignment of presumptive germacradienol-geosmin synthase proteins (SEQ ID NOS.: 16-24) with *S. coelicolor* SCO6073. Q1CYZ, *Myxococcus xanthus* strain DK 1622; Q09A24, *Stigmatella aurantiaca* DW4/3-1; Q9X839, *S. coelicolor* A3(2); Q82L49, *S. avermitilis*; Q2J565, *Frankia* sp. Strain Cc13; Q0RBQ4, *Frankia alni* ACN14a; Q3WJX6, *Frankia* sp. EAN1pec; A4FEI8 and A4FGS3, *Saccharopolyspora erythraea* NRL 2338 (SEQ ID NOS.: 16-24). Conserved $Mg^{2+}$-binding motifs (DDHFLE (SEQ ID NO: 37); NDLFSYERE (SEQ ID NO: 76); NEVLTSRLQQFE (SEQ ID NO: 77); DDYFP (SEQ ID NO: 45); and NDVFSYQKE (SEQ ID NO: 75) in bold.

FIGS. 13A-13D depict amino acid sequences of geosmin synthases of the microorganisms *Streptomyces scabies* (SEQ ID NO: 78), *Streptomyces peucetius* (SEQ ID NO: 79), *Saccharopolyspora erythraea* (SEQ ID NO: 43) (FIGS. 13A and 13B) and 2-methylisoborneol synthases of the microorganisms *Streptomyces* sp. (SEQ ID NO: 29), *Streptomyces scabies* (SEQ ID NO: 30), *Streptomyces ambofaciens* (SEQ ID NO: 31), and *Streptomyces griseus* (SEQ ID NO: 32) (FIGS. 13C and 13D).

DETAILED DESCRIPTION OF THE INVENTION

Figure 1:
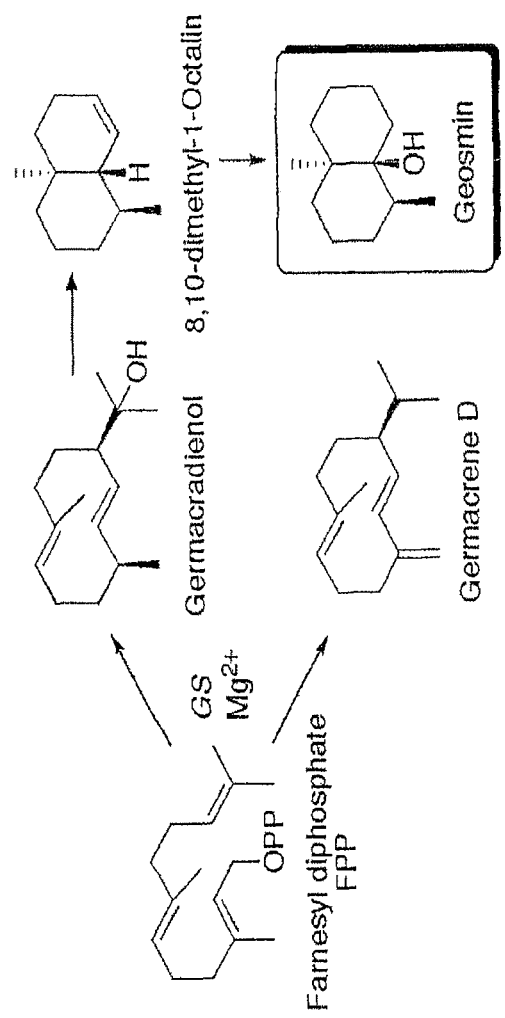
FIG. 1 depicts geosmin synthase (GS)-catalyzed cyclization of farnesyl diphosphate (FPP) to geosmin, germacradienol, germacrene D, and 8,10-dimethyl-1-octalin. Germacradienol and germacrene D are formed by the N-terminal domain of the bifunctional protein, and geosmin is generated from germacradienol via the octalin by the C-terminal domain.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principal features of this invention can be employed in various embodiments without departing from the scope of the invention.

In an embodiment, the invention is a method of detecting a source of a microbial contamination in a suspect sample, comprising the step of detecting at least one member selected from the group consisting of a microbial geosmin synthase and a microbial 2-methylisoborneol synthase in the suspect sample.

"Source of a microbial contamination," as used herein, refers to an origin or point of origin of a microorganism (e.g., fungi, bacteria, algae). The source of the microbial contamination can contain at least one member selected from the group consisting of a geosmin synthase nucleic acid or protein, a 2-methylisoborneol synthase nucleic acid or protein, and a 2-methylgeranyl diphosphate synthase (geranyl diphosphate C-methyl transferase) nucleic acid or protein. Microbial contamination can be consequent to a cyanobacterial contamination, an actinomycete contamination (e.g., actinomycetes, *Streptomyces*), a myxobacterial contamination and a fungal contamination.

In an embodiment, the source of a microbial contamination is consequent to the presence of a cyanobacterial contamination, for example, a cyanobacterial contamination that includes at least one member selected from the group consisting of *Phormidium* sp., *Phormidium calcicola*, *Anabaena circinalis*, *Anabaena laxa*, *Geitlerinema* sp., *Nostoc punctiforme*, *Nostoc* sp., *Pseudoanabaena limnetica*, *Pseudanabaena* sp., *Oscillatoria* sp., *Lyngbya* sp., *Planktothrix* sp., *Tyconema* sp., *Hyella* sp., *Anabaena* sp. and *Aphanizomenon* sp.

Microbial contamination can also be consequent to the presence of at least one member selected from the group consisting of *Streptomyces coelicolor*, *Myxococcus xanthus*, *Stigmatella aurantiaca*, *Streptomyces avermitilis*, *Frankia* sp., *Frankia alni* and *Saccharopolyspora erythraea*.

Table 1 lists exemplary sources of microbial contamination that may be consequent to bacterial geosmin proteins (SEQ ID NOS.: 16, 17, 19-24, 43, 78 and 79), as shown in FIGS. 12A, 12B and 12C. The microorganisms listed in Table 1 produce geosmin synthase that share identity to the geosmin sythase of SEQ ID NO.: 18. The methods described herein can detect any one or more of the geosmin synthases listed in Table 1 in a suspect sample.

TABLE 1

Amino acid sequence comparison of *S. coelicolor* SCO6073 germacradienol-geosmin synthase (Q9X839, CYC2_STRCO; SEQ ID NO: 18) with bacterial orthologs.

| Organism | UniProt ID | aa | Identity (%) | Similarity (%) |
|---|---|---|---|---|
| *Streptomyces scabies* (SEQ ID NO: 78) | [a] | 738 | 78 | 85 |
| *Streptomyces avermitilis* (SEQ ID NO: 19) | Q82L49 | 725 | 76 | 85 |
| *Streptomyces peucetius* ATCC 27952 (SEQ ID NO: 79) | spterp13 [b] | 732 | 64 | 74 |
| *Frankia* sp. Strain Cc13 (SEQ ID NO: 20) | Q2J565 | 751 | 60 | 72 |
| *Saccharopolyspora erythraea* NRL 2338 (SEQ ID NO: 23) | A4FEI8 | 758 | 58 | 70 |
| *Frankia alni* ACN14a (SEQ ID NO: 21) | Q0RBQ4 | 758 | 58 | 70 |
| *Frankia* sp. EAN1pec (SEQ ID NO: 22) | Q3WJX6 | 750 | 59 | 72 |
| *Myxococcus xanthus* strain DK 1622 (SEQ ID NO: 16) | Q1CYZ7 | 755 | 57 | 72 |
| *Saccharopolyspora erythraea* NRL 2338 (SEQ ID NO: 43) | A4FJE8 | 763 | 56 | 69 |
| *Stigmatella aurantiaca* DW4/3-1 (SEQ ID NO: 17) | Q09A24 | 704 | 55 | 67 |
| *Saccharopolyspora erythraea* NRL 2338 (SEQ ID NO: 24) | A4FGS3 | 732 | 45 | 57 |

[a] *S. scabies* chromosome, nt 2284449-2282248; Sanger Centre.
[b] Singh, B., Oh, T. J., and Sohng, J. K. Exploration of geosmin synthase from *Streptomyces peucetius* ATCC 27952 by deletion of doxorubicin biosynthetic gene cluster, *J. Ind. Microbiol. Biotechnol.* (2009); 10.1007/s10295-009-0605-0.

Table 2 lists exemplary sources of microbial contamination that may be consequent to bacterial 2-methylisoborneol synthase proteins (SEQ ID NOS.:29-32), as shown in FIGS. 13A, 13B and 13C. The methods described herein can detect any one or more of the geosmin synthases listed in Table 2 in a suspect sample.

TABLE 2

Amino acid sequence comparison of S. coelicolor SCO7700 2-methylisoborneol synthase (Q9F1Y6) with bacterial orthologs.

| Organism | UniProt ID | aa | Identity (%) | Similarity (%) |
|---|---|---|---|---|
| Streptomyces sp. Mg1 (SEQ ID NO: 29) | B4VFG0 | 314 | 83 | 89 |
| Streptomyces ambofaciens (SEQ ID NO: 31) | A3KI17 | 440 | 83 | 88 |
| Streptomyces scabies (SEQ ID NO: 30) | a | >367 | 77 | 81 |
| Streptomyces griseus (SEQ ID NO: 32) | B1VVB4 | 437 | 69 | 75 |

[a] S. scabies chromosome, nt 572020-570920; Sanger Centre.

"Suspect," as used herein in reference to a sample, refers to a sample that may be or is known to contain a microbial contamination. Suspect samples can include at least one member selected from the group consisting of a drinking (potable) water sample, an aquaculture sample, a soil sample, a slime sample, a biofilm sample and a substrate sample.

"Substrate sample," as used herein, refers to a synthetic substance or object, such as construction materials (e.g., drywall, plaster, sheet rock, brick, concrete, stone).

In an embodiment, the suspect sample is a water sample. The water sample can be from a potable water source or a non-potable water source. Water samples can be obtained from at least one member selected from the group consisting of a lake, a pond, a stream, a reservoir and a water-treatment facility.

In another embodiment, the suspect sample is an aquaculture sample. Exemplary aquaculture samples include aquaculture water samples (e.g., water from an aquaculture enclosure), aquaculture biological samples (e.g., tissues or cells of an organism raised by an aquaculture method) and whole organisms, such as fish from an aquaculture farm (e.g., salmon, trout, catfish, tilapia, cobia) and crustaceans from an aquaculture farm (e.g., shrimp, prawns, and lobsters).

The suspect sample can include a level of at least one member selected from the group consisting of geosmin (e.g., geosmin synthase nucleic acid, geosmin synthase protein), and 2-methylisoborneol (e.g., 2-methylisoborneol nucleic acid, 2-methylisoborneol synthase protein, 2-methylgeranyl diphosphate synthase nucleic acid, 2-methylgeranyl diphosphate synthase protein) that is undetectable by the olfactory (odor, smell) and gastric (taste) senses. The concentration of geosmin or 2-methylisoborneol in a suspect sample, such as a suspect sample that does not yet have an unpleasant odor consequent to geosmin and/or 2 methylisoborneol contamination, can be less than about 10.0 ng of protein per liter (ng/L), for example, at least one member selected from the group consisting of about 0.0 ng/L, about 1 ng/L, about 2.0 ng/L, about 3.0 ng/L, about 4.0 ng/L, about 5.0 ng/L, about 6.0 ng/L, about 7.0 ng/L, about 8.0 ng/L, and about 9.0 ng/L. The suspect sample can also include a concentration of geosmin and/or 2-methylisoborneol that produces an unpleasant odor, such as a level of geosmin and/or 2-methylisoborneol that is greater about 10 ng/L (e.g., at least one member selected from the group consisting of about 15 ng/L, about 20 ng/L, about 25 ng/L and about 30 ng/L). In suspect samples that have unpleasant odors, the source of the unpleasant odor in the suspect sample can rapidly and reliably be determined to be a consequence of geosmin and/or 2-methylisoborneol contamination by employing the methods of the invention.

In an embodiment, a microbial geosmin synthase (e.g., a cyanobacterial geosmin synthase) is detected. The microbial geosmin synthase that is detected can be at least one member selected from the group consisting of at least a portion of a microbial geosmin synthase nucleic acid and at least a portion of a microbial geosmin synthase protein. "At least a portion," as used herein, means any part or the entirety of an amino acid sequence or nucleic acid sequence. For example, at least a portion of a geosmin sythase can include DDHFLE (SEQ ID NO: 37), NDLFSYERE (SEQ ID NO: 76) and NEVLTSRLQQFE (SEQ ID NO: 77).

Exemplary microbial geosmin synthase nucleic acids that can be detected include at least a portion of at least one member selected from the group consisting of SEQ ID NO: 7, SEQ ID NO: 8, SEQ ID NO: 9 and SEQ ID NO: 10. Exemplary microbial geosmin synthase proteins include at least a portion of at least one member selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 43, SEQ ID NO: 78 and SEQ ID NO: 79.

In another embodiment, a microbial 2-methylisoborneol synthase (e.g., a cyanobacterial 2-methylisoborneol synthase) is detected. The microbial 2-methylisoborneol synthase can be at least a portion of at least one member selected from the group consisting of a microbial 2-methylisoborneol synthase nucleic acid and a microbial 2-methylisoborneol synthase protein.

In another embodiment, a microbial 2-methylgeranyl diphosphate synthase (e.g., a cyanobacterial 2-methylgeranyl diphosphate synthase) is detected. The microbial 2-methylgeranyl diphosphate synthase can be at least a portion of at least one member selected from the group consisting of a microbial 2-methylgeranyl diphosphate synthase nucleic acid and a microbial 2-methylgeranyl diphosphate synthase protein.

Microbial geosmin synthase nucleic acids, microbial 2-methylgeranyl diphosphate synthase nucleic acids, and microbial 2-methylisoborneol synthase nucleic acids can be detected in the suspect sample by nucleic acid amplification employing established techniques. Exemplary techniques for detecting nucleic acids in a sample are well-known in the art and include, for example, nucleic acid amplification techniques (e.g., polymerase chain reaction), in situ hybridization, Northern blot hybridization, and Southern blot hybridization (see, e.g., Sambrook, Fritsch & Maniatis, Molecular Cloning: A Laboratory Manual, Second Edition (1989) Cold Spring Harbor Laboratory Press, Cold Spring Harbor, N.Y.; F. M. Ausubel et al. (eds.), Current Protocols in Molecular Biology, John Wiley & Sons, Inc. (1994)).

The nucleic acid amplification employed to detect a geosmin synthase nucleic acid can include the use of at least one primer selected from the group consisting of TTCTTCGACGAYCACTTCC (SEQ ID NO: 1), CCCTYGTTCATGTARCGGC (SEQ ID NO: 2), AACGACCTGTTCTCCA (SEQ ID NO: 3), GCTCGATCTCATGTGCC (SEQ ID NO: 4), CTACTATTGTSAAYGAYCTVTATTC (SEQ ID NO: 5) and ATDAGSACYTATTGCAARCRGCCG (SEQ ID NO: 6). The nucleic acid amplification employed to detect a 2-methylisoborneol synthase can include use of at least one primer selected from the group consisting of SEQ ID NOS: 5, 6, 46-68 and 69.

Detection of the microbial geosmin synthase nucleic acid and/or the microbial 2-methylisoborneol synthase nucleic acid in the suspect sample by nucleic acid amplification can further include the step of sequencing the microbial geosmin synthase nucleic acid and microbial 2-methylisoborneol synthase nucleic acid. Techniques to sequence nucleic acids are known to one of skill in the art, and include techniques described herein.

A microbial geosmin synthase nucleic acid or a microbial 2-methylisoborneol synthase nucleic acid can be a deoxyribonucleic acid (e.g., genomic DNA, cDNA) or a ribonucleic acid (e.g., mRNA) that encodes a complete (e.g., full-length) microbial geosmin synthase protein or at least a portion of a microbial geosmin synthase protein, or a complete (e.g., full-length) microbial 2-methylisoborneol synthase or at least a portion of a microbial 2-methylisoborneol synthase protein. For example, a microbial geosmin synthase nucleic acid or a microbial 2-methylisoborneol synthase nucleic acid can generally be between about 50 and about 2000 nucleotides (also referred to herein as "base pairs") in length.

The microbial geosmin synthase nucleic acid that is detected in the suspect sample by nucleic acid amplification can be between about 700 nucleotides and about 750 nucleotides in length. The microbial 2-methylisoborneol synthase nucleic acid that is detected in the suspect sample by nucleic acid amplification can be between about 1100 nucleotides to about 1300 nucleotides in length.

Figure 10:
FIG. 10 depicts the biosynthetic pathway for the production of 2-methylisoborneol (MIB) in *S. coelicolor* (SCO). SCO7701 is an S-adenosyl methionine (SAM)-dependent C-methyl transferase that catalyzes the methylation of geranyl diphosphate (GPP) to produce 2-methyl-GPP. SCO7700 is a terpene synthase that catalyzes the cyclization of 2-methyl-GPP to MIB.

In an embodiment, a microbial 2-methylisoborneol synthase nucleic acid includes at least a portion of a S-adenosylmethionine (SAM)-dependent C-methyltransferase (2-methylgeranyl diphosphate synthase) nucleic acid and at least a portion of a 2-methylisoborneol synthase nucleic acid. As depicted in FIG. 10, genes encoding a SAM-dependent C-methyltransferase and a 2-methylisoborneol terpene synthase may be contiguous as a component of a two-gene operon in certain 2-methylisoborneol-producing microorganisms.

At least a portion of a microbial geosmin synthase protein or at least a portion of a microbial 2-methylisoborneol synthase protein can be detected in the methods described herein.

Suitable techniques for detecting the presence or amount of proteins in a sample are also well-known in the art and include immunological and immunochemical methods such as flow cytometry (e.g., FACS analysis), enzyme-linked immunosorbent assays (ELISA), including chemiluminescence assays, radioimmunoassay, immunoblot (e.g., Western blot) assays, and immunohistochemistry (IHC) techniques, or other suitable methods, such as mass spectroscopy. For example, antibodies to a geosmin synthase protein or a microbial 2-methylisoborneol synthase protein can be generated and used to determine the presence and/or level of these proteins in a sample, either directly or indirectly using, e.g., immunohistochemistry (IHC). Methods of producing antibodies are well-known in the art (see, e.g., Harlow et al., *Antibodies A Laboratory Manual*, Cold Spring Harbor Laboratory, 1988). The microbial geosmin synthase protein detected by the method can include $Mg^{+2}$ binding motifs, such as at least one member selected from the group consisting of DDHFLE (SEQ ID NO: 37), NDLFSYERE (SEQ ID NO: 76), NEVLTSRLQQFE (SEQ ID NO: 77), DDYFP (SEQ ID NO: 45) and NDVFSYQKE (SEQ ID NO: 75).

In another embodiment, the invention is a method of identifying a source of a microbial contamination, comprising the step of conducting a nucleic acid amplification assay in the presence of at least one member selected from the group consisting of at least one microbial geosmin primer and at least one microbial 2-methylisoborneol synthase primer on a sample obtained from a suspect source of the microbial contamination.

Exemplary nucleic acid amplification assays include various polymerase chain reaction based assays (e.g., real-time, quantitative real-time, multiplex, reverse transcriptase polymerase chain reaction assays), ligase chain reaction, self sustained sequence replication, transcriptional amplification system and Q-Beta Replicase. Products of nucleic acid amplification can be detected, for example, by labeling of the nucleic acid product during amplification, or by exposure of the product to intercalating compounds/dyes, or probes and by sequencing the nucleic acid sequences.

Suitable primers (e.g., oligonucleotide primers) for amplification of a microbial geosmin synthase nucleic acid include at least one member selected from the group consisting of SEQ ID NO: 7, SEQ ID NO: 8, SEQ ID NO: 9 and SEQ ID NO: 10.

In an embodiment, degenerate primers can be employed in the methods described herein. Degenerate primers can include mixtures of similar, not identical, primers. Exemplary degenerate primers for nucleic acid amplification of a microbial geosmin synthase nucleic acid include TTCTTCGAC-GAYCACTTCC (SEQ ID NO: 1) and CCCTYGTTCATG-TARCGGC (SEQ ID NO: 2). Exemplary degenerate primers for nucleic acid amplification of a microbial 2-methylisoborneol synthase nucleic acid include CTACTATTGT-SAAYGAYCTVTATTC (SEQ ID NO: 5) and ATDAGSA-CYTATTGCAARCRGCCG (SEQ ID NO:6).

In another embodiment, non-degenerate primers are used for nucleic acid amplification of a microbial geosmin synthase nucleic acid or a microbial 2-methylisoborneol synthase nucleic acid. Exemplary non-degenerate primers for nucleic acid amplification of a microbial geosmin synthase nucleic acid include AACGACCTGTTCTCCTA (SEQ ID NO: 3) and GCTCGATCTCATGTGCC (SEQ ID NO: 4).

"Microbial geosmin primer," as used herein, refers to nucleic acid sequences that result in the generation of at least a portion of a microbial (e.g., fungal, bacterial, algal) geosmin nucleic acid (also referred to herein as "a nucleic acid sequence encoding a geosmin synthase protein" or "a nucleic acid sequence encoding at least a portion of a geosmin synthase protein). Likewise, "Microbial 2-methyliseborneol synthase primer," as used herein, refers to nucleic acid sequences that result in the generation of at least a portion of a microbial (e.g., fungal, bacterial, algal) 2-methylisoborneol synthase nucleic acid (also referred to herein as "a nucleic acid sequence encoding a 2-methylsoborneol synthase protein" or "a nucleic acid sequence encoding at least a portion of a 2-methylisoborneol synthase protein").

Optionally, following the detection of a nucleic acid amplification product, the product can be sequenced using one of several well-known sequencing techniques (e.g., Maxam Gilbert sequencing, Sanger sequencing, dye terminator sequencing, sequencing by ligation, parallelized sequencing, sequencing by hybridization) to determine the sequence of the microbial geosmin synthase, the microbial 2-methylgeranyl diphosphate synthase, or the microbial 2-methylisoborneol synthase in the suspect sample.

In an embodiment, the method further includes the step of generating a melting curve in conjunction with the nucleic acid amplification assay to thereby produce at least one member selected from the group consisting of a microbial geosmin synthase melting curve and a microbial 2-methylisoborneol synthase melting curve.

Methods of generating nucleic acid melting curves are known in the art. For example, real time nucleic acid amplification can be performed in the presence of at least one member selected from the group consisting of at least one microbial geosmin primer and at least one microbial 2-methylisoborneol synthase primer, and, in addition, at least one nucleic acid-binding dye (e.g., SYTO9® fluorescent dye (Invitrogen)) to generate a labeled amplified product. Towards the conclusion of the nucleic acid amplification assay, a final amplification cycle can be replaced with a nucleic acid (e.g., DNA) melting analysis by subjecting the amplified product(s) to increasing temperatures (e.g., between about 75° C. and about 95° C.), with a hold step at regular temperature intervals (e.g., about 5 seconds at every whole degree Celsius) and data can be obtained at each interval.

In a particular embodiment, the nucleic acid amplification is real-time nucleic acid amplification. Real time nucleic acid amplification, also referred to a quantitative real time nucleic acid amplification, amplifies and simultaneously quantifies a microbial geosmin synthase nucleic acid and/or a microbial 2-methylisoborneol synthase nucleic acid. Such a method will permit both detection and amplification (e.g., as absolute members of copies or relative amounts when normalized to a nucleic acid standard) of a geosmin synthase nucleic acid and/or 2-methylisoborneol synthase nucleic acid in the suspect sample. In this method, the amplified microbial geosmin synthase nucleic acid and/or microbial 2-methylisoborneol synthase nucleic acid is quantified as it accumulates in the nucleic acid amplification reaction in real time after each amplification cycle.

Quantification of the microbial geosmin synthase nucleic acid or the microbial 2-methylisoborneol synthase nucleic acid can be achieved by the use of fluorescent dyes, such as SYTO9® fluorescent dye, SYBR Green®, EvaGreen®, LC Green®, BEBO®, YOYO®, YOPRO® that intercalate with the double-stranded amplified nucleic acid and/or modifying the microbial goesmin synthase nucleic acid and/or 2-methylisoborneol synthase nucleic acid probes so they fluoresce when hybridized to complementary nucleic acids. Real-time nucleic acid amplification may be combined with reverse transcription to quantify the mRNA of microbial geosmin synthase and/or 2-methylisoborneol synthase in the suspect sample.

Exemplary microbial geosmin synthase melting curves, which are indicative of contamination by geosmin-producing microorganisms (e.g., cyanobacteria), include at least one melting curve that is substantially similar to at least one member selected from the group consisting of in FIG. 6, FIG. 7, FIG. 8 and FIG. 9.

A geosmin synthase melting curve can include at least one fluorescence intensity peak between about 0.80 dF/dT to about 9.00 dF/dT in a temperature range of between about 78° C. to about 88° C., which is indicative of microbial (e.g., cyanobacterial) contamination.

In an embodiment, a geosmin synthase melting curve can include a fluorescence intensity peaks of about 3.50 dF/dT at a temperature range between about 84° C. to about 85° C. and about 4.75 dF/dT at a temperature range between about 87° C. to about 88° C., which is indicative of a *Phormidium* sp. cyanobacterial contamination.

In another embodiment, a geosmin synthase melting curve can include a fluorescence intensity peak of about 6.5 dF/dT at a temperature range between about 84° C. to about 85° C., which is indicative of a *Anabaena circinalis* cyanobacterial contamination.

In an additional embodiment, a geosmin synthase melting curve can include fluorescence intensity peaks of about 3.75 dF/dT at a temperature range between about 82° C. to about 83° C. and about 9 dF/dT at a temperature range between about 84° C. to about 86° C., which is indicative of a *Anabaena laxa* cyanobacterial contamination.

In another embodiment, a geosmin synthase melting curve can include fluorescence intensity peaks of about 0.90 dF/dT at a temperature of about 78° C., about 0.80 dF/dT at a temperature between about 84° C. to about 85° C. and about 1.2 dF/dT at a temperature between about 86° C. to about 87° C., which is indicative of a *Geitlerinema* sp. cyanobacterial contamination.

In yet another embodiment, the invention is an isolated acid comprising at least one member from the group consisting of SEQ ID NO: 7, SEQ ID NO: 8, SEQ ID NO: 9 and SEQ ID NO: 10. At least portions of SEQ ID NOS: 7-10 can be employed in the methods described herein.

In a further embodiment, the invention is an isolated polypeptide comprising at least one member selected from the group consisting of SEQ ID NO: 11, SEQ ID NO: 12, SEQ ID NO: 13, SEQ ID NO: 14 and SEQ ID NO: 15.

An additional embodiment of the invention is a method of detecting at least one member selected from the group consisting of a geosmin producing microorganism (e.g., cyanobacteria, fungi, algae) and a 2-methylisoborneol producing microorganism in a sample, comprising the steps of amplifying at least one nucleic acid in the sample in the presence of at least one member selected from the group consisting of a geosmin synthase primer (e.g., a microbial geosmin synthase primer that includes at least one primer selected from the group consisting of TTCTTCGACGAYCACTTCC (SEQ ID NO: 1), CCCTYGTTCATGTARCGGC (SEQ ID NO: 2), AACGACCTGTTCTCCTA (SEQ ID NO: 3), and GCTCGATCTCATGTGCC (SEQ ID NO: 4)) and a 2-methylisoborneol synthase primer to (e.g., a microbial 2-methylisoborneol synthase primer that includes at least one member selected from the group consisting of CTACTATTGTSAAYGAYCTVTATTC (SEQ ID NO: 5) and ATDAGSACYTATTGCAARCRGCCG (SEQ ID NO: 6)), thereby generating amplified products; and detecting at least one member selected from the group consisting of a geosmin synthase nucleic acid and a methylisoborneol synthase nucleic acid in the amplified products.

The presence of a geosmin synthase nucleic acid is indicative of a geosmin producing microorganism (e.g., cyanobacteria, fungus) in the sample and the presence of a 2-methylisoborneol synthase nucleic acid is indicative of a 2-methylisoborneol producing microorganism in the sample. Likewise, the absence of a geosmin synthase nucleic acid indicates that the sample does not include a geosmin producing microorganism and the absence of a 2-methylisoborneol synthase nucleic acid indicates that the sample does not include a 2-methylisoborneol producing microorganism.

Taste and odor episodes continue to trouble water utilities worldwide on several fronts, including management of reservoirs and consumer complaints. One of the most common consumer complaints is the detection of earthy/musty compounds, namely geosmin and/or 2-methylisoborneol (MIB). The methods and compositions described herein can be employed to rapidly improve the quality of water utilities. Humans are able to detect these compounds at extremely low levels, and detection of these compounds is often associated with a failed disinfection regime and that the water may be unsafe to drink as it is perceived to be "dirty."

Determination, at the molecular level, of the genes responsible for the production of these taste and odor compounds will provide tools to identify and better manage potential taste and odor episodes. Little is known regarding the cyanobacterial mechanisms of geosmin and MIB production and only recently has the mystery of the biosynthetic production of geosmin been unraveled in *Streptomyces* sp, with the discovery of a geosmin synthase gene. Even more recently, the proponents have successfully confirmed geosmin synthase functionality in cyanobacteria.

The methods described herein can combine the two assays (geosmin and MIB detection) (multiplex) as a screening tool for taste and odor nuisance organisms. At any given water storage the developed technology can be used, for example, to predict what preventative measures may be necessary in the short term; track the emergence of taste and odor producers in the longer term; and anticipate what trends may occur in the future.

The methods described herein provide a new nucleic acid-based detection method (microarrays, oligoprobe-based nanotechnology etc) and alternative biochemical test, such as an ELISA, to detect microbial contamination.

The detection and remediation of methylisoborneol (MIB) presents similar challenges to the water industry. This compound, which has a characteristic muddy-odor and taste, is found in a variety of actinomycete, myxobacterial, and cyanobacterial organisms, as is the case with geosmin. Much of the effort to control MIB, like geosmin, has concentrated solely on the dealing with the problem when it arises. Management options are currently limited to using activated carbon, biological filtration, oxidation, and ozonation (Ho et al., 2007, Park et al., 2007, Persson et al., 2007), with no foreseeable changes in practice.

Unlike geosmin, the mechanism of MIB production by actinomycetes and cyanobacteria has largely remained unstudied. Recently, in the myxobacterium *Nannocystis exedens*, Dickschat et al (Dickschat et al., 2007) reported incorporation of mevalonate precursors as well as methyl-labeled S-adenosylmethionine (SAM) into MIB and postulated a biosynthetic pathway in which the universal monoterpene precursor geranyl diphosphate (GPP) would undergo SAM-dependent methylation, with generation of the novel intermediate 2-methyl-GPP, which may undergo direct cyclization to MIB. Detection of 2-methylgeraniol in the volatile extract of *N. exedens*, as well as the incorporation of labeled 2-methylgeraniol into MIB, by cultures of this organism was reported.

The SCO7700 protein catalyzes the cyclization of 2-methyl-GPP to MIB (FIG. 10). The SCO7701 protein encoded by the immediately downstream gene catalyzes the SAM-dependent methylation of geranyl diphosphate to generate 2-methyl-GPP. The steady kinetic parameters ($k_{cat}$ and $K_m$) of both reactions have been determined and it has been demonstrated that incubation of GPP and SAM with both recombinant SCO7701 and SCO7700 proteins results directly in the formation of MIB. The stop codon at the 3' end of the SCO7700 gene is only 16 nt upstream of the corresponding start codon for the SCO7701 gene, with putative *Streptomyces* ribosome binding sites immediately upstream of each open reading frame.

BLAST searches have revealed the presence of homologous two-gene MIB operons in several other actinomycete species (Table 2). Highly similar terpene synthase/C-methyl transferase open reading frames can be found in MIB producing organisms including *Streptomyces griseus, Streptomyces ambofaciens, Streptomyces scabies*, and *Streptomyces* sp. Mg1. A homologous two-gene cluster may also be responsible for MIB biosynthesis in cyanobacteria.

In yet another embodiment, the invention is a kit for use in performing the methods described herein. Kits of the invention may be employed in field testing of suspect samples, such as water treatment facility samples or aquaculture samples.

Elucidation of the MIB Synthase Gene Cluster in *Pseudanabaena Limnetica* (MIB-Producer)

Degenerate primers for the *Streptomyces* MIB synthase gene cluster (e.g., see Table 3) are designed taking into account differential codon usage between *Streptomyces* and cyanobacteria. *Streptomyces* DNA has a higher GC-content (73%) compared to most other organisms and introducing redundancies at the third nucleotide in the codon triplicate will minimize issues with too many redundancy factors associated with primer design. Primers will be designed individually for SCO7700 and SCO7701 homologues, and for the entire SCO7700/SCO7701 cluster, as well as several internal gene sequences. In *Streptomyces*, the MIB synthase genes are ordered proximally, which may not be different in cyanobacteria.

TABLE 3

Sequences of degenerate primers for amplifying cyanobacterial MIB synthase genes

| Primer | Sequence (5' to 3') | |
|---|---|---|
| MIB7700_NSE_F3 | CGACCATCGTCAACGACCTCTACTC | (SEQ ID NO.: 46) |
| MIB7700_NSE_F3_MOD | CTACTATTGTSAAYGAYCTVTATTC | (SEQ ID NO.: 5) |
| MIB7700_F1 | CGGCTGATGGTCGCGGAGAA | (SEQ ID NO.: 47) |
| MIB7700_F1_MOD | CGACTVATGGTSGCWGAGAA | (SEQ ID NO.: 48) |
| MIB7700_R1 | TGCGGTGCCAGTCGTGGTTG | (SEQ ID NO.: 49) |
| MIB7700_R1_MOD | TTCGRTGCCARTCRTGGTTG | (SEQ ID NO.: 50) |
| MIB7700_F2 | TTCGACGGCTTCTCGGTGG | (SEQ ID NO.: 51) |
| MIB7700_F2_MOD | TTYGAYGGYTTCTTWGTGGG | (SEQ ID NO.: 52) |
| MIB7700_DDCYCED_F4 | GTGGACGACTGCTACTGCGAGGACC | (SEQ ID NO.: 53) |
| MIB7700_DDCYCED_F4_M | GTSGAYGAYTGYTARTGYGAAGATC | (SEQ ID NO.: 54) |
| MIB7700_NSE_R2 | GAGTTCCTTGGTGTAGGAGTAGAGG | (SEQ ID NO.: 55) |
| MIB7700_NSE_R2_MOD | BAGWTCTTTGTKTAWAASTAGAGG | (SEQ ID NO.: 56) |
| MIB7700_R3 | GGCAGGCTGTAGCGGTAGGTGT | (SEQ ID NO.: 57) |

TABLE 3-continued

Sequences of degenerate primers for amplifying cyanobacterial MIB synthase genes

| Primer | Sequence (5' to 3') | |
|---|---|---|
| MIB7700_R3_MOD | GGBAGWCTKTATCGVTAGGTGT | (SEQ ID NO.: 58) |
| MIB7701_PCR_F1 | GAGGGAGTGACCCTGTCCG | (SEQ ID NO.: 59) |
| MIB7701_PCR_F1_MOD | GAAGGTGTCACTCTBTCCG | (SEQ ID NO.: 60) |
| MIB7701_PCR_R3 | GAAGTGGGCGTTGATCTGG | (SEQ ID NO.: 61) |
| MIB7701_PCR_R3_MOD | AAARTGWGCRTTTATCTGG | (SEQ ID NO.: 62) |
| MIB7701_GGGFOLD_R1_M | TCACCATWAANCCNCCTCGAGGGCA | (SEQ ID NO.: 63) |
| MIB7701_PCR_F2 | GACGCCGTACCAGGAGG | (SEQ ID NO.: 64) |
| MIB7701_PCR_F2_MOD | GACTCCGTAYCAYGAGG | (SEQ ID NO.: 65) |
| MIB7701_PCR_R4 | CCGGGAGTGGATGTTGC | (SEQ ID NO.: 66) |
| MIB7701_PCR_R4_MOD | YCCNGARTGRATGTTGC | (SEQ ID NO.: 67) |
| MIB7701_R2 | ATCAGGACGTACTGGAAGGAGCCGT | (SEQ ID NO.: 68) |
| MIB7701_R2_MOD | ATDAGSACYTATTGCAARCRGCCG | (SEQ ID NO.: 6) |
| MIB7701_GGGFOLD_R1 | TGACCATGGAACCGCCGCGTCCGCA | (SEQ ID NO.: 69) |

A vectorette approach of genome walking (FIG. 11) will be run after initial attempts of degenerate PCR. First described in 1991 (Arnold and Hodgson, 1991), it offers advantages over conventional DNA library construction in terms of time, efficiency, and screening options. Unlike conventional screening of libraries using Southern Hybridization probes to detect similar sequences, the vectorette approach involves:

1. Digesting DNA with several restriction enzymes
2. Using a primer anchored on a known sequence within the target gene
3. Ligation of the digested product with a "vectorette" of known sequence
4. Performing PCR
5. Sequencing the product Degenerate PCR can be employed to generate sequence data that can be used to design the specific internal anchoring primers, or primers can be designed for the SCO7700 terpene synthase gene around the DDCYCED (SEQ ID NO: 35) and NSE motifs or the characteristic GXGXG (SEQ ID NO: 36)-Rossmann fold of the SCO7701 C-methyl transferase gene. Several other highly conserved regions within these genes also occur, and provide several other options. Selected PCR products from either degenerate PCR or the vectorette approach will be sequenced by conventional methods to confirm identity before being used for further work described herein.

In addition, a cosmid library for use in Southern Hybridization can be employed, to yield suitable leads for the MIB synthase gene cluster. Methods for cosmid library preparation are well established but require considerable time for preparation of cultures and the extraction of good quality DNA.

The library will be screened for suitable clones and constructs using probes generated from the SCO7700, SCO7701, and SCO7701+7700 genes using standard methods, as described herein. Positive "hits" of clones will be further investigated by restriction enzyme digests, agarose gel electrophoresis, and Southern hybridization with subsequent sequencing of positive bands.

Once the gene sequences are confirmed, each gene will be ligated into a protein expression vector (e.g. pEt 21d(+) or pEt-28) using standard methods. The ligated insert/vector will be transformed into E. coli XL1 Blue competent cells and the insert confirmed again by sequencing for sequence fidelity and orientation. The expression vector will then be transformed into the tightly regulated E. coli BL21 (DE3) pLysS protein expression host system. Each gene will be induced by standard methods to generate the corresponding recombinant protein carrying, as appropriate, N- or C-terminal His6-Tag affinity sequences, and the protein sizes will be confirmed by SDS-PAGE against standard protein markers.

Both the cyanobacterial C-methyltransferase and the terpene synthase will be purified to homogeneity using standard methods developed for the corresponding S. coelicolor proteins (for example, immobilized metal-affinity chromatography using Ni(2+) or Co(3+) and His6-Tag proteins, followed, as necessary, by ion exchange on Q-Sepaharose, hydrophobic interaction chromatography on butyl-Sepharose, and/or gel filtration on an ÄKTA Rapid Protein Purification System. The actual molecular mass of each protein will be determined directly by Matrix-Assisted Laser Desorption/Ionization, Time-of-Flight (MALDI-TOF) mass spectrometry (Brown University, Department of Chemistry). The expected size of the cyanobacterial ortholog of the Streptomyces C-methyltransferase SCO7701 is about 33 KDa, while the MIB synthase (terpene cyclase) corresponding to SCO7700 will be about 48 KDa.

The enzyme activity of each of the purified recombinant P. limnetica proteins will be established using the assays already developed for the corresponding S. coelicolor enzymes. Thus, the SCO7701 homolog (C-methyltransferase) will be incubated with GPP and SAM. The resultant product will be treated with a mixture of a pyrase and alkaline phosphatase and the liberated 2-methylgeraniol will be directly identified by capillary GC-MS comparison with an authentic sample. Similarly, synthetic 2-methylgeranyl diphosphate (2-MeGPP) will be incubated with the recombinant terpene P.

*limnetica* homolog of SCO7700 and formation of the resultant methylisoborneol (MIB) confirmed by direct GC-MS comparison with an authentic sample. These same assays can be used to verify the predicted biochemical activity of homologous 2-MeGPP synthase and MIB synthase cloned from additional cyanobacterial species. A combined incubation of GPP and SAM will be carried out with both recombinant *P. limnetica* proteins, with GC-MS analysis of the pentane-soluble extract to confirm the formation of MIB.

Using established methods, the steady-state kinetic parameters, $k_{cat}$ and $K_m$ will be determined for both *P. limnetica* proteins. For the C-methyltransferase, the recently developed coupled UV-assay reported by Dorgan et al (Dorgan et al., 2006) will be used, in which the initially generated co-product, S-adenosylhomocysteine, normally a potent inhibitor of SAM-dependent methyl transferases, is converted in situ to S-ribosylhomocysteine and adenine by recombinant S-adenosylhomocysteine/5'-methylthioadenosine nucleosidase (SAHN/MTAN, EC 3.2.2.9). Subsequently, adenine generated from AdoHcy is further hydrolyzed to hypoxanthine and ammonia by recombinant adenine deaminase (EC 3.5.4.2). This deamination is associated with a decrease in absorbance at 265 nm that can be monitored continuously. For the MIB synthase, [$^{1-3}$H]2-MeGPP can be used as a substrate and the standard terpene synthase assay liquid scintillation assay of pentane soluble [$^3$H]methylisoborneol. Alternatively, using unlabeled 2-MeGPP, formation of inorganic pyrophosphate can be directly monitored using the coupled chemiluminescence assay originally developed by Lahser et al for RNA and DNA polymerases (Lahser and Malcolm, 2004).

Nucleic acid amplification will be designed using sequences aligned from *Pseudanabaena limnetica* and other MIB-producing *Streptomyces*. Multiple strategies will be employed:

1. PCRs for C-methyl transferase (entire gene and smaller internal fragments)
2. PCRs for terpene synthase (entire gene and smaller internal fragments)
3. PCRs for combined C-methyl transferase/terpene synthase Methyl transferases are relatively common in cyanobacteria and may differ between the methyl transferases involved in the MIB synthase cluster and other methyl transferases, and similarly for terpene synthases. Given that the two genes of the cyanobacterial MIB operon, the C-methyl transferase and the terpene synthase, may be adjacent to one another as they are in the various *Actinomyces* species.

The Australia Water Quality Centre has a large cyanobacterial culture collection obtained from a wide geographical distribution that will provide numerous isolates to challenge the specificity of the PCRs. PCRs will be run and electrophoretic bands of the expected size will be excised, purified, reamplified, and cloned into TOPO® cloning system for sequencing. Sequence data will be collated, aligned and suitable real-time PCR assays will be designed.

Having verified both the MIB and geosmin synthase PCRs, they will be combined into a multiplex format to create a quantitative "taste and odor real-time PCR," that will form the basis for tests described herein. The multiplex PCR will be designed for both a lab based diagnostic test and for a portable PCR platform that will enable this technology to be used in the field.

The taste and odor PCR will be tested using environmental samples in the following ways:

1. screening of implicated taste and odor isolates
2. monitoring taste and odor episodes in nuisance reservoirs The mechanisms involved in the production of these taste and odor compounds are not well understood. Globally, there has been increased production of these compounds by blooms in reservoirs and the incidences of such events appears to be on the increase, possibly due to global warming and increased human impacts on water quality. Understanding the mechanisms behind this phenomenon would provide information for managing these severe water quality incidents in water resources.

The invention described herein develops and applies new tools to track the growth and decline of natural cyanobacterial bloom populations in reservoirs in order to develop an understanding of the regulation of production of geosmin and/or MIB in waters, which will increase an understanding of genetic and physiological control of geosmin production in the longer term to develop predictive models of the production of these problem contaminants in drinking water.

The identification of the genetic machinery for taste and odor producing cyanobacteria will provide a fundamental step forward. Gene sequences will also provide the starting point for the understanding of the expression and regulation of these genes in the natural environment. In addition, expression of the proteins involved would allow the future development of antibodies directed against these enzymes that could be used in an alternative biochemical test, such as an ELISA.

The invention described herein will also be of value to the freshwater aquaculture industry, which currently experiences loss of farmed fish due to tainting of flesh with geosmin and/or MIB (Martin et al., 1991, Van der Ploeg and Boyd, 1991, Schrader and Dennis, 2005). Estimated losses to U.S. farmers are in the vicinity of about $60 million per annum (Schrader et al., 2003). The potential for screening of fish ponds for nuisance algae; therefore, would be a valuable monitoring and management tool for this industry also.

REFERENCES

ARNOLD, C. & HODGSON, I. J. (1991) Vectorette PCR: a novel approach to genomic walking PCR Methods Appl, 1, 39-42.

BENTLEY, R. & MEGANATHAN, R. (1981) Geosmin and methylisoborneol biosynthesis in streptomycetes. Evidence for an isoprenoid pathway and its absence in non-differentiating isolates. FEBS Lett, 125, 220-2.

BOWMER, K. H., PADOVAN, A., OLIVER, R. L., KORTH, W. & GANF, G. G. (1992) Physiology of Geosmin production by *Anabaena circinalis* isolated from the Murrumbidgee river, Australia. Wat Sci Tech, 25, 259-267.

CANE, D. E., HE, X., KOBAYASHI, S., OMURA, S. & IKEDA, H. (2006) Geosmin biosynthesis in *Streptomyces avermitilis*. Molecular cloning, expression, and mechanistic study of the germacradienol/geosmin synthase. J Antibiot (Tokyo), 59, 471-9.

CANE, D. E. & WATT, R. M. (2003) Expression and mechanistic analysis of a germacradienol synthase from *Streptomyces coelicolor* implicated in geosmin biosynthesis. Proc Natl Acad Sci USA, 100, 1547-51.

COOK, D., NEWCOMBE, G. & SZTAJNBOK, P. (2001) The application of powdered activated carbon for MIB and geosmin removal: predicting PAC doses in four raw waters. Water Res, 35, 1325-33.

DICKSCHAT, J. S., BODE, H. B., MAHMUD, T., MULLER, R. & SCHULZ, S. (2005) A novel type of geosmin biosynthesis in myxobacteria. J Org Chem, 70, 5174-82.

DICKSCHAT, J. S., NAWRATH, T., THIEL, V., KUNZE, B., MULLER, R. & SCHULZ, S. (2007) Biosynthesis of the off-flavor 2-methylisoborneol by the myxobacterium *Nannocystis exedens*. Angew Chem Int Ed Engl, 46, 8287-90.

DORGAN, K. M., WOODERCHAK, W. L., WYNN, D. P., KARSCHNER, E. L., ALFARO, J. F., CUI, Y., ZHOU, Z. S. & HEVEL, J. M. (2006) An enzyme-coupled continuous spectrophotometric assay for S-adenosylmethionine-dependent methyltransferases. Anal Biochem, 350, 249-55.

GAGNE, F., RIDAL, J., BLAISE, C. & BROWNLEE, B. (1999) Toxicological effects of geosmin and 2-methylisoborneol on rainbow trout hepatocytes. Bulletin of Environmental Contamination and Toxicology, 63, 174-180.

GERBER, N. N. (1979) Volatile substances from actinomycetes: their role in the odor pollution of water. CRC Crit Rev Microbiol, 7, 191-214.

GERBER, N. N. & LECHEVALIER, H. A. (1965) Geosmin, an earthly-smelling substance isolated from actinomycetes. Appl Microbiol, 13, 935-8.

GIGLIO, S., JIANG, J., SAINT, C. P., CANE, D. E. & MONIS, P. T. (2008) Isolation and characterization of the gene associated with geosmin production in cyanobacteria. Environ Sci Technol, 42, 8027-32.

GIGLIO, S., MONIS, P. T. & SAINT, C. P. (2005) Legionella confirmation using real-time PCR and SYTO9 is an alternative to current methodology. Appl Environ Microbiol, 71, 8944-8.

GUST, B., CHALLIS, G. L., FOWLER, K., KIESER, T. & CHATER, K. F. (2003) PCR-targeted *Streptomyces* gene replacement identifies a protein domain needed for biosynthesis of the sesquiterpene soil odor geosmin. Proc Natl Acad Sci USA, 100, 1541-6.

HAYES, K. & BURCH, M. (1989) Odorous compounds associated with algal blooms in South Australian waters. Wat Res, 23, 115-121.

HAYES, S. J., HAYES, K. & ROBINSON, B. S. (1991) Geosmin as an odorous metabolite in cultures of a free-living amoeba, *Vannella* species (Gymnamoebia, Vannellidae). J Protozool, 38, 44-47.

HO, L., HOEFEL, D., BOCK, F., SAINT, C. P. & NEWCOMBE, G. (2007) Biodegradation rates of 2-methylisoborneol (MIB) and geosmin through sand filters and in bioreactors. Chemosphere, 66, 2210-8.

IZAGUIRRE, G., HWANG, C. J., KRASNER, S. W. & MCGUIRE, M. J. (1982) Geosmin and 2-methylisoborneol from Cyanobacteria in three water supply systems. Appl Environ Microbiol, 43, 708-714.

IZAGUIRRE, G., TAYLOR, W. D. & PASEK, J. (1999) Off-flavor problems in two reservoirs, associated with planktonic *Pseudanabaena* species. Water Science and Technology, 40, 85-90.

JIANG, J. & CANE, D. E. (2008) Geosmin biosynthesis. Mechanism of the fragmentation-rearrangement in the conversion of germacradienol to geosmin. J Am Chem Soc, 130, 428-9.

JIANG, J., HE, X. & CANE, D. E. (2006) Geosmin Biosynthesis. *Streptomyces coelicolor* Germacradienol/Germacrene D Synthase Converts Farnesyl Diphosphate to Geosmin. J Am Chem Soc, 128, 8128-9.

JIANG, J., HE, X. & CANE, D. E. (2007) Biosynthesis of the earthy odorant geosmin by a bifunctional *Streptomyces coelicolor* enzyme. Nat Chem Biol, 3, 711-5.

KEEGAN, A. R., FANOK, S., MONIS, P. T. & SAINT, C. P. (2003) Cell culture-Taqman PCR assay for evaluation of *Cryptosporidium parvum* disinfection. Appl Environ Microbiol, 69, 2505-11.

KOMATSU, M., TSUDA, M., OMURA, S., OIKAWA, H. & IKEDA, H. (2008) Identification and functional analysis of genes controlling biosynthesis of 2-methylisoborneol. Proc Natl Acad Sci USA, 105, 7422-7.

LAHSER, F. C. & MALCOLM, B. A. (2004) A continuous nonradioactive assay for RNA-dependent RNA polymerase activity. Anal Biochem, 325, 247-54.

LLOYD, S. W. & GRIMM, C. C. (1999) Analysis of 2-methylisoborneol and geosmin in catfish by microwave distillation—solid-phase microextraction. J Agric Food Chem, 47, 164-9.

MARTIN, J. F., IZAGUIRRE, G. & WATERSTRAT, P. (1991) A planktonic *Oscillatoria* species from Mississippi catfish ponds that produces the off-flavour compound 2-methylisoborneol. Water Res, 25, 1447-1451.

MCGUIRE, M. J. (1995) Off-flavour as the consumers measure of drinking water safety. Wat Sci Tech, 31, 1-8.

NAES, H., AARNES, H., UTKILEN, H. C., NILSEN, S. & SKULBERG, O. M. (1985) Effect of photon fluence rate and specific growth rate on geosmin production of the cyanobacterium *Oscillatoria brevis* (Kutz.) Gom. Appl Environ Microbiol, 49, 1538-1540.

NAES, H. & POST, A. F. (1988) Transient stages of geosmin, pigments, carbohydrates and proteins in continous cultures cultures if *Oscillatoria brevis* induced by changes in notrogen supply. Arch Microbiol, 150, 333-337.

PARK, G., YU, M., GO, J., KIM, E. & KIM, H. (2007) Comparison between ozone and ferrate in oxidising geosmin and 2-MIB in water. Water Sci Technol, 55, 117-25.

PERSSON, F., HEINICKE, G., HEDBERG, T., HERMANSSON, M. & UHL, W. (2007) Removal of geosmin and MIB by biofiltration—an investigation discriminating between adsorption and biodegradation. Environ Technol, 28, 95-104.

RASMUSSEN, J. P., SAINT, C. P. & MONIS, P. T. (2007) Use of DNA melting simulation software for in silico diagnostic assay design: targeting regions with complex melting curves and confirmation by real-time PCR using intercalating dyes. BMC Bioinformatics, 8, 107.

ROBINSON, B. S., MONIS, P. T. & DOBSON, P. J. (2006) Rapid, sensitive, and discriminating identification of *Naegleria* spp. by real-time PCR and melting-curve analysis. Appl Environ Microbiol, 72, 5857-63.

SAADOUN, I. M., SCHRADER, K. K. & BLEVINS, W. T. (2001) Environmental and nutritional factors affecting geosmin synthesis by *Anabaena* sp. Water Res, 35, 1209-18.

SCHNURER, J., OLSSON, J. & BORJESSON, T. (1999) Fungal volatiles as indicators of food and feeds spoilage. Fungal Genet Biol, 27, 209-17.

SCHRADER, K. K. & DENNIS, M. E. (2005) Cyanobacteria and earthy/musty compounds found in commercial catfish (*Ictalurus punctatus*) ponds in the Mississippi Delta and Mississippi—Alabama Blackland Prairie. Water Res, 39, 2807-14.

SCHRADER, K. K., NANAYAKKARA, N. P., TUCKER, C. S., RIMANDO, A. M., GANZERA, M. & SCHANEBERG, B. T. (2003) Novel derivatives of 9,10-anthraquinone are selective algicides against the musty-odor cyanobacterium *Oscillatoria perornata*. Appl Environ Microbiol, 69, 5319-27.

SCHULZ, S., FUHLENDORFF, J. & REICHENBACH, H. (2004) Identification and synthesis of volatiles released by the myxobacterium *Chondromyces crocatus*. Tetrahedron, 60, 3863-3872.

SUGIURA, N., IWAMI, N., INAMORI, Y., NISHIMURA, O. & SUDO, R. (1998) Significance of attached cyanobacteria relevant to the occurrence of musty odor in Lake Kasumigaura. Water Research, 32, 3549-3554.

UTKILEN, H. C. & FROSHAUG, M. (1992) Geosmin production and excretion in a planktonic and benthic *Oscillatoria*. Wat Sci Tech, 25, 199-206.

VAN BREEMEN, L. W. C. A., DITS, J. S. & KETELAARS, H. A. M. (1992) Production and reduction of geosmin and 2-methylisoborneol during storage of river water in deep reservoirs. Wat Sci Tech, 25, 233-240.

VAN DER PLOEG, M. & BOYD, C. E. (1991) Geosmin production by Cyanobacteria (Blue-green algae) in fish ponds at Auburn, Ala. Journal of the World Aquaculture Society, 22, 207-216.

VAN DER PLOEG, M., TUCKER, C. S. & BOYD, C. E. (1992) Geosmin and 2-methylisoborneol production by cyanobacteria in fish ponds in the southeastern united states. Wat Sci Tech, 25, 283-290.

WANG, C. M. & CANE, D. E. (2008) Biochemistry and molecular genetics of the biosynthesis of the earthy odorant methylisoborneol in *Streptomyces coelicolor*. J Am Chem Soc, 130, 8908-9.

WATSON, S. B. (2003) Cyanobacterial and eukaryotic algal odour compounds: signals or by-products? A review of their biological activity. Phycologia, 42, 332-350.

The teachings of all of the references cited herein are hereby incorporated by reference in their entirety.

EXEMPLIFICATION

Geosmin is a secondary metabolite responsible for earthy tastes and odors in potable water supplies. Geosmin continues to be a challenge to water utility management regimes and remains one of the most common causes of consumer complaints, as the taste of "dirty" water may suggest a failed disinfection regime and that the water may be unsafe to drink. Although cyanobacteria have been reported to be largely responsible for these taste and odor events, the answer as to how or why geosmin is produced has been elusive. Described herein is the mechanism by which geosmin is produced in a model cyanobacterium, *Nostoc punctiforme* PCC 73102 (ATCC 29133), in which it has been demonstrated that a single enzyme is utilized to catalyze the cyclization of farnesyl diphosphate to geosmin. Using this information, a PCR-based assay has been developed that allows the rapid detection of geosmin-producing cyanobacteria. This test may be utilized to confirm and track the emergence of taste and odor-producing cyanobacteria in any given water body and thus can be used as an early warning system by managers of water bodies that may suffer from adverse taste and odor episodes.

Globally, cyanobacteria are nuisance organisms in fresh water supplies and have been primarily responsible for taste and odor episodes as well as toxic incidents (1-4). Consumer taste and odor complaints to water utilities are high, and are second only to those concerning chlorinous taints. One of the commonest complaints, that of an "earthy" or musty odor, is largely a result of geosmin and/or 2 methylisoborneol (MIB) produced by cyanobacteria. The human taste and odor sensitivity threshold for geosmin is an extraordinarily low about 10 ng/L (10 ppt) (5) and, although geosmin has no known adverse side effects, consumers associate the detection of this compound with poorly treated water that might be unsafe to drink. The detection and management of these geosmin-producing cyanobacteria is therefore of paramount importance to water utilities. Currently, the only options to deal with this issue are dosing water bodies with environmentally unfriendly chemicals such as copper sulfate in order to control algal blooms, as well as the use of powdered activated carbon in water treatment plants to remove the responsible taste and odor compounds. Biological filtration using aged sand filters may represent a suitable alternative to remove these undesired compounds (6).

The volatile metabolite geosmin is produced by a wide range of microorganisms, including most species of *Streptomyces* and a variety of other actinomycetes, myxobacteria and cyanobacteria, as well as certain fungi and selected higher plants such as liverworts and beets. Although geosmin was first identified by Gerber in 1965 (7), the biochemical pathway of geosmin production remained obscure for many years. In 1981, Bentley first proposed that geosmin was likely a degraded sesquiterpene, based on the observed incorporation of labeled acetate by cultures of *Streptomyces* antibioticus (8). Within the last several years, however, the mechanism of geosmin biosynthesis in *Streptomyces* and myxobacteria (9-11) has been elucidated in detail.

Despite earlier confusion as to how many enzymes were involved, and indeed if the mechanism of geosmin production was different in different organisms, it is now known that in *S. coelicolor* A3(2) a single 726-amino acid protein, encoded by the 2181-bp SCO6073 gene (cyc2) (12,13), catalyzes the $Mg^{2+}$-dependent cyclization of farnesyl diphosphate (FPP), the universal acyclic precursor of all sesquiterpenes, to a mixture of geosmin and the sesquiterpene alcohol germacradienol, accompanied by smaller amounts of the bicyclic hydrocarbons germacrene D and 8,10-dimethyl-1-octalin (14-17) (FIG. 1). The *S. coelicolor* geosmin/germacradienol synthase is in fact a bifunctional enzyme in which both the N-terminal and C-terminal halves show a high degree of sequence similarity to the well-studied 336-amino acid sesquiterpene synthase, pentalenene synthase (16). Experiments with individually expressed recombinant proteins corresponding to the N-terminal and C-terminal domains have shown that the N-terminal half of the synthase catalyzes the cyclization of FPP to a 85:15 mixture of germacradienol and germacrene D, accompanied by traces of the octalin, while the C-terminal domain catalyzes the $Mg^{2+}$-dependent cyclization—fragmentation of germacradienol to geosmin, with release of the 2-propanol side chain as acetone (14,16). Site-directed mutagenesis experiments have confirmed that the N- and C-terminal domains each harbor catalytically independent active sites (16).

It has also been shown that the closely related GeoA (SAV2163) protein of *S. avermitilis* (about 78% sequence identity and about 85% similarity) catalyzes the same biochemical reaction (18), while more than a dozen known or presumed geosmin synthases deduced from a variety of *Streptomyces, Frankia, Saccharopolyspora*, and myxobacterial genome sequences share correspondingly high levels of sequence conservation over all about 730 to about 740 amino acids (about 45 to about 75% identity, about 57 to about 85% similarity). In all these proteins, the N-terminal region contains two strictly conserved motifs, a, DDHFLE (SEQ ID NO: 37) sequence, typically about 80 to about 100 amino acids, from the N-terminus and a ND(L/I)FSY(Q/E)RE (SEQ ID NO: 38) motif about 140-amino acids downstream, corresponding to the universally conserved aspartate-rich DDXXD (SEQ ID NO: 39) motif and NSE triad (N/D)DXX(S/T)XXXE (SEQ ID NO: 40), respectively, that are found in all sesquiterpene synthases and that are known to be involved in the binding of the essential cofactor $Mg^{2+}$ (19,20). Similarly the C-terminal half of geosmin synthase has a canonical variant of the aspartate rich motif, DDYYP (SEQ ID NO: 41), as well as a downstream ND(V/I/L)FSYQKE (SEQ ID NO: 42) variant of the NSE triad.

Following the initial biochemical characterization of the SCO6073 gene (13) and its implication in geosmin biosynthesis (12), Ludwig et al (21) reported the use of PCR to isolate homologous genes from an environmental geosmin-producing *Phormidium* sp. that were similar in sequence both to SCO6073 and SAV2163. Although they demonstrated that these genes were expressed in the parent cyanobacteria and speculated on the possibility of a "geosmin operon", they did not directly correlate the expression with geosmin production nor did they explicitly demonstrate that these genes were functionally responsible for geosmin production in the *Phormidium* isolate examined.

The npun02003620 gene in the reported genome sequence of the cyanobacterium *Nostoc punctiforme* PCC 73102 (ATCC 29133), encodes a hypothetical protein ZP_00109187 with about 55% amino acid sequence similarity to the N-terminal region of SCO6073, including the presence of the universally conserved DDHFLE (SEQ ID NO: 37) and NDLFSYQRE (SEQ ID NO: 44) motifs characteristic of this class of enzyme. The predicted protein, however, consists of only 630 amino acids, about 100 amino acids shorter than the SCO6073 protein or any other known or predicted geosmin synthase. Equally importantly, although the C-terminal half of ZP_00109187 also is predicted to harbour a typical DDYFP (SEQ ID NO: 45) motif, the essential NSE triad is apparently absent.

The model cyanobacterium *Nostoc punctiforme* PCC 73102 (ATCC 29133) was examined first and the hypothetical protein ZP_00109187 encoded by npun02003620 was demonstrated to be, in fact, a truncated protein that, while catalyzing the conversion of FPP to germacradienol, is incapable of supporting geosmin formation. The apparent truncation has been shown to be the result of a single, but critical, sequencing error in the published DNA sequence and that the corrected open reading frame corresponds to a fully functional geosmin synthase, dubbed NPUNMOD, that is of similar length and sequence to the *S. coelicolor* SCO6073 enzyme and all other geosmin synthase proteins. Having established the identity and biochemical function of the *Nostoc* geosmin synthase gene, this information was utilized to design a PCR-based diagnostic tool for the detection of geosmin-producing cyanobacteria. Collectively, these results provide the fundamental step forward for understanding taste and odor episodes and provide a powerful tool that can be used to predict whether an emerging cyanobacterial bloom will be a geosmin producer and assist in designing strategies to limit its effects in the short term; track the emergence of taste and odor producers in the longer term; and anticipate what trends may occur in the future.

Culture of Cyanobacteria and DNA Extraction

*Nostoc punctiforme* PCC 73102 (ATCC 29133), a known geosmin producer, was maintained in ATCC medium #819 according to the provided product information sheet. The following geosmin- and 2-methylisoborneol (MIB)-producing isolates, confirmed by GC-MS, were a generous gift from G. Izaguirre: *Pseudoanabaena limnetica* (MIB producer), *Anabaena laxa* (geosmin producer), *Nostoc* sp. UTAH12-18b (geosmin producer), and *Phormidium calcicola* (geosmin and MIB producer). GC-MS of additional environmental isolates used in this study were performed using fresh cultures of cyanobacteria (not normalized for cell number). The above isolates were grown in BG-11 medium and maintained under standard conditions at 25° C. Before DNA extraction, cultures were subcultured on starch-casein agar for the detection of possible contaminating geosmin-producing actinomycete bacteria. All subcultures were negative for actinomycete organisms. DNA was extracted using the Qiagen DNA Mini Spin kit according to manufacturer's instructions, using 1 ml of cyanobacterial culture, with the addition of an overnight proteinase K incubation at about 56° C.

Cloning and Expression of npun020003620 and NPUNMOD Proteins, Incubation with Farnesyl Pyrophosphate, and GC-MS Analysis The DNA sequence corresponding to npun020003620 was amplified using the primers npunstart1 (5'-ATTTTATC-CATGGTTATGCAACCCTTTGAACTGCCAGAA-3') (SEQ ID NO.:70) and npunhalt1 (5'-TAATAACTCGAGT-TATGGATTTCGCCCTCG-3') (SEQ ID NO.:71), while the full length natural NPUNMOD gene was amplified with primers npunstart1 and npunhalt4 (5'-TAATAACTCGAG-TAATTGACCGAGTAATGAC-3') (SEQ ID NO.:72), inserting NcoI and XhoI restriction sites (underlined) for the npunstart1 and npunhalt primers respectively. Fragments were PCR-amplified using proofreading Elongase Taq polymerase (Invitrogen) as described by the manufacturer, using 35 cycles consisting of 94° C. for 30 s, 55° C. for 30 s, and 68° C. for 120 s, with a final hold at 4° C. until needed. The products were digested with NcoI and XhoI (Promega, USA) and ligated into a similarly digested pET21d(+) expression vector (Novagen). The previously described protocols for propagation, expression, and purification of recombinant *S. coelicolor* geosmin synthase were followed for the ZP_00109187 and NPUNMOD proteins (12, 14), except that transformants were induced with 1 mM IPTG for 2 h at 35° C.

Successful transformants were sequenced using Big Dye Terminator sequencing. Recombinant ZP_00109187 protein, which did not carry a His6-tag, was obtained in soluble form, while the initially generated recombinant NPUNMOD protein, carrying a C-terminal His6-tag, was obtained as insoluble inclusion bodies that could not be resolubilized in active form despite the use of a wide variety of re-folding conditions. To remove the His6-tag, a stop codon was introduced by site directed mutagenesis using the QuikChange® Site-Directed Mutagenesis Kit (Stratagene, USA) using the mutagenic primers NPM2_58-notag (5'-TTACTCGGT-CAATGATTACTCGAGCAC-3') (SEQ ID NO.:73) and NPM2_58-notaga (5'-GTGCTCGAGTAATCATTGAC-CGAGTAA-3') (SEQ ID NO.:74) (stop codon in bold, XhoI restriction sites underlined). The sequence of NPM2-58-pB32 was confirmed by resequencing (University of California, Davis Sequencing Facility, Davis, Calif., USA).

Protein expression from *E. coli* BL21(DE3)pLysS once again gave insoluble inclusion bodies that could not be properly solubilized under a variety of denaturation—refolding conditions. Therefore, the NPM2-58 protein was co-expressed along with the chaperone protein combination GroES/GroEL by co-transformation of the two plasmids, NPM2-58-pJJ32 (ampicillin-resistant) and pGro12 (kanamycin-resistant) into *E. coli* BL21(DE3)pLysS, selecting a single colony displaying ampicillin-kanamycin-chloramphenicol multiresistance. Cells from this colony were used to inoculate LB broth containing 100 µg/ml ampicillin, 50 µg/mlkanamycin and 34 µg/ml chloramphenicol (LBAKC) and the overnight culture was transferred to 500 ml of LBAKC broth and incubated at 37° C. and 250 rpm for 2 h. Chaperone expression was induced by addition of arabinose to a final concentration of 4 mg/ml and the desired protein expression was then induced by addition of IPTG to a final concentration of 0.4 mM. Incubation was continued for an additional 18 h at 18° C., 250 rpm. The cells were harvested by centrifugation and resuspended in 30 ml of lysis buffer (20 mM Tris-HCl, 10% glycerol, 0.1 mM DTT, pH 8.0). The cells were disrupted by sonication and the cell lysate was clarified by centrifugation.

The supernatant was purified by 12% ammonium sulfate precipitation followed by purification on a 25-ml n-butyl-Sepharose column that had been pre-equilibrated in buffer A (0.5 M ammonium sulfate, 50 mM NaH$_2$PO$_4$, 0.1 mM DTT, pH 7.0). After loading of the supernatant onto the column, the resin was washed with 60 ml of buffer A followed by a 180-ml linear gradient from buffer A to buffer B (50 mM NaH$_2$PO$_4$, 0.1 mM DTT, pH 7.0). The purified protein eluted in buffer B as a 1:1 mixture with chaperone protein, as determined by SDS-PAGE. The apparent molecular weight (Mr) of 82 kDa of the desired protein is very close to the theoretical MW 85 kDa. Incubation of the purified protein, free of all contaminating proteins, with FPP and subsequent GC-MS analysis were performed using the procedures described by Jiang et al (15).

Geosmin Synthase PCR, Cloning of PCR Products and Sequencing

Geosmin synthase PCR (G-PCR1) mastermix consisted of 2.5 mM MgCl$_2$, 1×PCR buffer, 200 μM dNTP, 300 μM each of forward primer 250F (5'-TTCTTCGACGAYCACTTCC-3') (SEQ ID NO.:1) and reverse primer 971R (5'-CCCTYGT-TCATGTARCGGC-3') (SEQ ID NO.:2), 5% dimethyl sulphoxide, 1 U of Platinum Taq DNA polymerase (Invitrogen), and 2 μl of extracted cyanobacterial DNA. Reactions were run on a Perkin Elmer 2400 thermal cycler with an initial denaturation step of about 95° C. for 5 min, followed by 55 cycles of about 95° C. for 30 s, about 55° C. for 30 s, and about 72° C. for 120 s, with a final extension step of 10 min at about 72° C. Samples were then run on a 1% agarose gel with 10 μl of SYBR Safe (Invitrogen) for 45 min at 80V and bands were visualized using a Dark reader transilluminator (Clare Chemical Research, Dolores, Colo., USA). For selected sample bands of expected size (743 bp), DNA was extracted using a Qiagen Qiaquick Gel extraction kit according to the manufacturer's instructions. The purified PCR product was then cloned into vector PCR 2.1 TOPO® according to the manufacturer's instructions (TOPO cloning kit, Invitrogen), and subsequently sequenced using Big Dye Terminator sequencing reactions.

A second geosmin synthase PCR (G-PCR2) was developed for real time PCR screening of other cyanobacterial DNA samples. Reactions were first optimized by standard thermal cycling as described above, and then 2.5 μM SYTO9 (Invitrogen) was incorporated into the mastermix. Primers used for G-PCR2 were: 288AF (5'-AACGACCTGTTCTCCTA-3') (SEQ ID NO.:3), and 288AR (5'-GCTCGATCTCATGT-GCC-3') (SEQ ID NO.:4), generating an amplicon of 288 bp. Real time PCR was performed using a Corbett Research Rotorgene 6000HRM (Corbett Research, Australia) under the same conditions as above, except that the final extension step was replaced with a DNA melting analysis from about 75 to about 95° C., with data being acquired every degree with a 5 s hold at each step. All data were acquired on the "Green" channel, with excitation at 470 nm and emission at 510 nm.

Results and Discussion

Demonstration of Geosmin Synthase in the Model Cyanobacterium *Nostoc Punctiforme*

The reported 1893-bp npun02003620 gene of *Nostoc punctiforme* PCC 73102 (ATCC 29133), currently annotated as encoding a hypothetical protein (ZP_00109187), has 55% amino acid sequence similarity to the N-terminal region of both known geosmin synthases, *S. coelicolor* A3(2) SCO6073 and *S. avermitilis* SAV2163, thereby suggesting the likely biochemical function of this cyanobacterial gene may be similar to the N-terminal mediated reactions of the reported *Streptomyces*. The reported open reading frame is, however, about 300 bp shorter than either the SCO6073 or SAV2163 gene or any of the homologous Actinomycete and myxobacterial geosmin synthase genes. The predicted ZP_00109187 protein also lacks the essential NSE triad in the C-terminal domain that is found in all other geosmin synthases as well as in all other known terpene synthases. To assess the biochemical function of the reported npun020003620 open reading frame, recombinant ZP_00109187 protein was generated based on the start and stop codons predicted by the deposited sequence, resulting in a 71 KDa protein of the expected size as determined by SDS-PAGE, which was named NJ2 (GenBank Accession No. FJ010202).

Incubation of recombinant NJ2 with FPP yielded a mixture of germacradienol (94%) and germacrene D (6%) accompanied by a trace of the octalin, but without any detectable geosmin according to the standard GC-MS analysis. The generation of germacradienol indicates that the N-terminal half of the NJ2 protein has been properly folded and has the expected germacradienol/germacrene D synthase activity, consistent with the demonstrated properties of the homologous N-terminal domain of *S. coelicolor* SCO6073 geosmin synthase. On the other hand, the absence of geosmin production is consistent with the apparent truncation of the C-terminal domain and the absence of a functional active site for geosmin formation. Indeed the biochemical properties of the recombinant Nostoc NJ2 protein are similar to those of the previously reported truncated mutant derived from the N-terminal half of *S. coelicolor* geosmin synthase, as well as variants of full-length SCO6073 protein carrying mutations in the essential C-terminal DDYYP or NSE triad regions, all of which could convert FPP to germacradienol and germacrene D but were completely defective in geosmin formation.

Figure 3:
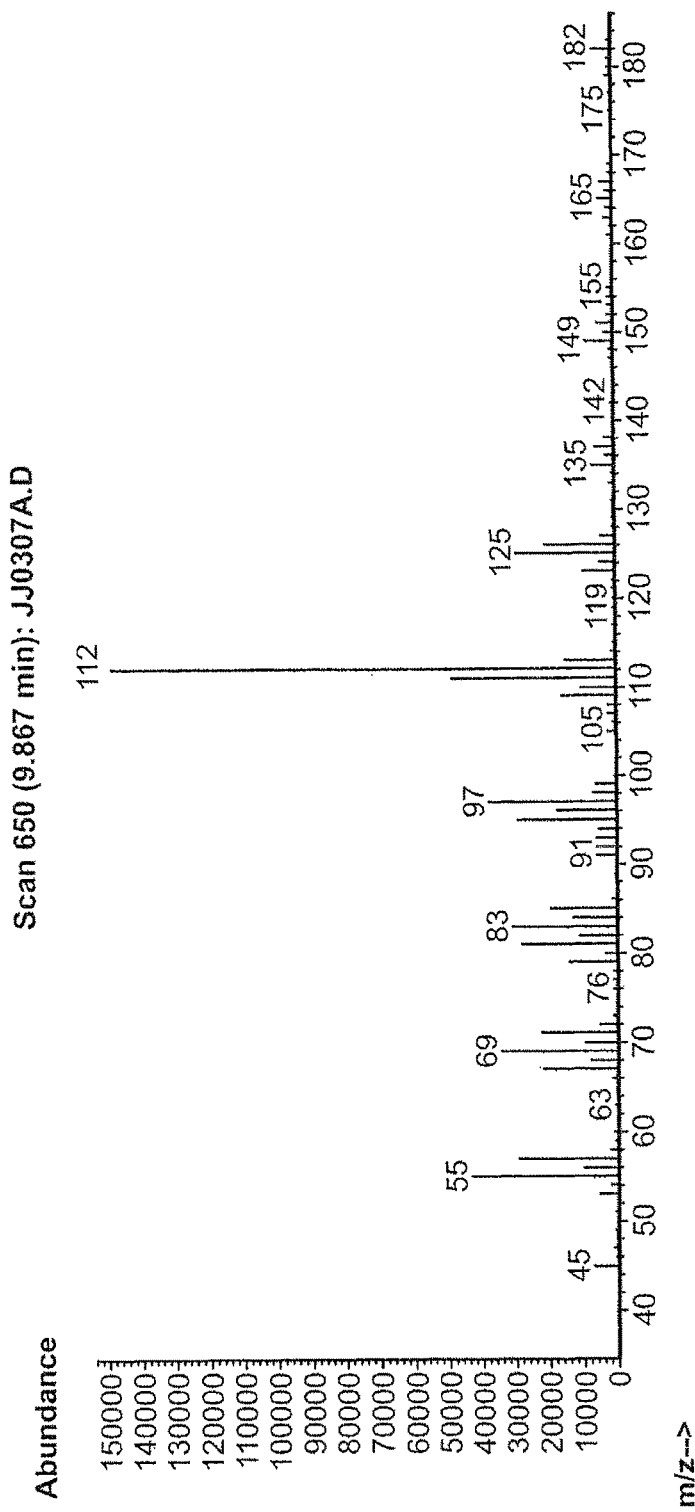
FIG. 3 depicts a mass spectrum of geosmin produced in the incubation of FPP with recombinant NPUNMOD protein, the geosmin synthase of *Nostoc punctiforme*.
Figure 4:
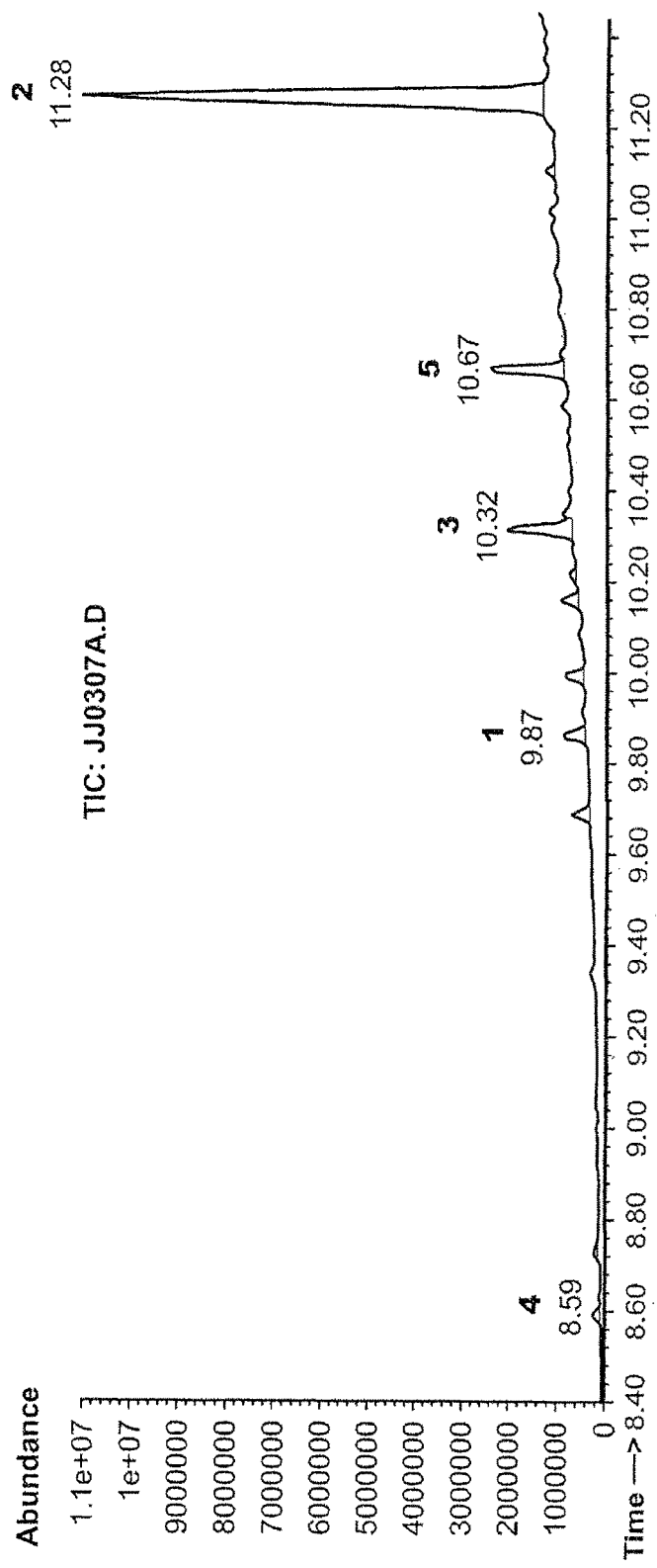
FIG. 4 depicts a GC-MS trace of geosmin produced in the incubation of FPP with recombinant NPUNMOD protein, showing geosmin (1), along with coproducts germacradienol (2), germacrene D (3), octalin (4), and (E)-Nerolidol (5).
Figure 6:
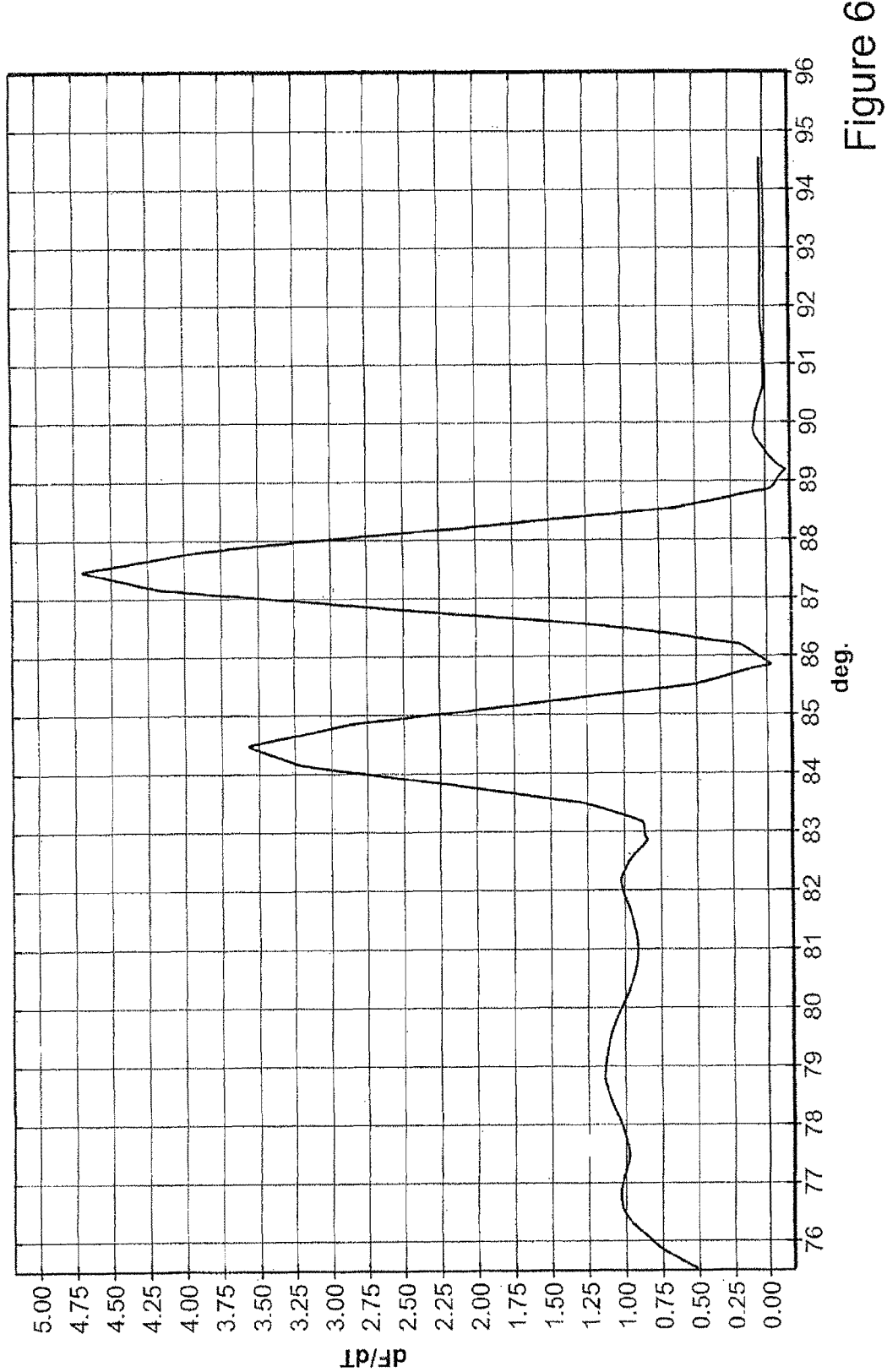
FIG. 6 depicts a melting curve of a *Phormidium* sp. geosmin synthase real time PCR product.
Figure 7:
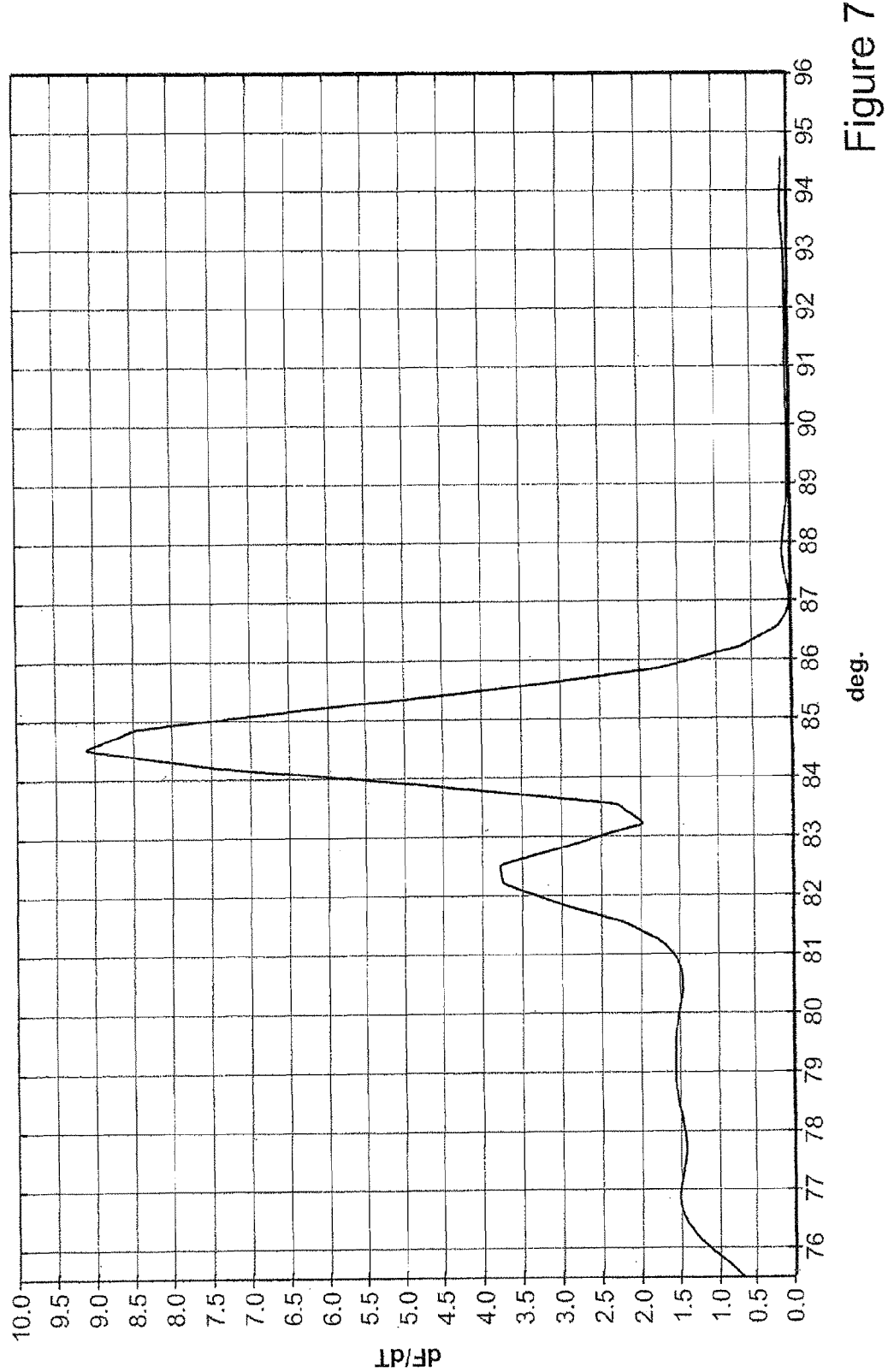
FIG. 7 depicts a melting curve of a *Anabaena laxa* geosmin synthase real time PCR product.
Figure 8:
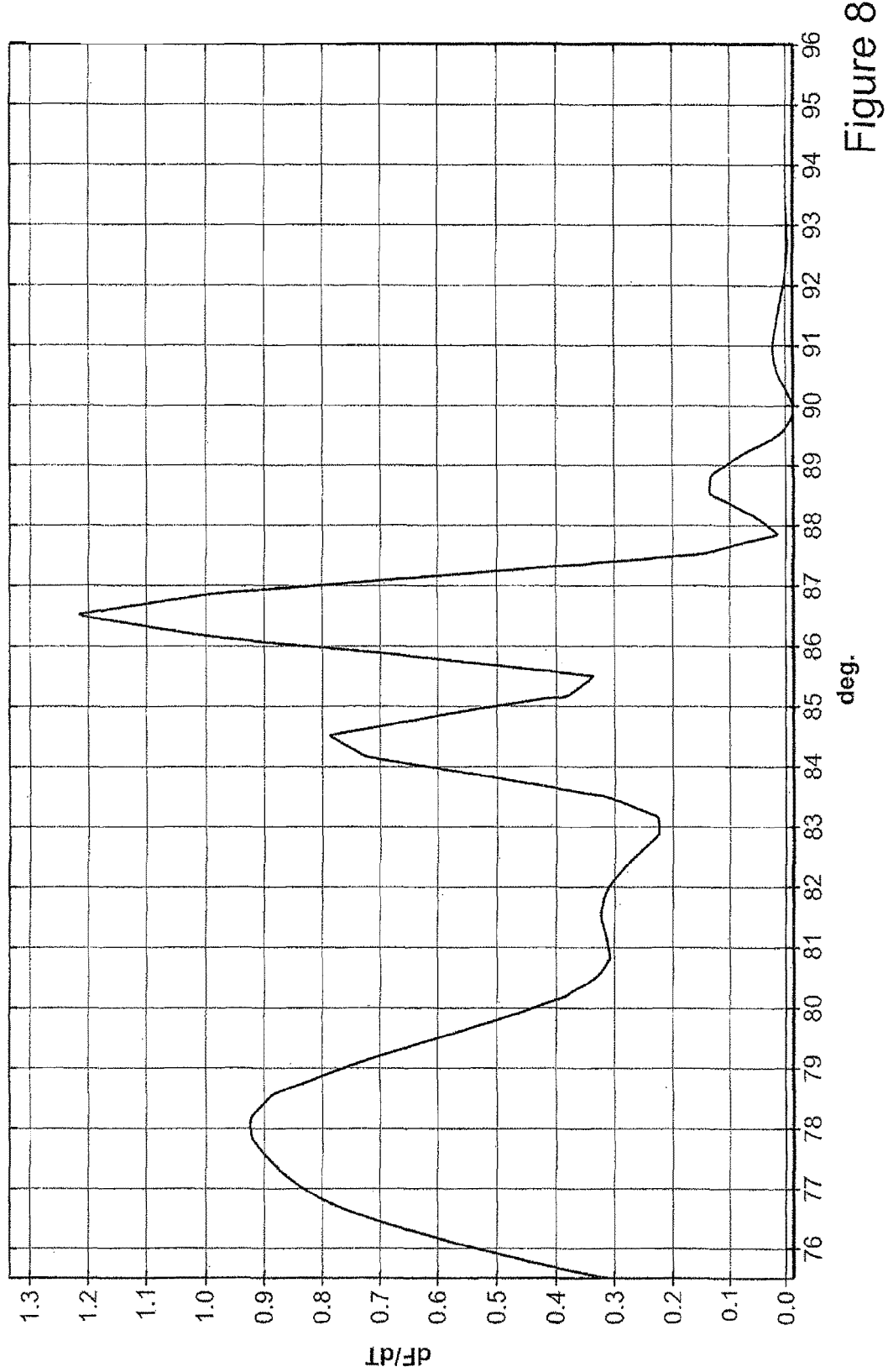
FIG. 8 depicts a melting curve of a *Geitlerinema* geosmin synthase real time PCR product.
Figure 9:
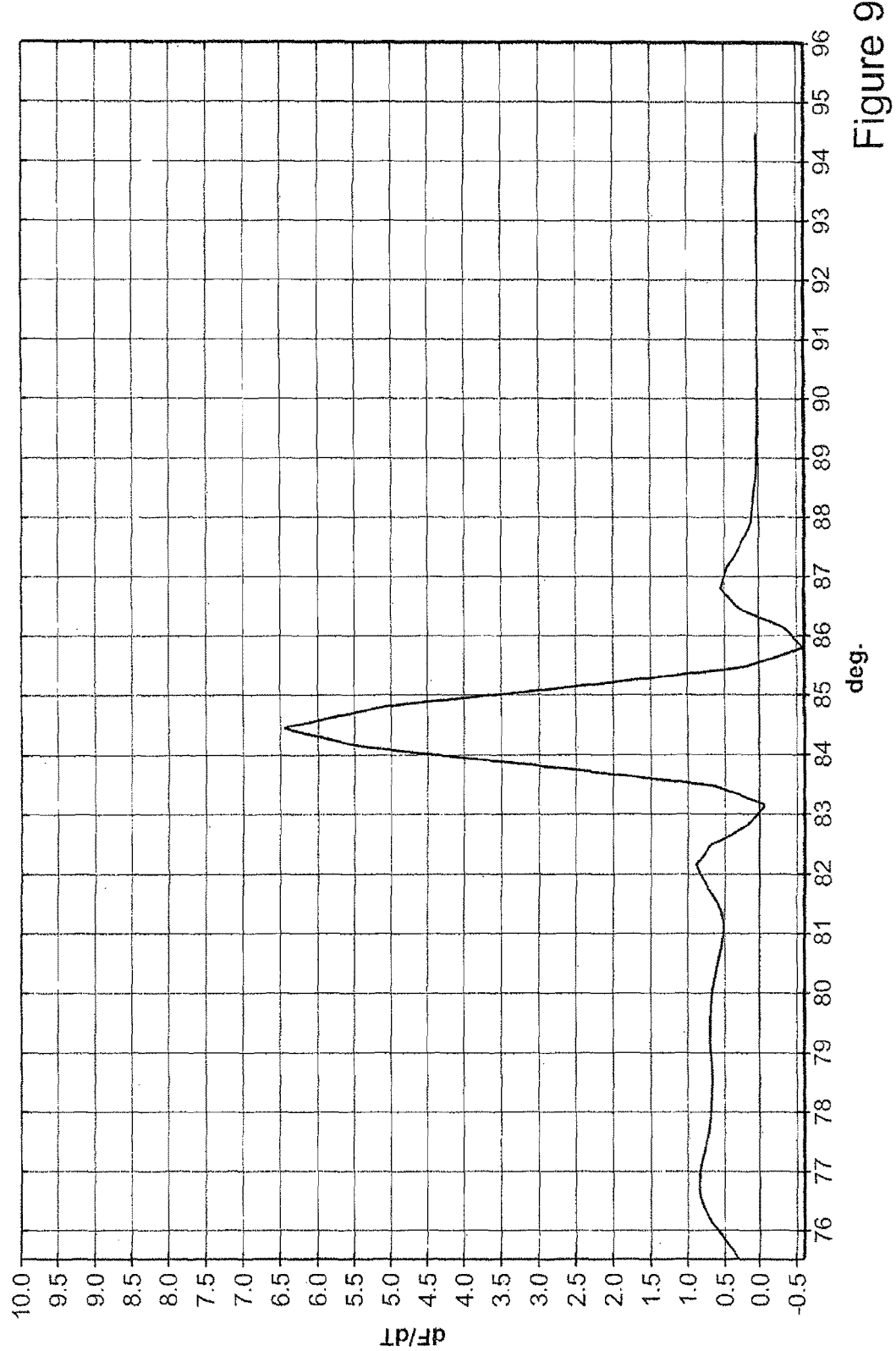
FIG. 9 depicts a melting curve of a *Anabaena circinalis* geosmin synthase real time PCR product.

Comparison of the experimentally determined DNA sequence of the 3'-region of the PCR-amplified NJ2 construct with the published npun02003620 sequence revealed that the sequence recorded in the *Nostoc punctiforme* genome database contains an extra "T" nucleotide at position 33677, resulting in a false frame shift with the predicted insertion of the isoleucine at amino acid position 616, as well as a premature stop codon after amino acid 630 of the deduced protein ZP_00109187. Excluding this extraneous T nucleotide relieves the implied frame shift and eliminates the erroneous stop codon. The corrected open reading frame encodes an additional 126 amino acids, corresponding to a predicted length of 756 amino acids (85 kDa) (GenBank Accession No. FJ010203). Importantly, the full-length C-terminal domain of the corrected protein sequence, termed NPUNMOD, now has the universally conserved DDYFP (SEQ ID NO.:45) and NDVFSYQKE (SEQ ID NO.:75) motifs that are found in the *Streptomyces* geosmin synthases SCO6073 and SAV2163 (FIG. 2) as well as all other Actinomycete and myxobacterial orthologs (GenBank accession FJ010202 and FJ010203 for NJ2 and NPUNMOD). Although the PCR-amplified DNA sequence encoding recombinant NJ2 does retain the C-terminal NSE triad just before the C-terminus, the premature truncation presumably prevents proper assembly of the active site of the C-terminal half of the geosmin synthase Recombinant full-length NPUNMOD protein was shown to be a fully functional geosmin synthase by incubation with FPP under the standard conditions. GC-MS analysis of the hexane-soluble extract confirmed the formation of a typical product mixture consisting of geosmin (4%), germacradienol (78%), germacrene D (8%), and octalin (1%) as well (E)-nerolidol (9%) (FIGS. 3A and 3B). The formation of nerolidol is unusual and may result from some degree of improper folding of the recombinant geosmin synthase or by chaperone-mediated solvolysis of FPP.

Development of a Geosmin Synthase Screening Tool

The corrected, full-length geosmin synthase gene of *Nostoc punctiforme*, was employed to develop a PCR-based screening procedure to evaluate the presence of geosmin synthase genes in other cyanobacterial strains. A pair of partially degenerate primers and G-PCR1 were used to amplify the target geosmin synthase genes of several cyanobacterial isolates that were directly confirmed as geosmin producers by GC-MS. The PCR primers were designed so that the forward 250F primer sequence would be anchored on the conserved aspartate-rich motif of the N-terminal domain while the 971R reverse primer flanked the NSE triad region normally found 140 amino acids downstream of the aspartate-rich motif. Using this procedure, 743-bp DNA fragments were amplified from geosmin-producing *Anabaena laxa, Nostoc* sp. UTAH12-18b, and *Phormidium calcicola*, while the diagnostic fragment was absent in the geosmin non-producing organism *Pseudoanabaena limnetica*. Positive PCR products were cloned and sequenced as described earlier. All positive amplicons encoded the strictly conserved $Mg^{2+}$-binding motifs, DDHFLE (SEQ ID NO: 37 and NDLFSYQRE (SEQ ID NO: 44, that are found in the N-terminal domain of all geosmin synthases (FIG. 5).

A rapid real-time PCR (G-PCR2) for screening cyanobacterial isolates was developed, using primers internal to the G-PCR1 products. Seventeen isolates were screened using the PCR assay described herein, which was run in parallel with GC-MS analyses of isolate suspensions. Table 4 demonstrates that G-PCR2 is able to detect additional isolates of *Phormidium, Anabaena*, and *Geitlerinema* sp, all of which were GC-MS positive for geosmin. Moreover, the real-time G-PCR2 protocol did not amplify DNA from any GC-MS geosmin-negative isolates such as *Planktothrix, Oscillatoria*, and *Pseudoanabaena* sp. indicating that the presence of a geosmin synthase gene is invariably associated with geosmin production by the host, thereby validating the utility of the real-time PCR gene detection as a reliable diagnostic assay for cyanobacterial geosmin producers.

TABLE 4

Comparison of a geosmin synthase PCR assay and GC-MS analysis using environmental cyanobacterial isolates

| Isolate | Origin | GEOSMIN (ng/L) | G-PCR2 |
|---|---|---|---|
| *Oscillatoria* LM603 | Lake Matthews, USA | <2 | − |
| *Oscillatoria* | Hope Valley, SA | <2 | − |
| *Oscillatoria* | Hope Valley, SA | <2 | − |
| *Phormidium* sp | Happy Valley, SA | 112 | + |
| *Phormidium* sp | Happy Valley, SA | 21 | + |
| *Phormidium* sp | Happy Valley, SA | 4 | + |
| *Phormidium* sp | Happy Valley BR, SA | 47 | + |
| *Phormidium* sp | Happy Valley, SA | 67 | + |
| *Phormidium* sp | Happy Valley, SA | 553 | + |
| *Planktothrix* sp DVL1003C | Diamond Valley, USA | <2 | − |
| *Anabaena circinalis* ANA346B | Myponga, SA | 152 | + |
| *Pseudoanabaena* sp | Happy Valley, SA | <2 | − |
| *Pseudoanabaena* sp | Happy Valley, SA | <2 | − |
| *Geitlerinema* | Little Para, SA | 3113 | + |
| *Phormidium* 007D | Hope Valley, SA | 198 | + |
| *Phormidium* 005E | Hope Valley, SA | 60 | + |
| *Phormidium* 012G | Hope Valley, SA | 21 | + |

The use of G-PCR2 and melting curve analysis has the additional advantage of differentiating among geosmin-producing species. In this PCR protocol, the positive *Geitlerinema, Phormidium*, and *Anabaena* species produce different characteristic melting profiles (FIGS. 6-9). For example, *Anabaena circinalis* gives rise to a single peak with a melting temperature (Tm) of about 84.5° C., while *Anabaena laxa* has a more complex melting pattern with two Tms; one at about 84.5° C. and another at about 82.3° C. A similarly complex melting pattern is seen for all *Phormidium* sp, with Tms at about 84.5 and about 87.5° C. and also for *Geitlerinema* that has Tms at about 84.5 and about 86.5° C. The use of melting curve analysis for species identification and genotyping is becoming increasingly popular, especially with the availability of Tm prediction software such as POLAND and MELTSIM (22). Furthermore, the observation of differential Tms from a single primer pair has been used elsewhere to characterise several *Naegleria* isolates in a diagnostic setting (23). The combination of real-time PCR for detection of geosmin synthase genes and Tm analysis may be particularly useful.

In conclusion, the production of geosmin in cyanobacteria has been demonstrated to be due to the presence of a single gene encoding the geosmin synthase enzyme. In addition, a diagnostic geosmin synthase PCR protocol has been developed that can be a valuable tool for use by water utilities in the detection of organisms responsible for geosmin production in any given water body. The flexibility and portability of real-time PCR equipment has previously been used to track toxic cyanobacteria in the field (24) and, therefore, it is foreseeable that this technology may be used for mobile monitoring of geosmin-producing cyanobacteria and assistance with current dosing protocols by pinpointing specific problem areas to increase the efficacy of treatment. The quantification of the abundance of geosmin synthase genes in a water body may become a valuable input into predictive modelling of water storages when coupled with chemical, physical, and physiochemical values, and the methods described herein may be used to predict the occurrence of taste and odor episodes before they become an operational problem.

The geosmin synthase gene in cyanobacteria may be employed to explore key regulatory mechanisms controlling geosmin production as a function of life-cycle and environmental conditions is now also possible, which may provide insight into strategies to better control the production of geosmin in water storages and eliminate the need to use environmentally controversial control methods such as copper sulfate dosing. Control and mitigation of taste and odor episodes is a frustratingly common event for water utilities and it is foreseeable that the tools described herein may be used as an adjunct to current monitoring programs to help better engineer a timely response to potential water management.

1. Burlingame, G. A.; Dann, R. M.; Brock, G. L., A case study of geosmin in Philadelphia's water. Journal AWWA 1986, (Management and operations), 56-61.
2. Carmichael, W. W.; Li, R., Cyanobacteria toxins in the Salton Sea. Saline Systems 2006, 2, 5.
3. Izaguirre, G.; Taylor, W. D., Geosmin and 2-methylyisoborneol production in a major aqueduct system. Wat Sci Tech 1995, 31, 41-48.
4. van Apeldoorn, M. E.; van Egmond, H. P.; Speijers, G. J.; Bakker, G. J., Toxins of cyanobacteria. Mol Nutr Food Res 2007, 51, 7-60.
5. Cook, D.; Newcombe, G.; Sztajnbok, P., The application of powdered activated carbon for MIB and geosmin removal: predicting PAC doses in four raw waters. Water Res 2001, 35, 1325-1333.

6. Ho, L.; Hoefel, D.; Bock, F.; Saint, C. P.; Newcombe, G., Biodegradation rates of 2-methylisoborneol (MIB) and geosmin through sand filters and in bioreactors. Chemosphere 2007, 66, 2210-2218.
7. Bentley, R.; Meganathan, R., Geosmin and methylisoborneol biosynthesis in streptomycetes. Evidence for an isoprenoid pathway and its absence in non-differentiating isolates. FEBS Lett. 1981, 125, 220-222.
8. Dickschat, J. S.; Bode, H. B.; Mahmud, T.; Muller, R.; Schulz, S., A novel type of geosmin biosynthesis in myxobacteria. J. Org. Chem. 2005, 70, 5174-5182.
9. Dickschat, J. S.; Wenzel, S. C.; Bode, H. B.; Muller, R.; Schulz, S., Biosynthesis of volatiles by the myxobacterium *Myxococcus xanthus*. Chembiochem 2004, 5, 778-787.
10. Schulz, S.; Fuhlendorff, J.; Reichenbach, H., Identification and synthesis of volatiles released by the myxobacterium *Chondromyces crocatus*. Tetrahedron 2004, 60, 3863-3872.
11. Gerber, N, N, Lechavalier, H. A., Geosmin, an earthy smelling substance isolated from actinomyces. Appl microbiol 1956, 13(6), 935-938.
12. Gust, B.; Challis, G. L.; Fowler, K.; Kieser, T.; Chater, K. F., PCR-targeted *Streptomyces* gene replacement identifies a protein domain needed for biosynthesis of the sesquiterpene soil odor geosmin. Proc. Natl. Acad. Sci. USA 2003, 100, 1541-1546.
13. Cane, D. E.; Watt, R. M., Expression and mechanistic analysis of a germacradienol synthase from *Streptomyces coelicolor* implicated in geosmin biosynthesis. Proc. Natl. Acad. Sci. USA 2003, 100, 1547-1551.
14. Jiang, J.; Cane, D. E., Geosmin biosynthesis. Mechanism of the fragmentation-rearrangement in the conversion of germacradienol to geosmin. J Am Chem Soc 2008, 130, 428-429.
15. Jiang, J.; He, X.; Cane, D. E., Geosmin Biosynthesis. *Streptomyces coelicolor* Germacradienol/Germacrene D Synthase Converts Farnesyl Diphosphate to Geosmin. J. Am. Chem. Soc. 2006, 128, 8128-8129.
16. Jiang, J.; He, X.; Cane, D. E., Biosynthesis of the earthy odorant geosmin by a bifunctional *Streptomyces coelicolor* enzyme. Nat Chem Biol 2007, 3, 711-715.
17. Nawrath, T.; Dickschat, J. S.; Muller, R.; Jiang, J.; Cane, D. E.; Schulz, S., Identification of (8S,9S,10S)-8,10-Dimethyl-1-octalin, a Key Intermediate in the Biosynthesis of Geosmin in Bacteria. J. Am. Chem. Soc. 2008, 130, 430-431.
18. Cane, D. E.; He, X.; Kobayashi, S.; Omura, S.; Ikeda, H., Geosmin biosynthesis in *Streptomyces avermitilis*. Molecular cloning, expression, and mechanistic study of the germacradienol/geosmin synthase. J. Antibiot. (Tokyo) 2006, 59, 471-479.
19. Christianson, D. W., Structural biology and chemistry of the terpenoid cyclases. Chem. Rev. 2006, 106, 3412-3442.
20. Komatsu, M.; Tsuda, M.; Omura, S.; Oikawa, H.; Ikeda, H., Identification and functional analysis of genes controlling biosynthesis of 2-methylisoborneol. Proc. Natl. Acad. Sci. USA 2008, 105, 7422-7427.
21. Ludwig, F.; Medger, A.; Bornick, H.; Opitz, M.; Lang, K.; Gottfert, M.; Roske, I., Identification and expression analyses of putative sesquiterpene synthase genes in *Phormidium* sp. and prevalence of geoA-like genes in a drinking water reservoir. Appl Environ Microbiol 2007, 73, 6988-6993.
22. Rasmussen, J. P.; Saint, C. P.; Monis, P. T., Use of DNA melting simulation software for in silico diagnostic assay design: targeting regions with complex melting curves and confirmation by real-time PCR using intercalating dyes. BMC Bioinformatics 2007, 8, 107.
23. Robinson, B. S.; Monis, P. T.; Dobson, P. J., Rapid, sensitive, and discriminating identification of *Naegleria* spp. by real-time PCR and melting-curve analysis. Appl Environ Microbio12006, 72, 5857-5863.
24. Rasmussen, J. P.; Giglio, S.; Monis, P. T.; Campbell, R. J.; Saint, C. P., Development and field testing of a real-time PCR assay for cylindrospermopsin-producing cyanobacteria. J Appl Microbiol 2008, 104, 1503-15.

The teachings of all patents, published applications and references cited herein are incorporated by reference in their entirety.

EQUIVALENTS

While this invention has been particularly shown and described with references to example embodiments thereof, it will be understood by those skilled in the art that various changes in form and details may be made therein without departing from the scope of the invention encompassed by the appended claims.

---

What is claimed is:

1. A method of detecting a geosmin producing microorganism and a 2-methylisoborneol producing microorganism in a sample, comprising the steps of:
   a) amplifying nucleic acids in the sample in the presence of at least one geosmin synthase nucleic acid primer and at least one 2-methylisoborneol synthase nucleic acid primer to thereby generate amplified products; and
   b) detecting a geosmin synthase nucleic acid and a methylisoborneol synthase nucleic acid in the amplified products,
   whereby the presence of the geosmin synthase nucleic acid and the 2-methylioborneol synthase nucleic acid in the amplified products detects the geosmin producing microorganism and the 2-methylisoborneol producing microorganism in the sample.

2. The method of claim 1, further including the step of sequencing the amplified products.

3. The method of claim 1, wherein the microbial 2-methylisoborneol synthase is detected.

4. The method of claim 1, wherein the microbial 2-methylisobomeol synthase primer nucleic acid includes a primer for amplifying at least a portion of at least one member selected from the group consisting of a S-adenosylmethionine-dependent C-methyltransferase nucleic acid (2-methylgeranyl diphosphate synthase) and a terpene synthase nucleic acid.

5. The method of claim 1, wherein the sample includes at least one member selected from the group consisting of a potable water sample, an aquaculture sample and a substrate sample.

6. The method of claim 1, wherein the source of microbial contamination includes less than about 10 ng microbial geosmin per liter and less than about 10 ng microbial 2-methylisoborneol per liter.

7. The method of claim 1, wherein the geosmin producing microorganism and the 2-methylisoborneol producing microorganism in the sample is consequent to the presence of at least one cyanobacteria species selected from the group consisting of *Phormidium* sp., *Phormidium calcicola*, *Anabaena circinalis*, *Anabaena laxa*, *Geirlerinema* sp., *Nostoc punctiforme*, *Nostoc* sp., *Pseudoanabaena limnetica*, *Pseudanabaena* sp., *Oscillatoria* sp., *Lyngbya* sp., *Planktothrix* sp., *Tyconema* sp., *Hyella* sp., *Anabaena* sp, and *Aphanizomenon* sp.

8. The method of claim 1, further including the steps of:
   a) amplifying nucleic acids in the sample in the presence of at least one microbial 2-methylgeranyl diphosphate synthase nucleic acid primer to thereby generate amplified products; and
   b) detecting a microbial 2-methylgeranyl diphosphate synthase nucleic acid in the amplified products,
   whereby the presence of the geosmin synthase nucleic acid, the 2-methylioborneol synthase nucleic acid and the microbial 2-methylgeranyl diphosphate synthase nucleic acid in the amplified products detects the geosmin producing microorganism and the 2-methylisoborneol producing microorganism in the sample.

9. The method of claim 1, wherein the geosmin synthase primer includes at least one member selected from the group consisting of SEQ ID NOS. 1-10.

10. The method of claim 1, wherein the 2-methylisobomeol synthase primer includes at least one member selected from the group consisting of SEQ ID NOS. 5, 6, 46-68 and 69.

* * * * *

UNITED STATES PATENT AND TRADEMARK OFFICE
CERTIFICATE OF CORRECTION

PATENT NO. : 8,535,883 B2  Page 1 of 1
APPLICATION NO. : 13/048407
DATED : September 17, 2013
INVENTOR(S) : David Cane et al.

It is certified that error appears in the above-identified patent and that said Letters Patent is hereby corrected as shown below:

In the Claims

In Column 127, Claim 4, line 47, delete "ylisobomeol" and insert --ylisoborneol--

In Column 128, Claim 10, line 56, delete "isobomeol" and insert --isoborneol--

Signed and Sealed this
Twenty-fourth Day of December, 2013

Margaret A. Focarino
*Commissioner for Patents of the United States Patent and Trademark Office*

UNITED STATES PATENT AND TRADEMARK OFFICE
CERTIFICATE OF CORRECTION

| | | |
|---|---|---|
| PATENT NO. | : 8,535,883 B2 | Page 1 of 1 |
| APPLICATION NO. | : 13/048407 | |
| DATED | : September 17, 2013 | |
| INVENTOR(S) | : David Cane et al. | |

It is certified that error appears in the above-identified patent and that said Letters Patent is hereby corrected as shown below:

In the Specification

Column 1, Line 16, replace the existing paragraph with the following paragraph:
--This invention was made with government support under grant number R01 GM030301 awarded by the National Institutes of Health. The government has certain rights in the invention.--

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 79

<210> SEQ ID NO 1
<211> LENGTH: 19
<212> TYPE: DNA
<213> ORGANISM: Unknown
<220> FEATURE:
<223> OTHER INFORMATION: Degenerate oligonucleotide primer

<400> SEQUENCE: 1
ttcttcgacg aycacttcc                                               19

<210> SEQ ID NO 2
<211> LENGTH: 19
<212> TYPE: DNA
<213> ORGANISM: Unknown
<220> FEATURE:
<223> OTHER INFORMATION: Degenerate oligonucleotide primer
```

```
<400> SEQUENCE: 2
ccctygttca tgtarcggc                                              19

<210> SEQ ID NO 3
<211> LENGTH: 16
<212> TYPE: DNA
<213> ORGANISM: Unknown
<220> FEATURE:
<223> OTHER INFORMATION: Degenerate oligonucleotide primer

<400> SEQUENCE: 3
aacgacctgt tctcca                                                 16

<210> SEQ ID NO 4
<211> LENGTH: 17
<212> TYPE: DNA
<213> ORGANISM: Unknown
<220> FEATURE:
<223> OTHER INFORMATION: Degenerate oligonucleotide primer

<400> SEQUENCE: 4
gctcgatctc atgtgcc                                                17

<210> SEQ ID NO 5
<211> LENGTH: 25
<212> TYPE: DNA
<213> ORGANISM: Unknown
<220> FEATURE:
<223> OTHER INFORMATION: Degenerate oligonucleotide primer

<400> SEQUENCE: 5
ctactattgt saaygayctv tattc                                       25

<210> SEQ ID NO 6
<211> LENGTH: 24
<212> TYPE: DNA
<213> ORGANISM: Unknown
<220> FEATURE:
<223> OTHER INFORMATION: Degenerate oligonucleotide primer

<400> SEQUENCE: 6
atdagsacyt attgcaarcr gccg                                        24

<210> SEQ ID NO 7
<211> LENGTH: 743
<212> TYPE: DNA
<213> ORGANISM: Anabaena Laxa

<400> SEQUENCE: 7
ttcttcgacg atcacttcct ggaaatctat aaacgcagtc aggatatggt tggggcgaag    60
gagtatcttg accgactccc cgcatttatg ccgatttatc ccagggacaa ccctctcgtt   120
cccaccaacc cagtagagcg cggtttggct gacttgtggt ctcgcaccgc atttactaag   180
tctgtggaat ggcggcgacg attctttaaa agtaccaaaa atcttttaga tgagtcaatg   240
tgggaactgg ccaacatcaa tcaaaatcga attgctaacc ccatcgaata cattgagatg   300
cggcgtaaag ttggtggcgc accctggtca gccgatctgg tggaacacgc gcgttcgtg    360 gaagtcccgg ctaaaattgc ggcaactaga ccaatgcggg ttttgaaaga cacatttgct   420
gatggagtac atctccgcaa cgacctattc tcctatcaaa gagaagtgga agatgaaggt   480
gaaaattcta attgtgtgct tgtaattgaa aaattcttga atgtaagtac ccaagaggcg   540
gctaacctca ctaacgaact actcaactcc cgtttatatc agtttgataa cactgctgtc   600
```

```
accgagttgc cctcccttt tgaggagtat ggagtagacc cagtagagcg tgtgaatgtt    660
ctcctttaca tcaaaggact tcaggattgg caatctggcg gtcatgagtg gcacatgaga    720
tcaagccgtt acatgaacga ggg                                            743
```

<210> SEQ ID NO 8
<211> LENGTH: 743
<212> TYPE: DNA
<213> ORGANISM: Phormidium calcicola

<400> SEQUENCE: 8

```
ttcttcgacg accacttcct tgaaatctat aagcgtaccc aagacatggc tggggcgaag     60
gagtatctcg gcagattacc aatgttcatg ccaatttacc ccactgaaac cccccccagta   120 cctaccaacc ccgtggagtg cggcttggcc gacctgtggt ctcgcaccgc atttactaaa   180
tctgtggact ggcggcttcg attcttcggg agtaccaaga acctcctgga agagtctctg   240
tgggaactcg cctacatcaa ccaggatcga gtcgctaacc ccatcgaata catcgaaatg   300
cgccgcaagg ttggtggcgc tccgtggtca gcggatctcg tcgaacacgc cgtgtttata   360
gagattccgg ctgacattgc ctcgactcgg ccaatgcgtg tgctaaaaga cacgtttgcc   420
gatgaagtgc atttacgcaa cgacctcttc tcctaccaga gagaagtgga agatgaaggc   480
gaaaatgcca actgtgtgtt ggtcttggag cgcttcttaa atgtgagtac ccaggaggca   540
gctaacctca ccaacgaact gctgacctcg cggttatacc agtttgataa cactgccgtc   600
accgagttgc ccccctctt tgaggagtat ggactagacc cagtggctcg tgtgaacgtt   660
ctcctttata tcaaaggact tcaggactgg cagtcgggcg gtcacgagtg gcacatgcga   720
tcaagccgtt acatgaacga ggg                                            743
```

<210> SEQ ID NO 9
<211> LENGTH: 743
<212> TYPE: DNA
<213> ORGANISM: Nostoc sp.

<400> SEQUENCE: 9

```
ttcttcgacg atcacttcct tgagctttac aagcgtagcc aagatatggc tggggctaag     60
aagtacctcg atggactgcc agcgtttatg cctgtacagc cacaagaaac gccgccagaa   120
cccaccaatg ccgtagaacg gggtttagta gacctctggg atcgcaccat ccccaatgca   180
tcccaagatt gggtaatccg gttttctgag agtaccatca atcttctcaa agaatctcag   240
tgggaactcg ccaatatcag ccaaaatcga gttgctaacc cgattgagta cattgagatg   300
cgccgtaagg tgggggggagc gccctggtca gctaacctag tggaacacgc ggttggggca   360
gacattccgg ctgcgatcgc cccgacccga ccaatgcgtg tcctcaaaga cacttttttct   420 gatggggtac atctgcgaaa tgatatcttc tcttaccaaa gagaagtgga agaagaaggg   480
gaaaatgcta actgtatcct ggttttagaa cgattcctgg atgtcagtac ccaagaggcg   540
gccaatctca ctaacgactt actaacatct agggtgcaac agttcgagaa caccttttgtc   600 actgagcttc cttctttgtt tgaggaatat agtctgagtc ccgatgagcg tctcaaagta   660
gtcctatatg ccaaaggact tcaggactgg cagtcggggg gtcatgagtg gcacatgaga   720
tcgagccgtt acatgaacga ggg                                            743
```

<210> SEQ ID NO 10
<211> LENGTH: 2220
<212> TYPE: DNA
<213> ORGANISM: Nostoc punctiforme

<400> SEQUENCE: 10

```
atggttatgc aaccctttga actgccagaa ttttacatgc cttggcccgc gcggctgaat         60
ccaaacctgg aagcggcgcg atcgcattcc aaagcctggg cttaccagat ggggatactt        120
ggctcaaaag aggaagcgga aagctcggtt atctgggacg agcgcacatt cgatgctcac        180
gactacgcct tgctttgctc gtatacccat ccagatgcac aggaacgga gcttgaccta         240
gtgaccgact ggtatgtttg gtgttcttc ttcgacgatc acttccttga aatctataag         300
cgtacccaag acatggctgg ggcgaaggag tatctcggca gattaccaat gttcatgcca        360
atttacccca ctgaaacccc cccagtacct accaaccccg tggagtgcgg cttggccgac        420
ctgtggtctc gcaccgcatt tactaaatct gtggactggc gacttcgatt cttcgagagt        480
accaagaacc tcctggaaga gtctctgtgg gaactcgcca atatcaacca ggatcgagtc        540
gctaacccca tcgaatacat cgaaatgcgc cgcaaggttg gtggcgctcc gtggtcagcg        600
gatctcgtcg aacacgccgt gtttatagag attccggctg acattgcctc gactcggcca        660
atgcgtgtgc taaaagacac gtttgccgat ggagtgcatt tacgcaacga cctcttctcc        720
taccagagag aagtggaaga tgaaggcgaa atgccaact gtgtgttggt cttggagcgc         780
ttcttaaatg tgagtaccca ggaggcagct aacctcacca cgaactgct gacctcgcgg         840
ttataccagt ttgataacac tgccgtcacc gagttgcccc ccctctttga ggagtatgga        900
ctagacccag tggctcgtgt gaacgttctc ctttatatca aaggacttca ggactggcag        960
tcgggcggtc acgagtggca catgcgatca agccgttaca tgaacaaggg aggagacaat       1020
tctccaacat ctacggttct ggaggaccc acagggctag gcacatcggc tgcgcggatt        1080
gaatcgttat atgcggcctt gggtttagga gaattaaaaa gcttcactca cgttccatac       1140
cagcctgtgg gaccagtgac cctgccgaag ttttacatgc cgttcactac aagtttgaat       1200
cctcatctca atgccgcacg gaagcattct aaggaatggg cgcgccagat ggggatgctg       1260
gaatcactac ctgggattcc tgatgccgtc atctgggatg accacaagtt tgatgttgcc       1320
gacgtagctc tctgcggtgc gttgatccat ccgaatgggt ctggtcttga actgaatctg       1380
acagcgtgct ggcttgtttg gggaacctat gccgacgatt acttcccggc gctctacggg       1440
aataaccgca acatggctgg tgcgaaagta ttcaacgctc gactgtcggc gttcatgcct       1500
ctggatgact ccaccccag cgaggttccg accaatccag tggaagcggg cttggcagat       1560
atttggtctc gcacagctgg tcccatgtct gccaacgcac ggactcagtt ccgccgcgca       1620
atccaggata tgactgacag ttgggtgtgg gaactcgcca accagatcca aaatcgaatt       1680
cctgacccga tagattatgt tgagatgcgc cgtaagacct ttggctcgga tctgaccatg       1740
agcctgtcgc gactagctca ggggagcgag atcccgcagg agatttaccg cacccgaacg       1800
atgcgatcgc tcgataattc ggccgccgac ttcgcctgtt taaccaacga tatcttttcc       1860
tatcagaaag aaatcgaatt cgaggcgaa atccataact gtgtgctggt cgttcagaat       1920
ttcctcaact gcgatttgcc gcaggccgtc gaagttgtca caacctgat gacctctagg        1980
gcgctccagt ttcaactcat cgtcgccacc gaactgccag ttcttttcga tgatttcgac       2040
ctggatgcaa gtacccgcga gaaactgctc ggatacgtca agaaactaga gcagtggatg       2100
tgcggcgtcc tcaagtggca tataacggta gaccgctata aggaatttga attgcgtaat       2160
tcgttagcag ggcggctact tagcggtccc agagggctgg gtacttcagc taggcgtatt       2220
```

<210> SEQ ID NO 11
<211> LENGTH: 247
<212> TYPE: PRT

<213> ORGANISM: Phormidium calcicola

<400> SEQUENCE: 11

```
Phe Phe Asp Asp His Phe Leu Glu Ile Tyr Lys Arg Thr Lys Asp Met
1               5                   10                  15
Lys Gly Ala Lys His Tyr Leu His Arg Leu Arg Ala Phe Met Pro Ile
            20                  25                  30
His Ser Thr Glu Thr Met Pro Ala Pro Thr Asn Pro Val Glu Arg Gly
        35                  40                  45
Leu Ala Asp Leu Trp Ser Arg Thr Ala Leu Thr Lys Ser Val Glu Trp
    50                  55                  60
Arg Val Arg Phe Ser Glu Ser Thr Lys Asn Leu Leu Glu Glu Ser Leu
65                  70                  75                  80
Trp Glu Leu Ala Asn Ile Asn Gln Asn Arg Val Ser Asn Pro Ile Glu
                85                  90                  95
Tyr Ile Glu Met Arg Arg Lys Val Gly Gly Ala Pro Trp Ser Ala Asp
            100                 105                 110
Leu Val Glu His Ala Ala Phe Val Glu Val Pro Ala Gln Ile Ala Ala
        115                 120                 125
Thr Arg Pro Met Arg Val Leu Lys Asp Thr Phe Ala Asp Gly Val His
    130                 135                 140
Leu His Asn Asp Leu Phe Ser Tyr Gln Arg Glu Val Glu Asp Glu Gly
145                 150                 155                 160
Glu Asn Ala Asn Cys Val Leu Val Leu Glu Arg Phe Leu Asp Val Thr
                165                 170                 175
Thr Gln Glu Ala Ala Asn Leu Thr Asn Glu Leu Leu Ser Ser Arg Leu
            180                 185                 190
Tyr Gln Phe Asp Asn Thr Ala Val Thr Glu Leu Pro Pro Leu Phe Glu
        195                 200                 205
Glu His Gly Leu Asp Pro Ala Ala Arg Met Ser Val Val Leu Tyr Ile
    210                 215                 220
Lys Gly Leu Gln Asp Trp Gln Ser Gly Gly His Glu Trp His Met Arg
225                 230                 235                 240
Ser Ser Arg Tyr Met Asn Lys
                245
```

<210> SEQ ID NO 12
<211> LENGTH: 247
<212> TYPE: PRT
<213> ORGANISM: Nostoc sp.

<400> SEQUENCE: 12

```
Phe Phe Asp Asp His Phe Leu Glu Leu Tyr Lys Arg Ser Gln Asp Met
1               5                   10                  15
Ala Gly Ala Lys Lys Tyr Leu Asp Gly Leu Pro Ala Phe Met Pro Val
            20                  25                  30
Gln Pro Gln Glu Thr Pro Pro Glu Pro Thr Asn Ala Val Glu Arg Gly
        35                  40                  45
Leu Val Asp Leu Trp Asp Arg Thr Ile Pro Asn Ala Ser Gln Asp Trp
    50                  55                  60
Val Ile Arg Phe Ser Glu Ser Thr Ile Asn Leu Leu Lys Glu Ser Gln
65                  70                  75                  80
Trp Glu Leu Ala Asn Ile Ser Gln Asn Arg Val Ala Asn Pro Ile Glu
                85                  90                  95
Tyr Ile Glu Met Arg Arg Lys Val Gly Gly Ala Pro Trp Ser Ala Asn
            100                 105                 110
```

Leu Val Glu His Ala Val Gly Ala Asp Ile Pro Ala Ala Ile Ala Pro
            115                 120                 125

Thr Arg Pro Met Arg Val Leu Lys Asp Thr Phe Ser Asp Gly Val His
130                 135                 140

Leu Arg Asn Asp Ile Phe Ser Tyr Gln Arg Glu Val Glu Glu Glu Gly
145                 150                 155                 160

Glu Asn Ala Asn Cys Ile Leu Val Leu Glu Arg Phe Leu Asp Val Ser
                165                 170                 175

Thr Gln Glu Ala Ala Asn Leu Thr Asn Asp Leu Leu Thr Ser Arg Val
            180                 185                 190

Gln Gln Phe Glu Asn Thr Phe Val Thr Glu Leu Pro Ser Leu Phe Glu
        195                 200                 205

Glu Tyr Ser Leu Ser Pro Asp Glu Arg Leu Lys Val Val Leu Tyr Ala
    210                 215                 220

Lys Gly Leu Gln Asp Trp Gln Ser Gly Gly His Glu Trp His Met Arg
225                 230                 235                 240

Ser Ser Arg Tyr Met Asn Glu
                245

<210> SEQ ID NO 13
<211> LENGTH: 247
<212> TYPE: PRT
<213> ORGANISM: Anabaena Laxa

<400> SEQUENCE: 13

Phe Phe Asp Asp His Phe Leu Glu Ile Tyr Lys Arg Ser Gln Asp Met
1               5                   10                  15

Val Gly Ala Lys Glu Tyr Leu Asp Arg Leu Pro Ala Phe Met Pro Ile
            20                  25                  30

Tyr Pro Arg Asp Asn Pro Leu Val Pro Thr Asn Pro Val Glu Arg Gly
        35                  40                  45

Leu Ala Asp Leu Trp Ser Arg Thr Ala Phe Thr Lys Ser Val Glu Trp
50                  55                  60

Arg Arg Arg Phe Phe Lys Ser Thr Lys Asn Leu Leu Asp Glu Ser Met
65                  70                  75                  80

Trp Glu Leu Ala Asn Ile Asn Gln Asn Arg Ile Ala Asn Pro Ile Glu
                85                  90                  95

Tyr Ile Glu Met Arg Arg Lys Val Gly Gly Ala Pro Trp Ser Ala Asp
            100                 105                 110

Leu Val Glu His Ala Ala Phe Val Glu Val Pro Ala Lys Ile Ala Ala
        115                 120                 125

Thr Arg Pro Met Arg Val Leu Lys Asp Thr Phe Ala Asp Gly Val His
130                 135                 140

Leu Arg Asn Asp Leu Phe Ser Tyr Gln Arg Glu Val Glu Asp Glu Gly
145                 150                 155                 160

Glu Asn Ser Asn Cys Val Leu Val Ile Glu Lys Phe Leu Asn Val Ser
                165                 170                 175

Thr Gln Glu Ala Ala Asn Leu Thr Asn Glu Leu Leu Asn Ser Arg Leu
            180                 185                 190

Tyr Gln Phe Asp Asn Thr Ala Val Thr Glu Leu Pro Ser Leu Phe Glu
        195                 200                 205

Glu Tyr Gly Val Asp Pro Val Glu Arg Val Asn Val Leu Leu Tyr Ile
    210                 215                 220

Lys Gly Leu Gln Asp Trp Gln Ser Gly Gly His Glu Trp His Met Arg
225                 230                 235                 240

```
Ser Ser Arg Tyr Met Asn Glu
            245

<210> SEQ ID NO 14
<211> LENGTH: 247
<212> TYPE: PRT
<213> ORGANISM: Nostoc punctiforme

<400> SEQUENCE: 14

Phe Phe Asp Asp His Phe Leu Glu Ile Tyr Lys Arg Thr Gln Asp Met
 1               5                  10                  15

Ala Gly Ala Lys Glu Tyr Leu Gly Arg Leu Pro Met Phe Met Pro Ile
            20                  25                  30

Tyr Pro Thr Glu Thr Pro Pro Val Pro Thr Asn Pro Val Glu Cys Gly
        35                  40                  45

Leu Ala Asp Leu Trp Ser Arg Thr Ala Phe Thr Lys Ser Val Asp Trp
 50                  55                  60

Arg Leu Arg Phe Phe Gly Ser Thr Lys Asn Leu Glu Glu Ser Leu
 65                  70                  75                  80

Trp Glu Leu Ala Tyr Ile Asn Gln Asp Arg Val Ala Asn Pro Ile Glu
                85                  90                  95

Tyr Ile Glu Met Arg Arg Lys Val Gly Gly Ala Pro Trp Ser Ala Asp
            100                 105                 110

Leu Val Glu His Ala Val Phe Ile Glu Ile Pro Ala Asp Ile Ala Ser
        115                 120                 125

Thr Arg Pro Met Arg Val Leu Lys Asp Thr Phe Ala Glu Val His
130                 135                 140

Leu Arg Asn Asp Leu Phe Ser Tyr Gln Arg Glu Val Glu Asp Glu Gly
145                 150                 155                 160

Glu Asn Ala Asn Cys Val Leu Val Leu Glu Arg Phe Leu Asn Val Ser
                165                 170                 175

Thr Gln Glu Ala Ala Asn Leu Thr Asn Glu Leu Leu Thr Ser Arg Leu
            180                 185                 190

Tyr Gln Phe Asp Asn Thr Ala Val Thr Glu Leu Pro Pro Leu Phe Glu
        195                 200                 205

Glu Tyr Gly Leu Asp Pro Val Ala Arg Val Asn Val Leu Leu Tyr Ile
    210                 215                 220

Lys Gly Leu Gln Asp Trp Gln Ser Gly Gly His Glu Trp His Met Arg
225                 230                 235                 240

Ser Ser Arg Tyr Met Asn Glu
            245

<210> SEQ ID NO 15
<211> LENGTH: 755
<212> TYPE: PRT
<213> ORGANISM: Nostoc punctiforme

<400> SEQUENCE: 15

Met Val Met Gln Pro Phe Glu Leu Pro Glu Phe Tyr Met Pro Trp Pro
 1               5                  10                  15

Ala Arg Leu Asn Pro Asn Leu Glu Ala Ala Arg Ser His Ser Lys Ala
            20                  25                  30

Trp Ala Tyr Gln Met Gly Ile Leu Gly Ser Lys Glu Ala Glu Ser
        35                  40                  45

Ser Val Ile Trp Asp Glu Arg Thr Phe Asp Ala His Asp Tyr Ala Leu
 50                  55                  60
```

```
Leu Cys Ser Tyr Thr His Pro Asp Ala Pro Gly Thr Glu Leu Asp Leu
 65                  70                  75                  80
Val Thr Asp Trp Tyr Val Trp Val Phe Phe Asp Asp His Phe Leu
                 85                  90                  95
Glu Ile Tyr Lys Arg Thr Gln Asp Met Ala Gly Ala Lys Glu Tyr Leu
                100                 105                 110
Gly Arg Leu Pro Met Phe Met Pro Ile Tyr Pro Thr Glu Thr Pro Pro
                115                 120                 125
Val Pro Thr Asn Pro Val Glu Cys Gly Leu Ala Asp Leu Trp Ser Arg
                130                 135                 140
Thr Ala Phe Thr Lys Ser Val Asp Trp Arg Leu Arg Phe Phe Glu Ser
145                 150                 155                 160
Thr Lys Asn Leu Leu Glu Glu Ser Leu Trp Glu Leu Ala Asn Ile Asn
                165                 170                 175
Gln Asp Arg Val Ala Asn Pro Ile Glu Tyr Ile Glu Met Arg Arg Lys
                180                 185                 190
Val Gly Gly Ala Pro Trp Ser Ala Asp Leu Val Glu His Ala Val Phe
                195                 200                 205
Ile Glu Ile Pro Ala Asp Ile Ala Ser Thr Arg Pro Met Arg Val Leu
210                 215                 220
Lys Asp Thr Phe Ala Asp Gly Val His Leu Arg Asn Asp Leu Phe Ser
225                 230                 235                 240
Tyr Gln Arg Glu Val Glu Asp Glu Gly Glu Asn Ala Asn Cys Val Leu
                245                 250                 255
Val Leu Glu Arg Phe Leu Asn Val Ser Thr Gln Glu Ala Ala Asn Leu
                260                 265                 270
Thr Asn Glu Leu Leu Thr Ser Arg Leu Tyr Gln Phe Asp Asn Thr Ala
                275                 280                 285
Val Thr Glu Leu Pro Pro Leu Phe Glu Glu Tyr Gly Leu Asp Pro Val
                290                 295                 300
Ala Arg Val Asn Val Leu Leu Tyr Ile Lys Gly Leu Gln Asp Trp Gln
305                 310                 315                 320
Ser Gly Gly His Glu Trp His Met Arg Ser Arg Tyr Met Asn Lys
                325                 330                 335
Gly Gly Asp Asn Ser Pro Thr Ser Thr Val Leu Gly Gly Pro Thr Gly
                340                 345                 350
Leu Gly Thr Ser Ala Ala Arg Ile Glu Ser Leu Tyr Ala Ala Leu Gly
                355                 360                 365
Leu Gly Arg Ile Lys Ser Phe Thr His Val Pro Tyr Gln Pro Val Gly
                370                 375                 380
Pro Val Thr Leu Pro Lys Phe Tyr Met Pro Phe Thr Thr Ser Leu Asn
385                 390                 395                 400
Pro His Leu Asn Ala Ala Arg Lys His Ser Lys Glu Trp Ala Arg Gln
                405                 410                 415
Met Gly Met Leu Glu Ser Leu Pro Gly Ile Pro Asp Ala Val Ile Trp
                420                 425                 430
Asp Asp His Lys Phe Asp Val Ala Asp Val Ala Leu Cys Gly Ala Leu
                435                 440                 445
Ile His Pro Asn Gly Ser Gly Leu Glu Leu Asn Leu Thr Ala Cys Trp
                450                 455                 460
Leu Val Trp Gly Thr Tyr Ala Asp Asp Tyr Phe Pro Ala Leu Tyr Gly
465                 470                 475                 480
Asn Asn Arg Asn Met Ala Gly Ala Lys Val Phe Asn Ala Arg Leu Ser
                485                 490                 495
```

-continued

```
Ala Phe Met Pro Leu Asp Asp Ser Thr Pro Ser Glu Val Pro Thr Asn
            500                 505                 510

Pro Val Glu Ala Gly Leu Ala Asp Ile Trp Ser Arg Thr Ala Gly Pro
        515                 520                 525

Met Ser Ala Asn Ala Arg Thr Gln Phe Arg Arg Ala Ile Gln Asp Met
    530                 535                 540

Thr Asp Ser Trp Val Trp Glu Leu Ala Asn Gln Ile Gln Asn Arg Ile
545                 550                 555                 560

Pro Asp Pro Ile Asp Tyr Val Glu Met Arg Arg Lys Thr Phe Gly Ser
                565                 570                 575

Asp Leu Thr Met Ser Leu Ser Arg Leu Ala Gln Gly Ser Glu Ile Pro
            580                 585                 590

Gln Glu Ile Tyr Arg Thr Arg Thr Met Arg Ser Leu Asp Asn Ser Ala
        595                 600                 605

Ala Asp Phe Ala Cys Leu Thr Asn Asp Val Phe Ser Tyr Gln Lys Glu
    610                 615                 620

Ile Glu Phe Glu Gly Glu Ile His Asn Cys Val Leu Val Gln Asn
625                 630                 635                 640

Phe Leu Asn Cys Asp Leu Pro Gln Ala Val Glu Val Val Asn Asn Leu
                645                 650                 655

Met Thr Ser Arg Ala Leu Gln Phe Gln Leu Ile Val Ala Thr Glu Leu
            660                 665                 670

Pro Val Leu Phe Asp Asp Phe Asp Leu Asp Ala Ser Thr Arg Glu Lys
        675                 680                 685

Leu Leu Gly Tyr Val Lys Lys Leu Glu Gln Trp Met Cys Gly Val Leu
    690                 695                 700

Lys Trp His Ile Thr Val Asp Arg Tyr Lys Glu Phe Glu Leu Arg Asn
705                 710                 715                 720

Ser Leu Ala Gly Arg Leu Leu Ser Gly Pro Arg Gly Leu Gly Thr Ser
                725                 730                 735

Ala Arg Arg Ile Gly Ser Leu Ile Gly Gln Gly Ser Leu Lys Ser Leu
            740                 745                 750

Leu Gly Gln
        755

<210> SEQ ID NO 16
<211> LENGTH: 755
<212> TYPE: PRT
<213> ORGANISM: Myxococcus xanthus

<400> SEQUENCE: 16

Met Ser Thr Ala Lys Asn Lys Gln Pro Phe Glu Leu Pro Asp Phe Tyr
1               5                   10                  15

Val Pro Trp Pro Ala Arg Leu Asn Pro Asn Leu Glu Gly Ala Arg Val
            20                  25                  30

His Ser Lys Ala Trp Ala Arg Glu Leu Gly Ile Ile Gly Arg Pro Lys
        35                  40                  45

Asp Gly Ser Ala Pro Glu Ile Trp Ser Glu Ala Lys Phe Asp Ala Met
    50                  55                  60

Asp Tyr Ala Leu Leu Cys Ala Tyr Thr His Pro Glu Ala Pro Gly Pro
65                  70                  75                  80

Glu Leu Asp Leu Val Thr Asp Trp Tyr Val Trp Val Phe Tyr Phe Asp
                85                  90                  95

Asp His Phe Leu Glu Leu Tyr Lys Arg Pro Gln Asp Gln Val Gly Ala
            100                 105                 110
```

-continued

Lys Ala Tyr Leu Asp Arg Leu Pro Leu Phe Met Pro Val Asp Pro Ala
            115                 120                 125

Ala Thr Pro Pro Pro Thr Asn Pro Val Glu Ala Gly Leu Leu Asp
    130                 135                 140

Leu Trp Asn Arg Thr Val Pro Ser Arg Ser Met Ala Trp Arg Arg
145                 150                 155                 160

Phe Phe Glu Ser Thr Lys His Leu Leu Asp Glu Ser Ser Trp Glu Leu
                165                 170                 175

Ser Asn Ile Ser Asp Arg Arg Val Ser Asn Pro Ile Glu Tyr Ile Glu
            180                 185                 190

Met Arg Arg Lys Val Gly Gly Ala Pro Trp Ser Ala Asn Leu Val Glu
            195                 200                 205

His Ala Val Phe Ala Glu Val Pro Asp Arg Val Ala Ala Ser Arg Pro
    210                 215                 220

Met Arg Val Leu Lys Asp Thr Phe Ser Asp Ala Val His Leu Arg Asn
225                 230                 235                 240

Asp Leu Phe Ser Tyr Glu Arg Glu Ile Leu Glu Glu Gly Glu Leu Ser
                245                 250                 255

Asn Gly Val Leu Val Met Glu Lys Phe Leu Asn Ile Ser Pro Pro Ser
            260                 265                 270

Ala Ala His Leu Val Asn Glu Val Leu Thr Ser Arg Leu Gln Gln Phe
    275                 280                 285

Glu Asn Thr Val Leu Thr Glu Leu Pro Ser Leu Phe Val Glu Phe Gly
    290                 295                 300

Leu Asn Pro Val Glu Gln Ala Gln Val Leu Thr Tyr Val Arg Gly Leu
305                 310                 315                 320

Gln Asp Trp Gln Ser Gly Gly His Glu Trp His Met Arg Ser Ser Arg
                325                 330                 335

Tyr Met Asn Lys Gly Ser Gly Gly Ala Gly Gly Phe Phe Leu Gly Pro
            340                 345                 350

Asn Gly Leu Gly Thr Ser Ala Ala Arg Leu Pro Gln Ser Pro Thr Ala
            355                 360                 365

Leu Gly Leu Thr Arg Leu Lys Asn Phe Ser His Val Pro Tyr Gln Pro
    370                 375                 380

Val Gly Pro Val Lys Leu Pro Lys Phe Tyr Met Pro Tyr Ser Thr Lys
385                 390                 395                 400

Pro Ser Pro His Leu Asp Ala Ala Arg Arg Asp Ser Lys Ala Trp Ala
                405                 410                 415

Arg Arg Met Gly Met Leu Asp Val Leu Pro Gly Val Pro Gly Gly Tyr
            420                 425                 430

Ile Trp Asp Asp His Lys Phe Asp Val Ala Asp Val Ala Leu Cys Gly
            435                 440                 445

Ala Leu Ile His Pro His Ala Thr Ala Ala Gln Leu Asn Leu Ser Ser
    450                 455                 460

Cys Trp Leu Val Trp Gly Thr Tyr Ala Asp Asp Tyr Phe Pro Ala Phe
465                 470                 475                 480

Tyr Gly His Thr Lys Asp Met Ala Gly Ala Lys Val Phe Asn Ala Arg
                485                 490                 495

Leu Ala Leu Phe Val Pro Glu Asp Ala Gly Val Val Pro Pro
            500                 505                 510

Thr Asn Pro Val Glu Arg Gly Leu Ala Asp Leu Trp Ala Arg Thr Thr
            515                 520                 525

Glu Gly Val Thr Pro Ala Ser Arg Ser Leu Phe Arg Lys Ala Ile Leu

```
                        530                 535                 540
Asp Met Thr Glu Ser Trp Val Trp Glu Leu Ala Asn Gln Ile Gln Asn
545                 550                 555                 560

Arg Ile Pro Asp Pro Ile Asp Tyr Val Glu Met Arg Arg Gln Thr Phe
                565                 570                 575

Gly Ser Asp Leu Thr Met Ser Leu Ser Arg Leu Ala His Gly Asp Ala
                580                 585                 590

Leu Pro Pro Glu Val Phe His Thr Arg Pro Ile Arg Ser Leu Glu Asn
                595                 600                 605

Ser Ala Ala Asp Tyr Ala Cys Leu Ile Asn Asp Val Phe Ser Tyr Gln
610                 615                 620

Lys Glu Ile Glu Phe Glu Gly Glu Leu Asn Asn Gly Val Leu Val Val
625                 630                 635                 640

Gln Arg Phe Leu Asp Leu Asp Pro Ala Arg Ala Val Ser Val Val Asn
                645                 650                 655

Asp Leu Met Thr Ala Arg Met Gln Gln Phe Glu Tyr Ile Ile Ala Asn
                660                 665                 670

Glu Leu Glu Pro Leu Ala Arg Asn Phe Asn Leu Asp Gly Lys Ala Gln
                675                 680                 685

Asp Lys Leu Lys Gln Tyr Val Gln Lys Leu Gln Trp Trp Met Ser Gly
690                 695                 700

Val Leu Ile Trp His Gln Thr Val Asp Arg Tyr Lys Glu Phe Glu Leu
705                 710                 715                 720

Arg Ala Ser Arg Lys Leu Ala Pro Arg Leu Ser Ser Gly Pro Thr Gly
                725                 730                 735

Leu Gly Thr Ser Ala Ala Arg Ile Thr Ser Leu Phe Ala Asn Leu Arg
                740                 745                 750

Ser Gly Ala
        755

<210> SEQ ID NO 17
<211> LENGTH: 704
<212> TYPE: PRT
<213> ORGANISM: Stigmatella aurantiaca

<400> SEQUENCE: 17

Met Asp Tyr Ala Leu Leu Cys Ala Tyr Thr His Pro Glu Ala Pro Ser
1               5                   10                  15

Leu Glu Leu Asp Leu Val Thr Asp Trp Tyr Val Trp Val Phe Tyr Phe
                20                  25                  30

Asp Asp His Phe Leu Asp Val Tyr Lys Arg Thr Gln Asp Gln Val Gly
            35                  40                  45

Ala Arg Glu Tyr Leu Asp Arg Leu Pro Ala Phe Met Pro Val Asp Leu
        50                  55                  60

Ser Ala Ala Pro Pro Thr Pro Thr Asn Pro Val Glu Arg Gly Leu Ala
65                  70                  75                  80

Asp Leu Trp Ala Arg Thr Val Pro Thr Lys Ser Glu Ala Trp Arg Arg
                85                  90                  95

Arg Phe Phe Glu Ser Thr Lys Ser Leu Leu Glu Ser Asn Trp Glu
                100                 105                 110

Leu Asn Asn Ile Ser Glu Arg Val Ser Asn Pro Ile Glu Tyr Ile
            115                 120                 125

Glu Met Arg Arg Lys Val Gly Gly Ala Pro Trp Ser Ala Asp Leu Val
130                 135                 140

Glu His Ala Val Phe Ala Glu Ile Pro Ala Arg Ile Ala Ala Ser Arg
```

```
              145                 150                 155                 160
        Pro Met Thr Val Leu Lys Asp Thr Phe Ser Asp Gly Val His Leu Arg
                        165                 170                 175

Asn Asp Leu Phe Ser Tyr Gln Arg Glu Ile Gln Glu Glu Gly Glu Leu
                        180                 185                 190

Ala Asn Cys Val Leu Val Phe Glu Lys Phe Leu Asn Val Asp Ala Gln
                        195                 200                 205

Arg Ala Ala Asn Leu Val Asn Glu Val Leu Thr Ser Arg Leu Gln Gln
                        210                 215                 220

Phe Glu Asn Thr Ala Leu Thr Glu Leu Pro Ser Leu Phe Glu Glu Asn
        225                 230                 235                 240

Ala Leu Asn Pro Val Glu Arg Ala His Val Leu Thr Tyr Val Arg Gly
                        245                 250                 255

Leu Gln Asp Trp Gln Ser Gly Gly His Glu Trp His Met Arg Ser Ser
                        260                 265                 270

Arg Tyr Met Asn Lys Gly Ala Gly Gly Ala Gly Asp Thr Asp Gly Leu
                        275                 280                 285

Pro Leu Gly Leu Ser Gly Leu Gly Leu Ser Ala Val Arg Phe Pro Phe
                        290                 295                 300

Ser Ala Ser Ala Leu Gly Leu Asn Arg Phe Lys Ser Phe Thr His Thr
        305                 310                 315                 320

Pro Tyr Met Pro Val Gly Pro Val Lys Leu Pro Lys Tyr Met Pro
                        325                 330                 335

Tyr Ser Thr Ser Val Ser Pro His Leu Asp Ala Ala Arg Arg His Ser
                        340                 345                 350

Lys Glu Trp Ala Arg Gln Met Gly Met Leu Asp Ser Leu Pro Gly Leu
                        355                 360                 365

Pro Gly Val Tyr Ile Trp Asp Asp His Lys Phe Asp Val Ala Asp Val
                        370                 375                 380

Ala Leu Cys Gly Ala Leu Ile His Pro Glu Ala Ser Ala Glu Gln Leu
        385                 390                 395                 400

Asn Leu Thr Ala Cys Trp Leu Val Trp Gly Thr Tyr Ala Asp Asp Tyr
                        405                 410                 415

Phe Pro Ala Phe Tyr Gly Tyr Thr Arg Asp Met Ala Gly Ala Lys Leu
                        420                 425                 430

Phe Asn Ala Arg Leu Ser Ala Phe Met Pro Asp Gly Pro Cys Thr Ala
                        435                 440                 445

Val Pro Thr Asn Pro Val Glu His Gly Leu Ala Asp Leu Trp Ala Arg
                        450                 455                 460

Thr Ala Gly Pro Met Thr Asp Asn Ala Arg Arg Leu Phe Arg Lys Ala
        465                 470                 475                 480

Ile Gln Asp Met Thr Ala Ser Trp Leu Trp Glu Leu Ala Asn Gln Ile
                        485                 490                 495

Gln Asn Arg Ile Pro Asp Pro Val Asp Tyr Val Glu Met Arg Arg Lys
                        500                 505                 510

Thr Phe Gly Ser Asp Leu Thr Met Ser Leu Ser Arg Leu Ala His Gly
                        515                 520                 525

Asp Ala Ile Pro Gln Glu Ile Phe His Thr Arg Pro Val Arg Gly Leu
                        530                 535                 540

Glu Asn Ser Ala Ala Asp Tyr Ala Cys Leu Thr Asn Asp Ile Phe Ser
        545                 550                 555                 560

Tyr Gln Lys Glu Ile Glu Tyr Glu Gly Glu Leu Asn Asn Gly Val Leu
                        565                 570                 575
```

```
Val Val Gln Arg Phe Leu Glu Ile Glu Pro Pro Gln Ala Val Glu Ile
            580                 585                 590

Val Asn Asp Leu Met Thr Ala Arg Met Arg Gln Phe Glu His Thr Val
        595                 600                 605

Lys Met Glu Leu Pro Leu Leu Ile Arg Ser Thr Gly Leu Asp Ala Lys
610                 615                 620

Ala Gln Glu Lys Leu Arg Thr Tyr Val Glu Lys Leu Gln Arg Trp Met
625                 630                 635                 640

Cys Gly Val Leu Arg Trp His Met Thr Val Asp Arg Tyr Lys Glu Phe
                645                 650                 655

Glu Leu Arg Asn Thr Arg Lys Pro Arg Arg Gly Gly Trp Glu Asp Pro
            660                 665                 670

Arg Asp Gly Ala Pro Pro Arg Pro Ala Ser Arg Arg Ser Leu Gly Ala
        675                 680                 685

Thr Gly Ala Glu Val Glu Lys Lys Leu Glu Lys Ser Gly Ser Ser Thr
    690                 695                 700

<210> SEQ ID NO 18
<211> LENGTH: 726
<212> TYPE: PRT
<213> ORGANISM: Streptomyces coelicolor

<400> SEQUENCE: 18

Met Thr Gln Gln Pro Phe Gln Leu Pro His Phe Tyr Leu Pro His Pro
 1                5                   10                  15

Ala Arg Leu Asn Pro His Leu Asp Glu Ala Arg Ala His Ser Thr Thr
            20                  25                  30

Trp Ala Arg Glu Met Gly Met Leu Glu Gly Ser Gly Val Trp Glu Gln
        35                  40                  45

Ser Asp Leu Glu Ala His Asp Tyr Gly Leu Leu Cys Ala Tyr Thr His
    50                  55                  60

Pro Asp Cys Asp Gly Pro Ala Leu Ser Leu Ile Thr Asp Trp Tyr Val
65                  70                  75                  80

Trp Val Phe Phe Phe Asp Asp His Phe Leu Glu Lys Tyr Lys Arg Ser
                85                  90                  95

Gln Asp Arg Leu Ala Gly Lys Ala His Leu Asp Arg Leu Pro Leu Phe
            100                 105                 110

Met Pro Leu Asp Asp Ala Ala Gly Met Pro Glu Pro Arg Asn Pro Val
        115                 120                 125

Glu Ala Gly Leu Ala Asp Leu Trp Thr Arg Thr Val Pro Ala Met Ser
130                 135                 140

Ala Asp Trp Arg Arg Arg Phe Ala Val Ala Thr Glu His Leu Leu Asn
145                 150                 155                 160

Glu Ser Met Trp Glu Leu Ser Asn Ile Asn Glu Gly Arg Val Ala Asn
                165                 170                 175

Pro Val Glu Tyr Ile Glu Met Arg Arg Lys Val Gly Gly Ala Pro Trp
            180                 185                 190

Ser Ala Gly Leu Val Glu Tyr Ala Thr Ala Glu Val Pro Ala Ala Val
        195                 200                 205

Ala Gly Thr Arg Pro Leu Arg Val Leu Met Glu Thr Phe Ser Asp Ala
    210                 215                 220

Val His Leu Arg Asn Asp Leu Phe Ser Tyr Gln Arg Glu Val Glu Asp
225                 230                 235                 240

Glu Gly Glu Leu Ser Asn Gly Val Leu Val Leu Glu Thr Phe Phe Gly
                245                 250                 255
```

-continued

Cys Thr Thr Gln Glu Ala Ala Asp Leu Val Asn Asp Val Leu Thr Ser
            260                 265                 270

Arg Leu His Gln Phe Glu His Thr Ala Phe Thr Glu Val Pro Ala Val
        275                 280                 285

Ala Leu Glu Lys Gly Leu Thr Pro Leu Glu Val Ala Ala Val Gly Ala
    290                 295                 300

Tyr Thr Lys Gly Leu Gln Asp Trp Gln Ser Gly His Glu Trp His
305                 310                 315                 320

Met Arg Ser Ser Arg Tyr Met Asn Lys Gly Glu Arg Pro Leu Ala Gly
                325                 330                 335

Trp Gln Ala Leu Thr Gly Pro Gly Thr Ser Ala Ala Val Gly Ala
            340                 345                 350

Leu Leu Ala Asp Ala Val Ala Gln Arg Ala Arg Ser Tyr Thr Tyr Val
        355                 360                 365

Pro Phe Gln Lys Val Gly Pro Ser Val Ile Pro Asp Ile Arg Met Pro
    370                 375                 380

Tyr Pro Leu Glu Leu Ser Pro Ala Leu Asp Gly Ala Arg Arg His Leu
385                 390                 395                 400

Ser Glu Trp Cys Arg Glu Met Gly Ile Leu Ser Glu Gly Val Trp Asp
                405                 410                 415

Glu Asp Lys Leu Glu Ser Cys Asp Leu Pro Leu Cys Ala Ala Gly Leu
            420                 425                 430

Asp Pro Asp Ala Thr Gln Asp Gln Leu Asp Leu Ala Ser Gly Trp Leu
        435                 440                 445

Ala Phe Gly Thr Tyr Gly Asp Asp Tyr Tyr Pro Leu Val Tyr Gly His
    450                 455                 460

Arg Arg Asp Leu Ala Ala Ala Arg Leu Thr Thr Thr Arg Leu Ser Asp
465                 470                 475                 480

Cys Met Pro Leu Asp Gly Glu Pro Val Pro Pro Gly Asn Ala Met
                485                 490                 495

Glu Arg Ser Leu Ile Asp Leu Trp Val Arg Thr Thr Ala Gly Met Thr
            500                 505                 510

Pro Glu Glu Arg Arg Pro Leu Lys Lys Ala Val Asp Asp Met Thr Glu
        515                 520                 525

Ala Trp Leu Trp Glu Leu Ser Asn Gln Ile Gln Asn Arg Val Pro Asp
    530                 535                 540

Pro Val Asp Tyr Leu Glu Met Arg Arg Ala Thr Phe Gly Ser Asp Leu
545                 550                 555                 560

Thr Leu Gly Leu Cys Arg Ala Gly His Gly Pro Ala Val Pro Pro Glu
                565                 570                 575

Val Tyr Arg Ser Gly Pro Val Arg Ser Leu Glu Asn Ala Ala Ile Asp
            580                 585                 590

Tyr Ala Cys Leu Leu Asn Asp Val Phe Ser Tyr Gln Lys Glu Ile Glu
        595                 600                 605

Tyr Glu Gly Glu Ile His Asn Ala Val Leu Val Gln Asn Phe Phe
    610                 615                 620

Gly Val Asp Tyr Pro Ala Ala Leu Gly Val Val Gln Asp Leu Met Asn
625                 630                 635                 640

Gln Arg Met Arg Gln Phe Glu His Val Ala His Glu Leu Pro Val
                645                 650                 655

Val Tyr Asp Asp Phe Gln Leu Ser Glu Glu Ala Arg Thr Val Met Arg
            660                 665                 670

Gly Tyr Val Thr Asp Leu Gln Asn Trp Met Ala Gly Ile Leu Asn Trp
        675                 680                 685

```
His Arg Asn Val Pro Arg Tyr Lys Ala Glu Tyr Leu Ala Gly Arg Thr
    690                 695                 700

His Gly Phe Leu Pro Asp Arg Ile Pro Ala Pro Pro Val Pro Arg Ser
705                 710                 715                 720

Ser Pro Ala Leu Thr His
                725

<210> SEQ ID NO 19
<211> LENGTH: 725
<212> TYPE: PRT
<213> ORGANISM: Streptomyces avermitilis

<400> SEQUENCE: 19

Met Thr Gln Pro Phe Gln Leu Pro His Phe Tyr Met Pro Tyr Pro Ala
  1               5                  10                  15

Arg Leu Asn Pro His Leu Asp Glu Ala Arg Ala His Ser Thr Arg Trp
                 20                  25                  30

Ala Arg Gly Met Gly Met Leu Glu Gly Ser Gly Ile Trp Glu Gln Ser
             35                  40                  45

Asp Leu Asp Ala His Asp Tyr Gly Leu Leu Cys Ala Tyr Thr His Pro
 50                  55                  60

Asp Cys Asp Gly Pro Ala Leu Ser Leu Ile Thr Asp Trp Tyr Val Trp
65                  70                  75                  80

Val Phe Phe Phe Asp Asp His Phe Leu Glu Thr Phe Lys Arg Thr Gln
                 85                  90                  95

Asp Arg Glu Gly Gly Lys Ala Tyr Leu Asp Arg Leu Pro Leu Phe Met
            100                 105                 110

Pro Leu Asp Leu Ser Ala Pro Val Pro Glu Pro Glu Asn Pro Val Glu
        115                 120                 125

Ala Gly Leu Ala Asp Leu Trp Ala Arg Thr Val Pro Ala Met Ser Ala
130                 135                 140

Asp Trp Arg Lys Arg Phe Ala Val Ser Thr Glu His Leu Leu Asn Glu
145                 150                 155                 160

Ser Leu Trp Glu Leu Ser Asn Ile Asn Glu Gly Arg Ile Ala Asn Pro
                165                 170                 175

Val Glu Tyr Ile Glu Met Arg Arg Lys Val Gly Gly Ala Pro Trp Ser
            180                 185                 190

Ala Gly Leu Val Glu Tyr Ala Thr Ala Glu Val Pro Ala Ala Val Ala
        195                 200                 205

Gly Ser Arg Pro Leu Arg Val Leu Met Glu Thr Phe Ser Asp Gly Val
    210                 215                 220

His Leu Arg Asn Asp Leu Phe Ser Tyr Gln Arg Glu Val Glu Glu Glu
225                 230                 235                 240

Gly Glu Leu Ser Asn Gly Val Leu Val Leu Glu Thr Phe Phe Gly Cys
                245                 250                 255

Thr Thr Gln Glu Ala Ala Glu Thr Val Asn Asp Ile Leu Thr Ser Arg
            260                 265                 270

Leu His Gln Phe Glu His Thr Ala Leu Thr Val Pro Ala Leu Ala
        275                 280                 285

Leu Glu Lys Gly Leu Thr Pro Pro Glu Val Ala Ala Val Ala Ala Tyr
    290                 295                 300

Ala Arg Gly Leu Gln Asp Trp Gln Ser Gly Gly His Glu Trp His Leu
305                 310                 315                 320

Arg Ser Ser Arg Tyr Met Asn Glu Gly Ala Leu Ser Gln Lys Arg Pro
                325                 330                 335
```

```
Phe Gly Leu Ser Ala Ile Gly Thr Ser Ala Ala Asp Leu Arg Gly Leu
                340                 345                 350

Leu Ala Asp Ala Gly Ala Glu Arg Leu Arg Arg Tyr Thr His Val Pro
            355                 360                 365

Phe Gln Lys Val Gly Pro Ser Arg Ile Pro Asp Phe His Met Pro Phe
        370                 375                 380

Gln Val Glu Leu Ser Pro His Leu Gly Ala Arg Ala Arg Leu Thr
385                 390                 395                 400

Pro Trp Met His Ser Thr Gly Met Leu Gln Glu Gly Val Trp Asp Glu
                405                 410                 415

Asp Lys Leu Thr Ala Tyr Asp Leu Pro Leu Cys Ser Ala Gly Leu Asp
            420                 425                 430

Pro Asp Ala Thr Pro Asp Glu Leu Asp Leu Ser Ser Arg Trp Leu Ala
        435                 440                 445

Trp Gly Thr Tyr Gly Asp Asp Tyr Tyr Pro Met Val Phe Gly Pro Arg
    450                 455                 460

Arg Asp Leu Ala Ala Lys Leu Cys Thr Arg Arg Leu Ser Ala Cys
465                 470                 475                 480

Met Pro Val Asp Gly Glu Glu Val Pro Ala Pro Val Asn Gly Met Glu
                485                 490                 495

Arg Gly Leu Ile Asp Leu Trp Ala Ile Thr Thr Ala Glu Met Thr Pro
            500                 505                 510

Asp Glu Arg Arg Thr Phe Arg Ala Ser Val Asp Val Met Thr Glu Ser
        515                 520                 525

Trp Val Trp Glu Leu Ser Asn Gln Leu Gln His Arg Ile Pro Asp Pro
    530                 535                 540

Ile Asp Tyr Leu Glu Met Arg Arg Ala Thr Phe Gly Ala Asp Leu Thr
545                 550                 555                 560

Leu Ser Leu Cys Arg Val Gly His Gly Pro Lys Val Pro Pro Glu Ile
                565                 570                 575

Tyr Arg Ser Gly Pro Val Arg Ser Leu Glu Asn Ala Ala Val Asp Tyr
            580                 585                 590

Gly Met Leu Ile Asn Asp Val Phe Ser Tyr Gln Lys Glu Ile Glu Tyr
        595                 600                 605

Glu Gly Glu Val His Asn Ala Ile Leu Val Gln Asn Phe Gly
    610                 615                 620

Cys Asp Tyr Pro Thr Ala Leu Gly Val Ile Asn Asp Leu Met Thr Gln
625                 630                 635                 640

Arg Met His Gln Phe Glu His Val Ala Ala His Glu Leu Pro Leu Leu
                645                 650                 655

Tyr Lys Asp Phe Lys Leu Pro Gln Glu Val Arg Asp Ile Met Asp Gly
            660                 665                 670

Tyr Val Val Glu Leu Gln Asn Trp Met Ser Gly Ile Leu Lys Trp His
        675                 680                 685

Gln Asp Cys His Arg Tyr Gly Ala Ala Asp Leu Ala Arg Arg Ala His
    690                 695                 700

Gly Phe Val Pro Asp Arg Ala Pro Ser Ala Pro Phe Thr Ala Trp Ala
705                 710                 715                 720

Ala Pro Val Ala Arg
                725

<210> SEQ ID NO 20
<211> LENGTH: 751
<212> TYPE: PRT
```

<213> ORGANISM: Frankia sp.

<400> SEQUENCE: 20

```
Met Gln Pro Phe Thr Leu Pro Glu Phe Tyr Val Pro Tyr Pro Ala Arg
 1               5                  10                  15

Leu Asn Pro Asn Leu Glu Gln Ala Arg Val His Ser Arg Ala Trp Ala
            20                  25                  30

Asp Glu Met Glu Met Ile Asp Ser Pro Gln His Gly Thr Ala Ile Trp
        35                  40                  45

Thr Glu Ala Asp Phe Asp Ala His Asp Tyr Ala Leu Leu Cys Ala Tyr
    50                  55                  60

Thr His Pro Asp Ser Val Ser Arg Lys Leu Asp Leu Val Thr Asp Trp
65                  70                  75                  80

Tyr Val Trp Val Phe Tyr Phe Asp Asp His Phe Leu Glu Leu Tyr Lys
                85                  90                  95

Arg Ser His Asp Met Ala Gly Ala Arg Ala Tyr Leu Asp Arg Leu Pro
            100                 105                 110

Ala Phe Met Pro Val Asp Gly Glu Ile Thr Glu Thr Pro Thr Asn Pro
        115                 120                 125

Val Glu Arg Gly Leu Ala Asp Leu Trp Thr Arg Thr Val Pro Glu Arg
    130                 135                 140

Ser Ala Asp Trp Arg Arg Arg Phe Ala Val Ser Thr Lys Asn Leu Leu
145                 150                 155                 160

Asp Glu Ser Leu Trp Glu Leu Ala Asn Ile Asn Ala Gly Arg Leu Ala
                165                 170                 175

Asn Pro Ile Glu Tyr Val Glu Met Arg Arg Lys Val Gly Gly Ala Pro
            180                 185                 190

Trp Ser Ala Asn Leu Val Glu His Ala Ala Asp Ala Glu Val Pro Ala
        195                 200                 205

Gln Val Ala Ala Thr Arg Pro Leu Gln Val Leu Arg Asp Thr Phe Ala
    210                 215                 220

Asp Ala Val His Leu Arg Asn Asp Leu Phe Ser Tyr Gln Arg Glu Val
225                 230                 235                 240

Glu Glu Glu Gly Glu Leu Ser Asn Gly Val Leu Val Ile Glu Arg Phe
                245                 250                 255

Leu Gly Cys Gly Thr Gln Glu Ala Ala Asp Thr Val Asn Asp Leu Leu
            260                 265                 270

Thr Ser Arg Leu His Gln Phe Glu His Thr Ala Val Thr Glu Leu Pro
        275                 280                 285

Ala Val Leu Glu Glu His Gly Val Asp Pro Gly Ser Arg Leu Glu Val
    290                 295                 300

Leu Ala Tyr Val Lys Gly Leu Gln Asp Trp Gln Ser Gly Gly His Glu
305                 310                 315                 320

Trp His Leu Arg Ser Ser Arg Tyr Met Asn Arg Ala Val Ala Pro Glu
                325                 330                 335

Ser Gly Glu Leu Ser Gly Leu Leu Gly Leu Thr Gly Leu Gly Thr Ser
            340                 345                 350

Ala Ala Arg Ile Val Pro Ser Leu Val Thr Thr Pro Arg Arg Ile
        355                 360                 365

Arg Ser Phe Thr His Ile Pro His Gln Ile Val Gly Pro Leu Arg His
    370                 375                 380

Pro Asp Phe Cys Met Pro Phe Ser Thr Gly Gln Ser Pro His Leu Asp
385                 390                 395                 400

Ala Ser Arg Arg Glu Asn Ile Ile Trp Ala Arg Ala Val Gly Met Leu
```

```
                405                 410                 415
Asp Pro Ile Pro Gly Ile Trp Asp Glu His Lys Leu Arg Ala Phe Asp
            420                 425                 430

Phe Ala Leu Cys Ser Ala Gly Ile His Pro Asp Ala Thr Leu Pro Glu
            435                 440                 445

Leu Asn Leu Thr Thr Asp Trp Leu Thr Trp Gly Thr Tyr Ala Asp Asp
            450                 455                 460

Tyr Tyr Pro Val Ile Phe Gly Arg Thr Arg Asp Ile Leu Gly Ala Lys
465                 470                 475                 480

Val Cys Asn Ala Arg Leu Ser Glu Phe Met Pro Leu Asp Ser Pro Val
                485                 490                 495

Thr Ala Val Pro Ala Asn Ala Leu Glu Arg Gly Leu Ala Asp Leu Trp
            500                 505                 510

Thr Arg Thr Thr Glu Thr Met Ala Pro Gly Ala Arg Glu Thr Phe Arg
            515                 520                 525

Gly Thr Val Glu Val Met Ile Asp Ser Trp Leu Trp Glu Leu Ala Asn
            530                 535                 540

Gln Ala Gln Asn Arg Ile Pro Asp Pro Ile Asp Tyr Ile Glu Met Arg
545                 550                 555                 560

Arg Ala Thr Phe Gly Ser Asp Leu Thr Met Ser Leu Ala Arg Leu Ala
                565                 570                 575

Arg Leu Ala Gln Glu Gln Thr Val Pro Pro Glu Ile Tyr Arg Thr Arg
            580                 585                 590

Pro Ile Gln Ala Leu Glu Asn Ala Ala Ala Asp Tyr Ala Cys Leu Leu
            595                 600                 605

Asn Asp Val Phe Ser Tyr Gln Lys Glu Ile Gln Phe Glu Gly Glu Ile
            610                 615                 620

His Asn Cys Val Leu Val Val Glu Asn Phe Leu Asp Cys Asp Arg Glu
625                 630                 635                 640

Arg Ala Leu Ala Val Val Asn Asp Leu Met Thr Ser Arg Ile Arg Gln
                645                 650                 655

Phe Glu His Ile Val Ala His Glu Leu Pro Ala Leu Phe Asp Ser Phe
            660                 665                 670

Ala Leu Asp Ala Ser Ala Arg Gln Ala Leu Leu Gly Tyr Ala Arg Glu
            675                 680                 685

Leu Gln Asn Trp Leu Ala Gly Ile Leu Arg Trp His Glu Gly Thr His
            690                 695                 700

Arg Tyr Glu Glu Ser Glu Leu Arg Tyr His Pro Ala Ala Gly Val Arg
705                 710                 715                 720

Pro Phe Gly Gly Pro Thr Gly Leu Gly Thr Ser Ser Ala His Val Arg
                725                 730                 735

Pro Arg Pro Ala Ala Ala Ala Gly Ala Ala Gly Asp Ser Glu Met
            740                 745                 750

<210> SEQ ID NO 21
<211> LENGTH: 758
<212> TYPE: PRT
<213> ORGANISM: Frankia alni

<400> SEQUENCE: 21

Met Gln Pro Phe Thr Leu Pro Glu Phe Tyr Val Pro Tyr Pro Ala Arg
  1               5                  10                  15

Leu Ser Pro His Leu Glu Gln Ala Arg Glu His Ser Arg Glu Trp Ala
             20                  25                  30

Arg Ala Met Glu Met Ile Asp Thr Pro Gln His Gly Ile Ala Ile Trp
```

```
            35                  40                  45
Thr Glu Arg Asp Leu Asp Ala His Asp Tyr Ala Leu Leu Cys Ala Tyr
 50                  55                  60
Thr His Pro Asp Ala Thr Ala Asp Arg Leu Asn Leu Ile Thr Asp Trp
 65                  70                  75                  80
Tyr Val Trp Val Phe Tyr Phe Asp Asp His Phe Leu Glu Leu Tyr Lys
                 85                  90                  95
Arg Ser His Asp Leu Ala Gly Ala Arg Ala Tyr Leu Asp Arg Leu Pro
                100                 105                 110
Ala Phe Met Pro Val Asp Gly Glu Ile Thr Glu Pro Ser Asn Pro
            115                 120                 125
Val Glu Arg Gly Leu Ala Asp Leu Trp Thr Arg Thr Val Pro Ala Arg
            130                 135                 140
Ser Ala Asp Trp Arg Ala Arg Phe Ala Val Ser Thr Arg Asn Leu Leu
145                 150                 155                 160
Asp Glu Ser Leu Trp Glu Leu Glu Asn Ile Asn Ala Ala Arg Leu Ser
                165                 170                 175
Asn Pro Ile Glu Tyr Ile Glu Met Arg Arg Lys Val Gly Gly Ala Pro
                180                 185                 190
Trp Ser Ala Asn Leu Val Glu His Ala Ala Asp Ala Glu Val Pro Ala
            195                 200                 205
Arg Val Ala Ala Thr Arg Pro Leu Gln Val Leu Arg Asp Thr Phe Ala
            210                 215                 220
Asp Ala Val His Leu Arg Asn Asp Leu Phe Ser Tyr Glu Arg Glu Val
225                 230                 235                 240
Thr Glu Glu Gly Glu Leu Ser Asn Gly Val Leu Val Glu Arg Phe
                245                 250                 255
Leu Asp Ile Asp Thr Gln Ala Ala Asp Thr Val Asn Asp Leu Leu
            260                 265                 270
Thr Ser Arg Leu His Gln Phe Glu His Thr Ala Ala Thr Glu Leu Pro
            275                 280                 285
Ala Val Leu Asp Glu His Ala Ile Asp Pro Ala Gly Arg Leu Ala Ala
            290                 295                 300
Leu Ala Tyr Ile Lys Gly Leu Gln Asp Trp Gln Ser Gly His Glu
305                 310                 315                 320
Trp His Leu Arg Ser Ser Arg Tyr Met Asn Arg Glu Ala Thr Pro Asp
                325                 330                 335
Ala Val Pro Pro Gly Leu Gly Pro Leu Ala Gly Leu Gly Gly Thr Gly
                340                 345                 350
Ser Leu Val Pro Ala Ala Gly Leu Pro Gly Ile Pro Gly Ile Pro Ser
            355                 360                 365
Leu Gly Thr Ser Ala Ile Gln Val Leu Pro Ser Leu Leu Ala Thr Ala
            370                 375                 380
Pro Arg Arg Ile Arg Ser Phe Ala Asn Val Pro Phe Arg Leu Val Gly
385                 390                 395                 400
Pro Thr Pro Leu Pro Glu Phe Tyr Leu Pro Tyr Thr Thr Gly Leu Ser
                405                 410                 415
Pro His Leu Asp Ser Ser Arg Arg Ala Ile Ile Pro Trp Ala Arg Ser
            420                 425                 430
Met Gly Met Leu Asp Arg Val Pro Gly Ile Trp Asp Glu His Lys Leu
            435                 440                 445
Trp Ser Tyr Asp Phe Ala Leu Cys Ser Ala Gly Ile His Pro Asp Ala
450                 455                 460
```

```
Thr Ala Asp Glu Leu Asp Leu Thr Thr Ala Trp Leu Thr Trp Gly Thr
465                 470                 475                 480

Tyr Gly Asp Asp Tyr Tyr Pro Val Ile Phe Gly Ala Ser Arg Asn Leu
                485                 490                 495

Ala Ala Ala Lys Leu Cys Asn Glu Arg Leu Arg Leu Phe Met Pro Val
            500                 505                 510

Asp Gly Pro Leu Thr Glu Pro Val Asn Ala Leu Glu Arg Gly Leu
            515                 520                 525

Ala Asp Leu Trp Glu Arg Thr Gly Ala Gly Met Glu Pro Ala Ala Arg
530                 535                 540

Ala Thr Phe Arg Arg Thr Ile Glu Val Met Ile Asp Ser Trp Leu Trp
545                 550                 555                 560

Glu Leu Ala Asn Gln Ala His Asn Arg Ile Pro Asp Pro Val Asp Tyr
                565                 570                 575

Leu Glu Met Arg Arg Ala Thr Phe Gly Ser Asp Leu Thr Met Ser Leu
                580                 585                 590

Cys Arg Leu Ala Arg Trp His Ser Val Pro Ala Glu Val Phe Gly Thr
                595                 600                 605

Arg Pro Leu Arg Ala Leu Glu Asn Ala Ala Ala Asp Tyr Ala Cys Leu
610                 615                 620

Leu Asn Asp Ile Phe Ser Tyr Gln Lys Glu Ile Gln Phe Glu Gly Glu
625                 630                 635                 640

Ile His Asn Cys Val Leu Val Glu Asn Phe Leu Asp Cys Asp Arg
                645                 650                 655

Gly Arg Ala Val Glu Val Val Asn Ala Leu Met Thr Ala Arg Met Arg
                660                 665                 670

Gln Phe Glu His Val Val Asp Arg Glu Leu Pro Asp Leu Phe Asp Arg
                675                 680                 685

Leu Asp Leu Asp Gly Glu Ala Arg Ala Ala Ile Val Ser Tyr Ala Arg
690                 695                 700

Glu Leu Gln Asn Trp Leu Ala Gly Ile Leu Arg Trp His Gln Gly Thr
705                 710                 715                 720

His Arg Tyr Glu Glu Ala Glu Leu Arg Tyr His Pro Ala Ala Asp Arg
                725                 730                 735

Arg Pro Phe Gly Ser Pro Thr Gly Leu Gly Thr Ser Ala Ala Asp Val
                740                 745                 750

Arg Arg Leu Ala Ser Arg
                755

<210> SEQ ID NO 22
<211> LENGTH: 750
<212> TYPE: PRT
<213> ORGANISM: Frankia sp.

<400> SEQUENCE: 22

Met Gln Pro Phe Thr Leu Pro Glu Phe Tyr Leu Pro Tyr Pro Pro Arg
1               5                   10                  15

Leu Asn Pro Asn Leu Glu His Ala Arg Val His Ser Arg Ala Trp Ala
                20                  25                  30

Gly Glu Met Glu Met Ile Asp Val Pro Gln Asp Gly Val Ala Ile Trp
            35                  40                  45

Ser Gly Gln Asp Phe Asp Ser His Asp Tyr Ala Leu Leu Cys Ala Tyr
50                  55                  60

Thr His Pro Asp Ala Asp Glu Ala Arg Leu Asp Leu Ile Thr Asp Trp
65                  70                  75                  80
```

-continued

```
Tyr Val Trp Val Phe Tyr Phe Asp Asp His Phe Leu Glu Val Tyr Lys
                85                  90                  95

Arg Gly Arg Asp Val Ala Gly Ala Arg Tyr Leu Asp Arg Leu Arg
            100                 105                 110

Leu Phe Met Pro Val Glu Gly Ala Val Thr Ala Glu Pro Ala Asn Pro
        115                 120                 125

Val Glu Arg Gly Leu Ala Asp Leu Trp Ser Arg Thr Val Pro Asp Arg
    130                 135                 140

Thr Pro Ala Trp Arg Arg Phe Ala Thr Ser Thr Arg His Leu Leu
145                 150                 155                 160

Asp Glu Ser Leu Trp Glu Leu Ala Asn Ile Asp Glu Asn Arg Leu Ala
                165                 170                 175

Asn Pro Val Glu Tyr Ile Glu Met Arg Arg Lys Val Gly Gly Ala Pro
            180                 185                 190

Trp Ser Ala Asn Leu Val Glu His Ala Ala Asp Ala Glu Val Pro Asp
        195                 200                 205

Ala Ile Ala Ala Thr Arg Pro Ala Gln Val Leu Arg Asp Thr Phe Ser
    210                 215                 220

Asp Ala Ile His Leu Arg Asn Asp Leu Phe Ser Tyr Gln Arg Glu Val
225                 230                 235                 240

Gln Glu Glu Gly Glu Leu Ser Asn Gly Val Leu Val Leu Glu Arg Phe
                245                 250                 255

Leu Asp Cys Pro Thr Gln Gln Ala Ala Asp Ala Val Asn Asp Leu Leu
            260                 265                 270

Thr Ser Arg Leu His Gln Phe Glu His Thr Ala Leu Thr Glu Leu Pro
        275                 280                 285

Pro Val Leu Asp Glu His Gly Val Thr Pro Thr Ala Arg Arg Asp Val
    290                 295                 300

Leu Ala Tyr Val Lys Gly Leu Gln Asp Trp Gln Ala Gly His Glu
305                 310                 315                 320

Trp His Met Arg Ser Ser Arg Tyr Met Asn Ala Glu Ser Gly Ala Thr
                325                 330                 335

Gly Pro Val Pro Gly Ser Leu Pro Gly Asp Ala Thr Gly Leu Gly Thr
            340                 345                 350

Ser Ala Val Arg Ile Ala Ala Ser Leu Leu Ala Thr Ala Pro Ala Arg
        355                 360                 365

Met Arg Ala Phe Thr His Val Pro His Gln Val Val Gly Pro Val Lys
    370                 375                 380

Leu Pro Ala Phe Tyr Met Pro Phe Thr Thr Gly Glu Ser Arg His Leu
385                 390                 395                 400

Ala Ala Ala Arg His Asn Ile Val Glu Trp Ser Ala Ala Val Gly Phe
                405                 410                 415

Leu Asp Pro Val Pro Gly Ile Trp Asp Glu His Lys Leu Arg Ala Ala
            420                 425                 430

Asp Phe Ala Leu Cys Ser Ala Ala Ile His Pro Asn Ala Thr Ala Ala
        435                 440                 445

Glu Leu Asp Leu Thr Thr Gly Trp Leu Thr Trp Gly Thr Tyr Ala Asp
    450                 455                 460

Asp Leu Tyr Pro Val Leu Tyr Gly Arg Thr Arg Asp Leu Ala Gly Ala
465                 470                 475                 480

Arg Ala Cys Thr Glu Arg Leu Lys Glu Leu Met Pro Val Glu Pro Gly
                485                 490                 495

Pro Leu Pro Val Pro Val Gly Gly Leu Glu Arg Gly Leu Ala Asp Leu
            500                 505                 510
```

```
Trp Pro Arg Thr Thr Arg Asp Met Thr Pro Asp Ser Arg Arg Thr Phe
        515                 520                 525

Arg Arg Thr Val Cys Ile Met Leu Asp Ser Trp Gln Trp Glu Leu Ala
    530                 535                 540

Asn Gln Ala Gln Asn Arg Ile Pro Asp Pro Val Asp Tyr Ile Glu Met
545                 550                 555                 560

Arg Arg Arg Thr Phe Gly Ser Asp Leu Thr Met Ser Leu Ser Arg Leu
                565                 570                 575

Gly His Gly Arg Ser Val Pro Pro Glu Ile Tyr Gly Thr Arg Pro Ile
            580                 585                 590

Arg Ala Leu Glu Asn Ser Ala Ala Asp Tyr Ser Cys Leu Leu Asn Asp
        595                 600                 605

Ile Phe Ser Tyr Gln Lys Glu Ile Gln Phe Glu Gly Glu Ile His Asn
                610                 615                 620

Cys Val Leu Val Phe Gln Asn Phe Leu Gly Cys Gly Ala Glu Arg Ala
625                 630                 635                 640

Ile Gly Val Val Asn Asp Leu Met Thr Ala Arg Leu Arg Glu Phe Glu
                645                 650                 655

His Val Val Asp Val Glu Leu Pro Ala Leu Phe Asp Thr Tyr Glu Leu
            660                 665                 670

Thr Glu Glu Ala Arg Asp Val Leu Arg Gly Tyr Val Gly Glu Leu Lys
        675                 680                 685

Ser Trp Leu Ala Gly Val Leu Arg Trp His Gln Gly Thr Arg Arg Tyr
    690                 695                 700

Asp Glu Ala Glu Leu Arg His His Pro Ala Val Gly Val Arg Pro Phe
705                 710                 715                 720

Gly Gly Pro Val Gly Leu Gly Thr Ser Ala Ala Asp Ile Arg Arg Ala
                725                 730                 735

Leu Ser Gly Lys Ser Gly Gln Pro Thr Ala Leu Thr Gly Ser
            740                 745                 750

<210> SEQ ID NO 23
<211> LENGTH: 758
<212> TYPE: PRT
<213> ORGANISM: Saccharopolyspora erythraea

<400> SEQUENCE: 23

Met Gln Pro Phe Gln Gln Pro Glu Phe Tyr Met Pro Tyr Pro Ala Arg
1               5                   10                  15

Leu Asn Pro Asn Leu Glu Arg Ala Arg Glu His Ser Lys Ala Trp Ala
            20                  25                  30

Cys Ala Met Asp Met Ile Asp Val Pro Gln Glu Gly Thr Leu Ile Trp
        35                  40                  45

Asp Glu Asn Asp Phe Asp Ser His Asp Tyr Ala Leu Leu Cys Ala Tyr
    50                  55                  60

Thr His Pro Asp Ala Asp Gly Pro Met Leu Asp Leu Ile Thr Asp Trp
65                  70                  75                  80

Tyr Val Trp Val Phe Tyr Phe Asp Asp His Phe Val Glu Leu Tyr Lys
                85                  90                  95

Arg Asn Pro Asp Leu Ala Gly Ala Lys Glu Tyr Leu Asp Arg Leu Pro
            100                 105                 110

Ala Phe Met Pro Val Glu Gly Pro Ile Thr Ala Glu Pro Thr Asn Pro
        115                 120                 125

Val Glu Arg Gly Leu Ala Asp Leu Trp Gln Arg Thr Val Pro Ala Arg
    130                 135                 140
```

-continued

Thr Ala Asp Trp Arg Arg Arg Tyr Ala Glu Asn Thr Lys His Leu Leu
145                 150                 155                 160

Asp Glu Ser Leu Trp Glu Leu Ser Asn Ile Ser Arg Asn Arg Leu Ser
                165                 170                 175

Asn Pro Ile Glu Tyr Ile Glu Met Arg Arg Lys Val Gly Gly Ala Pro
            180                 185                 190

Trp Ser Ala Asn Leu Val Glu His Ala Val Asp Ser Glu Val Pro Ala
        195                 200                 205

Ala Ile Ala Ser Ala Arg Pro Met Gln Val Leu Arg Asp Thr Phe Ser
210                 215                 220

Asp Ala Val His Leu Arg Asn Asp Leu Phe Ser Tyr Gln Arg Glu Val
225                 230                 235                 240

Gln Asp Glu Gly Glu Leu Ser Asn Ser Val Leu Val Phe Glu Lys Phe
                245                 250                 255

Leu Asp Cys Ser Thr Gln Asp Ala Ala Asp Thr Val Asn Asp Leu Leu
            260                 265                 270

Thr Ser Arg Leu His Gln Phe Glu His Thr Ala Leu Thr Glu Val Pro
        275                 280                 285

Ala Leu Leu Asp Glu Asn Gly Val Asp Pro Gln Gly Arg Leu Ala Val
290                 295                 300

Leu Gly Tyr Val Lys Gly Leu Gln Asp Trp Gln Ser Gly His Glu
305                 310                 315                 320

Trp His Ile Arg Ser Ser Arg Tyr Met Asn Glu Gly Leu Val Glu Gln
                325                 330                 335

Ser Ala Leu Ala Gly Gln Ser Ala Pro Gly Gln Pro Ala Leu Pro Gln
            340                 345                 350

Ser Ala Pro Asp Gly Thr Gly Pro Ala Thr Gln Pro Val Leu Gly Gly
        355                 360                 365

Pro Thr Gly Leu Gly Thr Ser Ala Ala Arg Ile Val Gln Ser Leu Leu
370                 375                 380

Ser Thr Ala Pro Gln Arg Ile Arg Ser Phe Thr His Thr Pro Tyr Glu
385                 390                 395                 400

Pro Ala Gly Pro Ile Arg Met Pro Glu Ile Tyr Met Pro Phe Asp Leu
                405                 410                 415

Ser Leu Ser Pro His Leu Asp Val Cys Arg Glu Asn Thr Ala Ala Trp
            420                 425                 430

Ala Arg Ala Met Gly Ile Phe Asp Asp Val Pro Arg Val Trp Asp Glu
        435                 440                 445

Asn Gln Met Arg Gly Tyr Asp Leu Pro Leu Cys Ser Ala Gly Leu Asp
450                 455                 460

Pro Asp Ala Thr Pro Glu Leu Asp Leu Ser Ala Ala Trp Leu Thr
465                 470                 475                 480

Trp Gly Thr Tyr Gly Asp Asp Tyr Tyr Pro Arg Val Phe Gly Arg Thr
                485                 490                 495

Leu Asp Met Ala Gly Ala Arg Ala Cys Asn Ala Arg Leu Lys Glu Leu
            500                 505                 510

Met Pro Val Glu Ser Ala Pro Ala Thr Ala Pro Val Thr Pro Leu Glu
        515                 520                 525

Arg Gly Leu Ala Asp Leu Trp Ala Arg Thr Ala Gly Pro Met Pro Val
530                 535                 540

Glu Thr Arg Arg Arg Phe Arg Ala Ala Val Asp Thr Met Ile Asp Ser
545                 550                 555                 560

Trp Leu Trp Glu Leu His Asn Gln His Leu Asn Arg Ile Pro Asp Pro

```
                        565                 570                 575
Val Asp Tyr Phe Glu Met Arg Arg Thr Phe Gly Ser Asp Leu Thr
                580                 585                 590

Ile Ser Leu Ala Lys Phe Ser His Gly Glu Ala Val Pro Pro Glu Ile
            595                 600                 605

Tyr Arg Thr Arg Thr Ile Arg Asn Met Glu Asn Ser Ala Ile Asp Tyr
            610                 615                 620

Ala Thr Met Leu Asn Asp Val Phe Ser Tyr Arg Lys Glu Ile Glu Tyr
625                 630                 635                 640

Glu Gly Glu Val His Asn Ala Val Leu Val Arg Asn Phe Leu Asp
                645                 650                 655

Cys Asp Gln Asp Arg Ala Phe Glu Ile Val Gly Asp Leu Met Thr Ala
                660                 665                 670

Arg Met Lys Gln Phe Gln Tyr Thr Val Asp Asp Glu Leu Pro Val Leu
            675                 680                 685

Cys Glu Asp Phe Gly Leu Ser Ser Glu Ser Arg Ala Val Leu Thr Arg
            690                 695                 700

Tyr Ala Asp Glu Leu Arg Asp Trp Met Ser Gly Ile Leu Asn Trp His
705                 710                 715                 720

Arg Glu Cys Val Arg Tyr Lys Asp Glu Asp Leu Arg His Asp Ala Val
                725                 730                 735

Ser Gln Gly Leu Ala Ala Leu Leu Arg Gly Pro Ser Gly Leu Gly Thr
                740                 745                 750

Ser Ala Val Glu Leu Arg
            755

<210> SEQ ID NO 24
<211> LENGTH: 732
<212> TYPE: PRT
<213> ORGANISM: Saccharopolyspora erythraea

<400> SEQUENCE: 24

Met Pro Ala Pro Gln Gln Arg Gln Pro Tyr Arg Leu Pro Ala Phe Tyr
1               5                   10                  15

Leu Pro Arg Pro Ala Arg Leu Asn Pro Asp Leu Glu Ala Ala Arg Ala
                20                  25                  30

Arg Ser Arg Arg Trp Ala Glu Glu Met Gly Met Leu Gly Ser Arg Ala
            35                  40                  45

Glu Pro Glu Gly Glu Gln Val Trp Thr Arg Glu Asp Phe Asp Arg His
        50                  55                  60

Asp Tyr Ala Leu Leu Cys Ala Tyr Ala His Pro Asp Ala Ser Ala Pro
65                  70                  75                  80

Ala Leu Glu Leu Ile Thr Gly Trp Tyr Val Trp Ala Phe Phe Asp
                85                  90                  95

Asp His Phe Leu Ala Arg Tyr Lys Arg Thr Gly Asp Val Asp Gly Ala
            100                 105                 110

Arg Ala His Leu Leu Gly Leu Ala Glu Leu Met Pro Val Gly Pro Ser
        115                 120                 125

Asp Ala Ala Pro Ala Ala Thr Gly Pro Val Glu Arg Gly Leu Ala Asp
    130                 135                 140

Leu Trp Val Arg Thr Ala Pro Glu Val Pro Ala Arg Trp Leu Val Arg
145                 150                 155                 160

Phe Ala Ala Ser Thr Arg Glu Leu Leu Glu Asn Arg Leu Arg Glu Leu
                165                 170                 175

Thr Gly Thr Ser Arg Cys Gly Val Pro Asn Pro Val Asp His Ile Ala
```

-continued

```
                180                 185                 190
Met Arg Arg Glu Ala Gly Gly Ala Ser Trp Ser Ala Ala Leu Val Glu
                195                 200                 205
Tyr Ala Ala Gly Ser Glu Val Pro Asp Val Val Ala Arg Ser Arg Pro
            210                 215                 220
Met Arg Val Leu Arg Asp Ser Phe Cys Asp Gly Val His Leu Arg Asn
225                 230                 235                 240
Asp Ile Phe Ser Tyr Pro Arg Glu Thr Ser Glu Glu Gly Glu Leu Gly
                245                 250                 255
Asn Gly Val Leu Val Val Glu Arg Phe Phe Asp Thr Asp Pro Gln Glu
            260                 265                 270
Ala Ala Asp Thr Val Asn Asp Leu Leu Thr Ser Arg Leu His Gln Phe
        275                 280                 285
Glu Asn Val Thr Leu Thr Glu Leu Pro Ala Met Phe Glu Glu His Gly
        290                 295                 300
Leu Ser Pro Val Glu Arg Ala Asp Val Leu Asp Tyr Val Lys Gly Leu
305                 310                 315                 320
Gln Asp Trp Gln Ser Gly Ala His Glu Trp His Leu Arg Ser Gly Arg
                325                 330                 335
Tyr Ala Val Pro Gly Gly Ala Glu Pro Arg Glu Pro Arg Arg Phe Leu
            340                 345                 350
Ser Gly Pro His Gly Leu Gly Thr Ser Ser His Leu Gly Ser Leu
        355                 360                 365
Leu Arg Thr Val Arg Pro Gly Leu Pro Ile Pro His Gly Gln Leu Arg
        370                 375                 380
Tyr Ala Arg Ile Ala Val Pro Ala Met Ser Ser Pro His Pro Val Arg
385                 390                 395                 400
Thr Asn Pro Gln Val Gly Thr Val Arg Ala His Ala Lys Glu Trp Ala
                405                 410                 415
Arg Arg Met Gly Met Leu Asp Gly Ser Gly Val Trp Thr Ala Asn Val
                420                 425                 430
Phe Asp Ala Ala Asp Phe Gly Gln Phe Ser Ala Met Ala His Pro Asp
            435                 440                 445
Ser Pro Gly Pro Glu Leu Glu Leu Val Asn Asp Trp His Val Trp Gly
        450                 455                 460
Trp Phe Phe Asp Asp Phe Phe Thr Glu Val Phe Lys Arg Ser Arg Asn
465                 470                 475                 480
Arg Ala Gly Ala Glu Ala Phe Leu Ala Arg Leu Pro Gly Phe Met Pro
                485                 490                 495
Ala Asp Thr Arg Arg Thr Pro Ala Pro Ala Asn Pro Val Glu Arg Gly
            500                 505                 510
Leu Ala Asp Leu Trp Ala Arg Ser Thr Pro Val Leu Ala Pro Arg Leu
        515                 520                 525
Arg Arg Arg Phe Pro Glu His Val Arg Asn Phe Val Gly Ser Trp Leu
        530                 535                 540
Trp Glu Leu Asp Asn Leu Ile Gln Asn Arg Val Ser Asp Pro Val Asp
545                 550                 555                 560
Tyr Leu Arg Met Arg Arg Thr Gly Gly Ser Ala Phe Arg Gly Ala
                565                 570                 575
Leu Ala Arg His Thr Leu Gly Ala Gly Leu Ala Pro Ala Val Phe Asp
            580                 585                 590
Thr Pro Glu Met Arg Ala Leu His Glu Asn Trp Ala Asp Val Gly Pro
        595                 600                 605
```

```
Leu Arg Asn Asp Leu Phe Ser Tyr His Lys Glu Val Asp Arg Glu Thr
        610                 615                 620

Glu Val Thr Asn Gly Val Leu Ala Val Gln Arg Phe Phe Asp Cys Gly
625                 630                 635                 640

Leu Gln Gln Ala Ala Ala Val Val Ala Asp Leu Ala Glu Val Arg Leu
            645                 650                 655

Arg Arg Phe Thr Ala Val Ala Glu Gln Glu Leu Pro Ala Leu Ala His
                660                 665                 670

Arg Phe Glu Pro Gly Arg Ala Pro Arg Glu Glu Leu Asp Arg Tyr Val
        675                 680                 685

Arg Gly Leu His Asp Trp Leu Ala Gly Glu Leu Ala Trp Ser Gln Val
    690                 695                 700

Thr Gly Arg Tyr Arg Glu Pro Ser Val Ser Ala Val Gly Ala Asp Leu
705                 710                 715                 720

Pro Ala Ala Pro Leu Gly Ile Thr Gly Ala Ala Gly
                725                 730

<210> SEQ ID NO 25
<211> LENGTH: 628
<212> TYPE: PRT
<213> ORGANISM: Nostoc punctiforme

<400> SEQUENCE: 25

Met Gln Pro Phe Glu Leu Pro Glu Phe Tyr Met Pro Trp Pro Ala Arg
1               5                   10                  15

Leu Asn Pro Asn Leu Glu Ala Ala Arg Ser His Ser Lys Ala Trp Ala
            20                  25                  30

Tyr Gln Met Gly Ile Leu Gly Ser Lys Glu Glu Ala Glu Ser Ser Val
        35                  40                  45

Ile Trp Asp Glu Arg Thr Phe Asp Ala His Asp Tyr Ala Leu Leu Cys
    50                  55                  60

Ser Tyr Thr His Pro Asp Ala Pro Gly Thr Glu Leu Asp Leu Val Thr
65                  70                  75                  80

Asp Trp Tyr Val Trp Val Phe Phe Asp Asp His Phe Leu Glu Ile
                85                  90                  95

Tyr Lys Arg Thr Gln Asp Met Ala Gly Ala Lys Glu Tyr Leu Gly Arg
            100                 105                 110

Leu Pro Met Phe Met Pro Ile Tyr Pro Thr Glu Thr Pro Pro Val Pro
        115                 120                 125

Thr Asn Pro Val Glu Cys Gly Leu Ala Asp Leu Trp Ser Arg Thr Ala
130                 135                 140

Phe Thr Lys Ser Val Asp Trp Arg Leu Arg Phe Phe Glu Ser Thr Lys
145                 150                 155                 160

Asn Leu Leu Glu Glu Ser Leu Trp Glu Leu Ala Asn Ile Asn Gln Asp
                165                 170                 175

Arg Val Ala Asn Pro Ile Glu Tyr Ile Glu Met Arg Arg Lys Val Gly
            180                 185                 190

Gly Ala Pro Trp Ser Ala Asp Leu Val Glu His Ala Val Phe Ile Glu
        195                 200                 205

Ile Pro Ala Asp Ile Ala Ser Thr Arg Pro Met Arg Val Leu Lys Asp
    210                 215                 220

Thr Phe Ala Asp Gly Val His Leu Arg Asn Asp Leu Phe Ser Tyr Gln
225                 230                 235                 240

Arg Glu Val Glu Asp Glu Gly Glu Asn Ala Asn Cys Val Leu Val Leu
                245                 250                 255
```

```
Glu Arg Phe Leu Asn Val Ser Thr Gln Glu Ala Ala Asn Leu Thr Asn
        260                 265                 270

Glu Leu Leu Thr Ser Arg Leu Tyr Gln Phe Asp Asn Thr Ala Val Thr
        275                 280                 285

Glu Leu Pro Pro Leu Phe Glu Glu Tyr Gly Leu Asp Pro Val Ala Arg
        290                 295                 300

Val Asn Val Leu Leu Tyr Ile Lys Gly Leu Gln Asp Trp Gln Ser Gly
305                 310                 315                 320

Gly His Glu Trp His Met Arg Ser Ser Arg Tyr Met Asn Lys Gly Gly
                325                 330                 335

Asp Asn Ser Pro Thr Ser Thr Val Leu Gly Gly Pro Thr Gly Leu Gly
        340                 345                 350

Thr Ser Ala Ala Arg Ile Glu Ser Leu Tyr Ala Ala Leu Gly Leu Gly
        355                 360                 365

Arg Ile Lys Ser Phe Thr His Val Pro Tyr Gln Pro Val Gly Pro Val
        370                 375                 380

Thr Leu Pro Lys Phe Tyr Met Pro Phe Thr Thr Ser Leu Asn Pro His
385                 390                 395                 400

Leu Asn Ala Ala Arg Lys His Ser Lys Glu Trp Ala Arg Gln Met Gly
                405                 410                 415

Met Leu Glu Ser Leu Pro Gly Ile Pro Asp Ala Val Ile Trp Asp Asp
                420                 425                 430

His Lys Phe Asp Val Ala Asp Val Ala Leu Cys Gly Ala Leu Ile His
                435                 440                 445

Pro Asn Gly Ser Gly Leu Glu Leu Asn Leu Thr Ala Cys Trp Leu Val
        450                 455                 460

Trp Gly Thr Tyr Ala Asp Asp Tyr Phe Pro Ala Leu Tyr Gly Asn Asn
465                 470                 475                 480

Arg Asn Met Ala Gly Ala Lys Val Phe Asn Ala Arg Leu Ser Ala Phe
                485                 490                 495

Met Pro Leu Asp Asp Ser Thr Pro Ser Glu Val Pro Thr Asn Pro Val
        500                 505                 510

Glu Ala Gly Leu Ala Asp Ile Trp Ser Arg Thr Ala Gly Pro Met Ser
        515                 520                 525

Ala Asn Ala Arg Thr Gln Phe Arg Arg Ala Ile Gln Asp Met Thr Asp
        530                 535                 540

Ser Trp Val Trp Glu Leu Ala Asn Gln Ile Gln Asn Arg Ile Pro Asp
545                 550                 555                 560

Pro Ile Asp Tyr Val Glu Met Arg Arg Lys Thr Phe Gly Ser Asp Leu
                565                 570                 575

Thr Met Ser Leu Ser Arg Leu Ala Gln Gly Ser Glu Ile Pro Gln Glu
                580                 585                 590

Ile Tyr Arg Thr Arg Thr Met Arg Ser Leu Asp Asn Ser Ala Ala Asp
        595                 600                 605

Phe Ala Cys Leu Thr Asn Asp Val Phe Ser Tyr Gln Lys Glu Ile Glu
        610                 615                 620

Phe Glu Gly Ile
625

<210> SEQ ID NO 26
<211> LENGTH: 630
<212> TYPE: PRT
<213> ORGANISM: Nostoc punctiforme

<400> SEQUENCE: 26
```

```
Met Gln Pro Phe Glu Leu Pro Glu Phe Tyr Met Pro Trp Pro Ala Arg
  1               5                  10                 15
Leu Asn Pro Asn Leu Glu Ala Ala Arg Ser His Ser Lys Ala Trp Ala
             20                  25                  30
Tyr Gln Met Gly Ile Leu Gly Ser Lys Glu Glu Ala Glu Ser Ser Val
         35                  40                  45
Ile Trp Asp Glu Arg Thr Phe Asp Ala His Asp Tyr Ala Leu Leu Cys
 50                  55                  60
Ser Tyr Thr His Pro Asp Ala Pro Gly Thr Glu Leu Asp Leu Val Thr
 65              70                  75                      80
Asp Trp Tyr Val Trp Val Phe Phe Asp Asp His Phe Leu Glu Ile
                 85                  90                  95
Tyr Lys Arg Thr Gln Asp Met Ala Gly Ala Lys Glu Tyr Leu Gly Arg
                100                 105                 110
Leu Pro Met Phe Met Pro Ile Tyr Pro Thr Glu Thr Pro Pro Val Pro
            115                 120                 125
Thr Asn Pro Val Glu Cys Gly Leu Ala Asp Leu Trp Ser Arg Thr Ala
        130                 135                 140
Phe Thr Lys Ser Val Asp Trp Arg Leu Arg Phe Phe Glu Ser Thr Lys
145                 150                 155                 160
Asn Leu Leu Glu Glu Ser Leu Trp Glu Leu Ala Asn Ile Asn Gln Asp
                165                 170                 175
Arg Val Ala Asn Pro Ile Glu Tyr Ile Glu Met Arg Arg Lys Val Gly
            180                 185                 190
Gly Ala Pro Trp Ser Ala Asp Leu Val Glu His Ala Val Phe Ile Glu
        195                 200                 205
Ile Pro Ala Asp Ile Ala Ser Thr Arg Pro Met Arg Val Leu Lys Asp
210                 215                 220
Thr Phe Ala Asp Gly Val His Leu Arg Asn Asp Leu Phe Ser Tyr Gln
225                 230                 235                 240
Arg Glu Val Glu Asp Glu Gly Glu Asn Ala Asn Cys Val Leu Val Leu
                245                 250                 255
Glu Arg Phe Leu Asn Val Ser Thr Gln Glu Ala Ala Asn Leu Thr Asn
            260                 265                 270
Glu Leu Leu Thr Ser Arg Leu Tyr Gln Phe Asp Asn Thr Ala Val Thr
        275                 280                 285
Glu Leu Pro Pro Leu Phe Glu Glu Tyr Gly Leu Asp Pro Val Ala Arg
        290                 295                 300
Val Asn Val Leu Leu Tyr Ile Lys Gly Leu Gln Asp Trp Gln Ser Gly
305                 310                 315                 320
Gly His Glu Trp His Met Arg Ser Ser Arg Tyr Met Asn Lys Gly Gly
                325                 330                 335
Asp Asn Ser Pro Thr Ser Thr Val Leu Gly Gly Pro Thr Gly Leu Gly
            340                 345                 350
Thr Ser Ala Ala Arg Ile Glu Ser Leu Tyr Ala Ala Leu Gly Leu Gly
        355                 360                 365
Arg Ile Lys Ser Phe Thr His Val Pro Tyr Gln Pro Val Gly Pro Val
370                 375                 380
Thr Leu Pro Lys Phe Tyr Met Pro Phe Thr Thr Ser Leu Asn Pro His
385                 390                 395                 400
Leu Asn Ala Ala Arg Lys His Ser Lys Glu Trp Ala Arg Gln Met Gly
            405                 410                 415
Met Leu Glu Ser Leu Pro Gly Ile Pro Asp Ala Val Ile Trp Asp Asp
        420                 425                 430
```

```
His Lys Phe Asp Val Ala Asp Val Ala Leu Cys Gly Ala Leu Ile His
            435                 440                 445

Pro Asn Gly Ser Gly Leu Glu Leu Asn Leu Thr Ala Cys Trp Leu Val
    450                 455                 460

Trp Gly Thr Tyr Ala Asp Asp Tyr Phe Pro Ala Leu Tyr Gly Asn Asn
465                 470                 475                 480

Arg Asn Met Ala Gly Ala Lys Val Phe Asn Ala Arg Leu Ser Ala Phe
                485                 490                 495

Met Pro Leu Asp Asp Ser Thr Pro Ser Glu Val Pro Thr Asn Pro Val
                500                 505                 510

Glu Ala Gly Leu Ala Asp Ile Trp Ser Arg Thr Ala Gly Pro Met Ser
            515                 520                 525

Ala Asn Ala Arg Thr Gln Phe Arg Arg Ala Ile Gln Asp Met Thr Asp
            530                 535                 540

Ser Trp Val Trp Glu Leu Ala Asn Gln Ile Gln Asn Arg Ile Pro Asp
545                 550                 555                 560

Pro Ile Asp Tyr Val Glu Met Arg Arg Lys Thr Phe Gly Ser Asp Leu
                565                 570                 575

Thr Met Ser Leu Ser Arg Leu Ala Gln Gly Ser Glu Ile Pro Gln Glu
                580                 585                 590

Ile Tyr Arg Thr Arg Thr Met Arg Ser Leu Asp Asn Ser Ala Ala Asp
            595                 600                 605

Phe Ala Cys Leu Thr Asn Asp Ile Leu Phe Leu Ser Glu Arg Asn Arg
            610                 615                 620

Ile Arg Gly Arg Asn Pro
625                 630

<210> SEQ ID NO 27
<211> LENGTH: 725
<212> TYPE: PRT
<213> ORGANISM: Streptomyces coelicolor

<400> SEQUENCE: 27

Thr Gln Gln Pro Phe Gln Leu Pro His Phe Tyr Leu Pro His Pro Ala
1               5                   10                  15

Arg Leu Asn Pro His Leu Asp Glu Ala Arg Ala His Ser Thr Thr Trp
            20                  25                  30

Ala Arg Glu Met Gly Met Leu Glu Gly Ser Gly Val Trp Glu Gln Ser
        35                  40                  45

Asp Leu Glu Ala His Asp Tyr Gly Leu Leu Cys Ala Tyr Thr His Pro
    50                  55                  60

Asp Cys Asp Gly Pro Ala Leu Ser Leu Ile Thr Asp Trp Tyr Val Trp
65                  70                  75                  80

Val Phe Phe Phe Asp Asp His Phe Leu Glu Lys Tyr Lys Arg Ser Gln
                85                  90                  95

Asp Arg Leu Ala Gly Lys Ala His Leu Asp Arg Leu Pro Leu Phe Met
            100                 105                 110

Pro Leu Asp Asp Ala Ala Gly Met Pro Glu Pro Arg Asn Pro Val Glu
        115                 120                 125

Ala Gly Leu Ala Asp Leu Trp Thr Arg Thr Val Pro Ala Met Ser Ala
    130                 135                 140

Asp Trp Arg Arg Arg Phe Ala Val Ala Thr Glu His Leu Leu Asn Glu
145                 150                 155                 160

Ser Met Trp Glu Leu Ser Asn Ile Asn Glu Gly Arg Val Ala Asn Pro
                165                 170                 175
```

-continued

Val Glu Tyr Ile Glu Met Arg Arg Lys Val Gly Gly Ala Pro Trp Ser
            180                 185                 190

Ala Gly Leu Val Glu Tyr Ala Thr Ala Glu Val Pro Ala Ala Val Ala
        195                 200                 205

Gly Thr Arg Pro Leu Arg Val Leu Met Glu Thr Phe Ser Asp Ala Val
    210                 215                 220

His Leu Arg Asn Asp Leu Phe Ser Tyr Gln Arg Glu Val Glu Asp Glu
225                 230                 235                 240

Gly Glu Leu Ser Asn Gly Val Leu Val Leu Glu Thr Phe Phe Gly Cys
                245                 250                 255

Thr Thr Gln Glu Ala Ala Asp Leu Val Asn Asp Val Leu Thr Ser Arg
            260                 265                 270

Leu His Gln Phe Glu His Thr Ala Phe Thr Glu Val Pro Ala Val Ala
        275                 280                 285

Leu Glu Lys Gly Leu Thr Pro Leu Glu Val Ala Ala Val Gly Ala Tyr
    290                 295                 300

Thr Lys Gly Leu Gln Asp Trp Gln Ser Gly Gly His Glu Trp His Met
305                 310                 315                 320

Arg Ser Ser Arg Tyr Met Asn Lys Gly Glu Arg Pro Leu Ala Gly Trp
                325                 330                 335

Gln Ala Leu Thr Gly Pro Gly Thr Ser Ala Ala Asp Val Gly Ala Leu
            340                 345                 350

Leu Ala Asp Ala Val Ala Gln Arg Ala Arg Ser Tyr Thr Tyr Val Pro
        355                 360                 365

Phe Gln Lys Val Gly Pro Ser Val Ile Pro Asp Ile Arg Met Pro Tyr
    370                 375                 380

Pro Leu Glu Leu Ser Pro Ala Leu Asp Gly Ala Arg Arg His Leu Ser
385                 390                 395                 400

Glu Trp Cys Arg Glu Met Gly Ile Leu Ser Glu Gly Val Trp Asp Glu
                405                 410                 415

Asp Lys Leu Glu Ser Cys Asp Leu Pro Leu Cys Ala Ala Gly Leu Asp
            420                 425                 430

Pro Asp Ala Thr Gln Asp Gln Leu Asp Leu Ala Ser Gly Trp Leu Ala
        435                 440                 445

Phe Gly Thr Tyr Gly Asp Asp Tyr Tyr Pro Leu Val Tyr Gly His Arg
    450                 455                 460

Arg Asp Leu Ala Ala Ala Arg Leu Thr Thr Arg Leu Ser Asp Cys
465                 470                 475                 480

Met Pro Leu Asp Gly Glu Pro Val Pro Pro Gly Asn Ala Met Glu
                485                 490                 495

Arg Ser Leu Ile Asp Leu Trp Val Arg Thr Thr Ala Gly Met Thr Pro
            500                 505                 510

Glu Glu Arg Arg Pro Leu Lys Lys Ala Val Asp Asp Met Thr Glu Ala
        515                 520                 525

Trp Leu Trp Glu Leu Ser Asn Gln Ile Gln Asn Arg Val Pro Asp Pro
    530                 535                 540

Val Asp Tyr Leu Glu Met Arg Arg Ala Thr Phe Gly Ser Asp Leu Thr
545                 550                 555                 560

Leu Gly Leu Cys Arg Ala Gly His Gly Pro Ala Val Pro Pro Glu Val
                565                 570                 575

Tyr Arg Ser Gly Pro Val Arg Ser Leu Glu Asn Ala Ala Ile Asp Tyr
            580                 585                 590

Ala Cys Leu Leu Asn Asp Val Phe Ser Tyr Gln Lys Glu Ile Glu Tyr

-continued

```
                595                 600                 605
Glu Gly Glu Ile His Asn Ala Val Leu Val Gln Asn Phe Phe Gly
        610                 615                 620

Val Asp Tyr Pro Ala Ala Leu Gly Val Val Gln Asp Leu Met Asn Gln
625                 630                 635                 640

Arg Met Arg Gln Phe Glu His Val Val Ala His Glu Leu Pro Val Val
                645                 650                 655

Tyr Asp Asp Phe Gln Leu Ser Glu Glu Ala Arg Thr Val Met Arg Gly
                660                 665                 670

Tyr Val Thr Asp Leu Gln Asn Trp Met Ala Gly Ile Leu Asn Trp His
                675                 680                 685

Arg Asn Val Pro Arg Tyr Lys Ala Glu Tyr Leu Ala Gly Arg Thr His
        690                 695                 700

Gly Phe Leu Pro Asp Arg Ile Pro Ala Pro Val Pro Arg Ser Ser
705                 710                 715                 720

Pro Ala Leu Thr His
                725

<210> SEQ ID NO 28
<211> LENGTH: 725
<212> TYPE: PRT
<213> ORGANISM: Streptomyces avermitilis

<400> SEQUENCE: 28

Met Thr Gln Pro Phe Gln Leu Pro His Phe Tyr Met Pro Tyr Pro Ala
1               5                   10                  15

Arg Leu Asn Pro His Leu Asp Glu Ala Arg Ala His Ser Thr Arg Trp
                20                  25                  30

Ala Arg Gly Met Gly Met Leu Glu Gly Ser Gly Ile Trp Glu Gln Ser
            35                  40                  45

Asp Leu Asp Ala His Asp Tyr Gly Leu Leu Cys Ala Tyr Thr His Pro
        50                  55                  60

Asp Cys Asp Gly Pro Ala Leu Ser Leu Ile Thr Asp Trp Tyr Val Trp
65                  70                  75                  80

Val Phe Phe Phe Asp Asp His Phe Leu Glu Thr Phe Lys Arg Thr Gln
                85                  90                  95

Asp Arg Glu Gly Gly Lys Ala Tyr Leu Asp Arg Leu Pro Leu Phe Met
                100                 105                 110

Pro Leu Asp Leu Ser Ala Pro Val Pro Glu Pro Glu Asn Pro Val Glu
            115                 120                 125

Ala Gly Leu Ala Asp Leu Trp Ala Arg Thr Val Pro Ala Met Ser Ala
        130                 135                 140

Asp Trp Arg Lys Arg Phe Ala Val Ser Thr Glu His Leu Leu Asn Glu
145                 150                 155                 160

Ser Leu Trp Glu Leu Ser Asn Ile Asn Glu Gly Arg Ile Ala Asn Pro
                165                 170                 175

Val Glu Tyr Ile Glu Met Arg Arg Lys Val Gly Gly Ala Pro Trp Ser
                180                 185                 190

Ala Gly Leu Val Glu Tyr Ala Thr Ala Glu Val Pro Ala Ala Val Ala
            195                 200                 205

Gly Ser Arg Pro Leu Arg Val Leu Met Glu Thr Phe Ser Asp Gly Val
        210                 215                 220

His Leu Arg Asn Asp Leu Phe Ser Tyr Gln Arg Glu Val Glu Glu Glu
225                 230                 235                 240

Gly Glu Leu Ser Asn Gly Val Leu Val Leu Glu Thr Phe Phe Gly Cys
```

-continued

```
                    245                 250                 255
Thr Thr Gln Glu Ala Ala Glu Thr Val Asn Asp Ile Leu Thr Ser Arg
                260                 265                 270

Leu His Gln Phe Glu His Thr Ala Leu Thr Glu Val Pro Ala Leu Ala
            275                 280                 285

Leu Glu Lys Gly Leu Thr Pro Pro Glu Val Ala Ala Val Ala Ala Tyr
        290                 295                 300

Ala Arg Gly Leu Gln Asp Trp Gln Ser Gly His Glu Trp His Leu
305                 310                 315                 320

Arg Ser Ser Arg Tyr Met Asn Glu Gly Ala Leu Ser Gln Lys Arg Pro
                325                 330                 335

Phe Gly Leu Ser Ala Ile Gly Thr Ser Ala Ala Asp Leu Arg Gly Leu
            340                 345                 350

Leu Ala Asp Ala Gly Ala Glu Arg Leu Arg Arg Tyr Thr His Val Pro
        355                 360                 365

Phe Gln Lys Val Gly Pro Ser Arg Ile Pro Asp Phe His Met Pro Phe
    370                 375                 380

Gln Val Glu Leu Ser Pro His Leu Gly Ala Arg Ala Arg Leu Thr
385                 390                 395                 400

Pro Trp Met His Ser Thr Gly Met Leu Gln Glu Gly Val Trp Asp Glu
                405                 410                 415

Asp Lys Leu Thr Ala Tyr Asp Leu Pro Leu Cys Ser Ala Gly Leu Asp
            420                 425                 430

Pro Asp Ala Thr Pro Asp Glu Leu Asp Leu Ser Ser Arg Trp Leu Ala
        435                 440                 445

Trp Gly Thr Tyr Gly Asp Asp Tyr Tyr Pro Met Val Phe Gly Pro Arg
    450                 455                 460

Arg Asp Leu Ala Ala Lys Leu Cys Thr Arg Arg Leu Ser Ala Cys
465                 470                 475                 480

Met Pro Val Asp Gly Glu Val Pro Ala Pro Val Asn Gly Met Glu
                485                 490                 495

Arg Gly Leu Ile Asp Leu Trp Ala Ile Thr Thr Ala Glu Met Thr Pro
            500                 505                 510

Asp Glu Arg Arg Thr Phe Arg Ala Ser Val Asp Val Met Thr Glu Ser
        515                 520                 525

Trp Val Trp Glu Leu Ser Asn Gln Leu Gln His Arg Ile Pro Asp Pro
    530                 535                 540

Ile Asp Tyr Leu Glu Met Arg Arg Ala Thr Phe Gly Ala Asp Leu Thr
545                 550                 555                 560

Leu Ser Leu Cys Arg Val Gly His Gly Pro Lys Val Pro Pro Glu Ile
                565                 570                 575

Tyr Arg Ser Gly Pro Val Arg Ser Leu Glu Asn Ala Ala Val Asp Tyr
            580                 585                 590

Gly Met Leu Ile Asn Asp Val Phe Ser Tyr Gln Lys Glu Ile Glu Tyr
        595                 600                 605

Glu Gly Glu Val His Asn Ala Ile Leu Val Val Gln Asn Phe Phe Gly
    610                 615                 620

Cys Asp Tyr Pro Thr Ala Leu Gly Val Ile Asn Asp Leu Met Thr Gln
625                 630                 635                 640

Arg Met His Gln Phe Glu His Val Ala Ala His Glu Leu Pro Leu Leu
                645                 650                 655

Tyr Lys Asp Phe Lys Leu Pro Gln Glu Val Arg Asp Ile Met Asp Gly
            660                 665                 670
```

```
Tyr Val Val Glu Leu Gln Asn Trp Met Ser Gly Ile Leu Lys Trp His
        675                 680                 685

Gln Asp Cys His Arg Tyr Gly Ala Ala Asp Leu Ala Arg Arg Ala His
    690                 695                 700

Gly Phe Val Pro Asp Arg Ala Pro Ser Ala Pro Phe Thr Ala Trp Ala
705                 710                 715                 720

Ala Pro Val Ala Arg
            725

<210> SEQ ID NO 29
<211> LENGTH: 314
<212> TYPE: PRT
<213> ORGANISM: Streptomyces sp.

<400> SEQUENCE: 29

Met Pro Glu Pro Asp Pro Val Arg Val Glu Val Ser Arg Arg Ile
1               5                   10                  15

Lys Glu Trp Ala Val Asp Glu Val Glu Leu Tyr Pro Pro Glu Trp Glu
            20                  25                  30

Asp Gln Phe Asp Gly Phe Ser Val Gly Arg Tyr Met Val Ala Cys His
        35                  40                  45

Pro Asp Ala Pro Thr Val Asp His Leu Met Ile Ala Thr Arg Leu Met
    50                  55                  60

Val Ala Glu Asn Val Val Asp Asp Cys Tyr Cys Glu Asp His Gly Gly
65                  70                  75                  80

Ser Pro Val Gly Leu Gly Gly Arg Leu Leu Leu Ala His Thr Ala Leu
                85                  90                  95

Asp Ala Leu His Thr Thr Arg Glu Tyr Ala Pro Asp Trp Glu Glu Ser
            100                 105                 110

Leu His Ser Asp Ala Pro Arg Ala Tyr Arg Ser Ala Met Glu Tyr
        115                 120                 125

Phe Thr Arg Glu Ala Thr Ala Ser Gln Ala Asp Arg Tyr Arg His Asp
    130                 135                 140

Met Ala Arg Leu His Leu Gly Tyr Leu Ala Glu Ala Ala Trp Ala Gln
145                 150                 155                 160

Thr Asp Tyr Val Pro Gln Val Trp Glu Tyr Leu Ala Met Arg Gln Phe
                165                 170                 175

Asn Asn Phe Arg Pro Cys Pro Thr Ile Thr Asp Thr Val Gly Gly Tyr
            180                 185                 190

Glu Leu Pro Ala Asp Leu His Ala Gln Ala Ala Val Gln Arg Val Ile
        195                 200                 205

Ala Leu Ala Gly Asn Ala Thr Thr Ile Val Asn Asp Leu Tyr Ser Tyr
    210                 215                 220

Thr Lys Glu Leu Ala Ser Pro Gly Arg His Leu Asn Leu Pro Val Val
225                 230                 235                 240

Val Ala Glu His Glu Gly Gly Asp Val Arg Asp Ala Tyr Leu Lys Ala
                245                 250                 255

Val Glu Val His Asn Asp Leu Met His Ala Phe Glu Ala Glu Ala Ala
            260                 265                 270

Glu Leu Ala Ala Ala Cys Pro Val Pro Ser Val Leu Arg Phe Leu Arg
        275                 280                 285

Gly Val Ala Ala Trp Val Asp Gly Asn His Tyr Trp His Gln Thr Asn
    290                 295                 300

Thr Tyr Arg Tyr Ser Leu Pro Asp Phe Trp
305                 310
```

```
<210> SEQ ID NO 30
<211> LENGTH: 440
<212> TYPE: PRT
<213> ORGANISM: Streptomyces ambofaciens

<400> SEQUENCE: 30

Met Pro Asp Ser Gly Pro Leu Gly Pro His Ser Pro Asp His Arg Pro
 1               5                   10                  15

Thr Pro Ala Thr Thr Val Pro Asp Ala Pro Ala Ser Lys Pro Pro Asp
             20                  25                  30

Val Ala Val Thr Pro Thr Ala Ser Glu Phe Leu Ala Ala Leu His Pro
         35                  40                  45

Pro Val Pro Ile Pro Ser Pro Ser Pro Ser Gly Ser Ala Ser Ala
     50                  55                  60

Ala Ala Asp Thr Pro Asp Ala Thr Thr Val Gly Ser Ala Leu Gln Arg
65                  70                  75                  80

Ile Leu Arg Gly Pro Thr Gly Pro Gly Thr Ala Ala Leu Ala Leu Ser
                 85                  90                  95

Val Arg His Asp Pro Pro Ser Leu Pro Gly Ser Pro Ala Pro Ala Glu
            100                 105                 110

Pro Ala Ala Gly Arg Ala Val Pro Gly Leu Tyr His His Pro Val Pro
        115                 120                 125

Glu Pro Asp Pro Ala Arg Val Glu Glu Val Ser Arg Arg Ile Lys Arg
130                 135                 140

Trp Ala Glu Asp Glu Val Gln Leu Tyr Pro Glu Asp Trp Gly Gly Glu
145                 150                 155                 160

Phe Asp Gly Phe Ser Val Gly Arg Tyr Met Val Ala Cys His Pro Asp
                165                 170                 175

Ala Pro Thr Val Asp His Leu Met Leu Ala Thr Arg Leu Met Val Ala
            180                 185                 190

Glu Asn Ala Val Asp Asp Cys Tyr Cys Glu Asp His Gly Gly Ser Pro
        195                 200                 205

Val Gly Leu Gly Gly Arg Leu Leu Ala His Thr Ala Ile Asp Pro
210                 215                 220

Phe His Thr Thr Ala Glu Tyr Ala Pro Pro Trp Arg Glu Ser Leu Thr
225                 230                 235                 240

Ser Asp Ala Pro Arg Arg Ala Tyr Arg Ser Ala Met Asp Tyr Phe Val
                245                 250                 255

Arg Ala Ala Thr Pro Ser Gln Ala Asp Arg Tyr Arg His Asp Met Ala
            260                 265                 270

Arg Leu His Leu Gly Tyr Leu Ala Glu Ala Ala Trp Ala Gln Thr Asp
        275                 280                 285

His Val Pro Glu Val Trp Glu Tyr Leu Ala Met Arg Gln Phe Asn Asn
290                 295                 300

Phe Arg Pro Cys Pro Thr Ile Thr Asp Thr Val Gly Gly Tyr Glu Leu
305                 310                 315                 320

Pro Ala Asp Leu His Ala Arg Pro Asp Met Gln Arg Val Ile Ala Leu
                325                 330                 335

Ala Gly Asn Ala Thr Thr Ile Val Asn Asp Leu Tyr Ser Tyr Thr Lys
            340                 345                 350

Glu Leu Asp Ser Pro Gly Arg His Leu Asn Leu Pro Val Val Ile Ala
        355                 360                 365

Glu Arg Glu Arg Leu Ser Glu Arg Asp Ala Tyr Leu Lys Ala Val Glu
370                 375                 380
```

```
Val His Asn Glu Leu Gln His Ala Phe Glu Ala Ala Ala Glu Leu
385                 390                 395                 400

Ala Lys Ala Cys Pro Leu Pro Thr Val Leu Arg Phe Leu Lys Gly Val
            405                 410                 415

Ala Ala Trp Val Asp Gly Asn His Asp Trp His Arg Thr Asn Thr Tyr
        420                 425                 430

Arg Tyr Ser Leu Pro Asp Phe Trp
        435                 440

<210> SEQ ID NO 31
<211> LENGTH: 367
<212> TYPE: PRT
<213> ORGANISM: Streptomyces scabies

<400> SEQUENCE: 31

Asp Asp Ala Leu Arg Ile Leu Arg Ala Pro Thr Gly Pro Gly Thr
1               5                   10                  15

Ala Ser Leu Val Val Ala Asp Arg Phe Ala Pro Pro Leu Pro Ser Pro
            20                  25                  30

Val Ser Arg Ala Pro Val Glu Pro Ala Ala Gly Arg Ala Val Pro Gly
        35                  40                  45

Leu Tyr His His Pro Val Pro Glu Pro Asp Pro Val Arg Val Glu Glu
    50                  55                  60

Val Ser Arg Arg Ile Lys Arg Trp Ala Glu Glu Val Gln Leu Tyr
65                  70                  75                  80

Pro Glu Glu Trp Glu Gly Gln Phe Asp Gly Phe Ser Val Gly Arg Tyr
                85                  90                  95

Met Val Ala Cys His Pro Asp Ala Pro Thr Thr Asp His Leu Met Leu
            100                 105                 110

Ala Thr Arg Leu Met Val Ala Glu Asn Ala Val Asp Asp Cys Tyr Cys
        115                 120                 125

Glu Asp His Gly Gly Ser Pro Val Gly Leu Gly Arg Leu Leu Leu
                135                 140

Ala His Thr Ala Leu Asp His Phe His Thr Thr Ala Glu Tyr Ala Pro
145                 150                 155                 160

Ala Trp Gln Glu Ser Leu Ala Ser Asp Ala Pro Arg Arg Ala Tyr Arg
            165                 170                 175

Ser Ala Met Asp His Phe Val Gly Ala Ala Thr Pro Ser Gln Ala Asp
        180                 185                 190

Arg Tyr Arg His Asp Met Ala Arg Leu His Leu Gly Tyr Leu Ala Glu
    195                 200                 205

Ala Ala Trp Ala Gln Thr Gly His Val Pro Glu Val Trp Glu Tyr Leu
210                 215                 220

Ala Met Arg Gln Phe Asn Asn Phe Arg Pro Cys Pro Thr Ile Thr Asp
225                 230                 235                 240

Thr Val Gly Gly Tyr Glu Leu Pro Ala Asp Leu His Ala Arg Pro Asp
                245                 250                 255

Met Gln Arg Val Ile Ala Leu Ala Gly Asn Ala Thr Thr Ile Val Asn
            260                 265                 270

Asp Leu Tyr Ser Tyr Thr Lys Glu Leu Asp Ser Pro Gly His His Leu
        275                 280                 285

Asn Leu Pro Val Val Ile Ala Glu Arg Glu Arg Leu Pro Val Arg Asp
    290                 295                 300

Ala Tyr Leu Lys Ala Val Glu Val His Asn Glu Leu Gln His Ala Phe
305                 310                 315                 320
```

```
Glu Ala Ala Ser Ala Glu Leu Ala Glu Ala Cys Pro Leu Pro Ala Val
            325                 330                 335

Leu Arg Phe Leu Lys Gly Val Ala Ala Trp Val Asp Gly Asn His Asp
        340                 345                 350

Trp His Arg Thr Asn Thr Tyr Arg Tyr Thr Leu Pro Asp Phe Trp
        355                 360                 365

<210> SEQ ID NO 32
<211> LENGTH: 437
<212> TYPE: PRT
<213> ORGANISM: Streptomyces griseus

<400> SEQUENCE: 32

Met Pro Val Pro Glu Leu Pro Pro Arg Ser Ser Leu Pro Glu Ala
 1               5                  10                  15

Val Thr Arg Phe Gly Ala Ser Val Leu Gly Ala Val Ala Arg Ala
            20                  25                  30

His Asp Ser Glu Ala Thr Val Gly Gly Pro Ser Gly Gly Arg Pro Leu
        35                  40                  45

Pro Ser Pro Pro Ala Gly Leu Ser Phe Gly Pro Pro Ser Pro Ala Ala
 50                  55                  60

Pro Ser Ala Asp Val Pro Ala Pro Glu Ala Pro Gly Arg Gly Ala Asp
 65                  70                  75                  80

Leu Glu Arg Leu Leu Cys Gly Pro His Gly Leu Gly Thr Ala Gly Leu
                 85                  90                  95

Arg Leu Thr Pro Gly Lys Glu Arg Pro Val Pro Ala Thr Ala Arg Glu
            100                 105                 110

Gly Arg Pro Ile Pro Gly Leu Tyr His His Pro Val Pro Glu Pro Asp
        115                 120                 125

Glu Ala Arg Val Glu Glu Val Ser Arg Arg Ile Lys Ala Trp Ala Leu
130                 135                 140

Asp Glu Val Ser Leu Tyr Pro Glu Glu Trp Glu Gln Phe Asp Gly
145                 150                 155                 160

Phe Ser Val Gly Arg Tyr Met Val Gly Cys His Pro Asp Ala Pro Thr
                165                 170                 175

Val Asp His Leu Met Leu Ala Thr Arg Leu Met Val Ala Glu Asn Ala
            180                 185                 190

Val Asp Asp Cys Tyr Cys Glu Asp His Gly Ser Pro Val Gly Leu
                195                 200                 205

Gly Glu Arg Leu Leu Leu Ala His Thr Ala Leu Asp Pro Leu Tyr Thr
    210                 215                 220

Ala Arg Glu Tyr Gln Pro Gly Trp Ala Ala Ser Leu His Ala Asp Ala
225                 230                 235                 240

Pro Arg Arg Ala Tyr Arg Ser Ala Met Asp Tyr Phe Val Arg Ala Ala
                245                 250                 255

Gly Pro Ser Gln Ala Asp Arg Leu Arg His Asp Met Ala Arg Leu His
            260                 265                 270

Leu Gly Tyr Leu Ala Glu Ala Ala Trp Ala Gln Gln Asp Gln Val Pro
        275                 280                 285

Glu Val Trp Glu Tyr Leu Ala Met Arg Gln Phe Asn Asn Phe Arg Pro
    290                 295                 300

Cys Pro Thr Ile Thr Asp Thr Val Gly Gly Tyr Glu Leu Pro Ala Asp
305                 310                 315                 320

Leu His Ala Gln Ala Ala Met Gln Lys Val Ile Ala Leu Ala Ser Asn
                325                 330                 335
```

```
Ala Thr Thr Ile Val Asn Asp Leu Tyr Ser Tyr Thr Lys Glu Leu Ala
            340                 345                 350

Ala Pro Gly Arg His Leu Asn Leu Pro Val Val Ile Ala Glu Arg Glu
            355                 360                 365

Gly Leu Ser Asp Gln Asp Ala Tyr Leu Lys Ser Val Glu Ile His Asn
            370                 375                 380

Glu Leu Met His Ala Phe Glu Ser Glu Ala Ala Leu Ala Ala Ala
385                 390                 395                 400

Cys Pro Val Pro Ser Val Gln Arg Phe Leu Arg Gly Val Ala Ala Trp
                405                 410                 415

Val Asp Gly Asn His His Trp His Arg Ser Asn Thr Tyr Arg Tyr Ser
            420                 425                 430

Leu Pro Asp Phe Trp
            435
```

<210> SEQ ID NO 33
<211> LENGTH: 296
<212> TYPE: PRT
<213> ORGANISM: Streptomyces coelicolor

<400> SEQUENCE: 33

```
Asp Tyr Gly Leu Leu Cys Ala Tyr Thr His Pro Asp Cys Asp Gly Pro
1               5                   10                  15

Ala Leu Ser Leu Ile Thr Asp Trp Tyr Val Trp Phe Phe Asp
            20                  25                  30

Asp His Phe Leu Glu Lys Tyr Lys Arg Ser Gln Asp Arg Leu Ala Gly
            35                  40                  45

Lys Ala His Leu Asp Arg Leu Pro Leu Phe Met Pro Leu Asp Asp Ala
50                  55                  60

Ala Gly Met Pro Glu Pro Arg Asn Pro Val Glu Ala Gly Leu Ala Asp
65                  70                  75                  80

Leu Trp Thr Arg Thr Val Pro Ala Met Ser Ala Asp Trp Arg Arg
                85                  90                  95

Phe Ala Val Ala Thr Glu His Leu Leu Asn Glu Ser Met Trp Glu Leu
            100                 105                 110

Ser Asn Ile Asn Glu Gly Arg Val Ala Asn Pro Val Glu Tyr Ile Glu
            115                 120                 125

Met Arg Arg Lys Val Gly Gly Ala Pro Trp Ser Ala Gly Leu Val Glu
            130                 135                 140

Tyr Ala Thr Ala Glu Val Pro Ala Ala Val Ala Gly Thr Arg Pro Leu
145                 150                 155                 160

Arg Val Leu Met Glu Thr Phe Ser Asp Ala Val His Leu Arg Asn Asp
                165                 170                 175

Leu Phe Ser Tyr Gln Arg Glu Val Glu Asp Gly Glu Leu Ser Asn
            180                 185                 190

Gly Val Leu Val Leu Glu Thr Phe Phe Gly Cys Thr Thr Gln Glu Ala
            195                 200                 205

Ala Asp Leu Val Asn Asp Val Leu Thr Ser Arg Leu His Gln Phe Glu
            210                 215                 220

His Thr Ala Phe Thr Glu Val Pro Ala Val Ala Leu Glu Lys Gly Leu
225                 230                 235                 240

Thr Pro Leu Glu Val Ala Ala Val Gly Ala Tyr Thr Lys Gly Leu Gln
                245                 250                 255

Asp Trp Gln Ser Gly Gly His Glu Trp His Met Arg Ser Arg Tyr
            260                 265                 270
```

```
Met Asn Lys Gly Glu Arg Pro Leu Ala Gly Trp Gln Ala Leu Thr Gly
        275                 280                 285

Pro Gly Thr Ser Ala Ala Asp Val
        290                 295

<210> SEQ ID NO 34
<211> LENGTH: 296
<212> TYPE: PRT
<213> ORGANISM: Streptomyces avermitilis

<400> SEQUENCE: 34

Asp Tyr Gly Leu Leu Cys Ala Tyr Thr His Pro Asp Cys Asp Gly Pro
  1               5                  10                  15

Ala Leu Ser Leu Ile Thr Asp Trp Tyr Val Trp Val Phe Phe Phe Asp
             20                  25                  30

Asp His Phe Leu Glu Thr Phe Lys Arg Thr Gln Asp Arg Glu Gly Gly
         35                  40                  45

Lys Ala Tyr Leu Asp Arg Leu Pro Leu Phe Met Pro Leu Asp Leu Ser
     50                  55                  60

Ala Pro Val Pro Glu Pro Glu Asn Pro Val Glu Ala Gly Leu Ala Asp
 65                  70                  75                  80

Leu Trp Ala Arg Thr Val Pro Ala Met Ser Ala Asp Trp Arg Lys Arg
             85                  90                  95

Phe Ala Val Ser Thr Glu His Leu Leu Asn Gly Ser Leu Trp Glu Leu
        100                 105                 110

Ser Asn Ile Asn Glu Gly Arg Ile Ala Asn Pro Val Glu Tyr Ile Glu
        115                 120                 125

Met Arg Arg Lys Val Gly Gly Ala Pro Trp Ser Ala Gly Leu Val Glu
130                 135                 140

Tyr Ala Thr Ala Glu Val Pro Ala Ala Val Ala Gly Ser Arg Pro Leu
145                 150                 155                 160

Arg Val Leu Met Glu Thr Phe Ser Asp Gly Val His Leu Arg Asn Asp
                165                 170                 175

Leu Phe Ser Tyr Gln Arg Glu Val Glu Glu Gly Glu Leu Ser Asn
            180                 185                 190

Gly Val Leu Val Leu Glu Thr Phe Phe Gly Cys Thr Thr Gln Glu Ala
        195                 200                 205

Ala Glu Thr Val Asn Asp Ile Leu Thr Ser Arg Leu His Gln Phe Glu
        210                 215                 220

His Thr Ala Leu Thr Glu Val Pro Ala Leu Ala Leu Glu Lys Gly Leu
225                 230                 235                 240

Thr Pro Pro Glu Val Ala Ala Val Ala Ala Tyr Ala Arg Gly Leu Gln
                245                 250                 255

Asp Trp Gln Ser Gly Gly His Glu Trp His Leu Arg Ser Ser Arg Tyr
            260                 265                 270

Met Asn Glu Gly Ala Leu Ser Gln Lys Arg Pro Phe Gly Leu Ser Ala
        275                 280                 285

Ile Gly Thr Ser Ala Ala Asp Leu
        290                 295

<210> SEQ ID NO 35
<211> LENGTH: 7
<212> TYPE: PRT
<213> ORGANISM: Streptomyces coelicolor

<400> SEQUENCE: 35

Asp Asp Cys Tyr Cys Glu Asp
  1               5
```

<210> SEQ ID NO 36
<211> LENGTH: 5
<212> TYPE: PRT
<213> ORGANISM: Streptomyces coelicolor
<220> FEATURE:
<221> NAME/KEY: VARIANT
<222> LOCATION: 2, 4
<223> OTHER INFORMATION: Xaa = any amino acid

<400> SEQUENCE: 36

Gly Xaa Gly Xaa Gly
 1               5

<210> SEQ ID NO 37
<211> LENGTH: 6
<212> TYPE: PRT
<213> ORGANISM: Unknown
<220> FEATURE:
<223> OTHER INFORMATION: Magnesium binding motif

<400> SEQUENCE: 37

Asp Asp His Phe Leu Glu
 1               5

<210> SEQ ID NO 38
<211> LENGTH: 9
<212> TYPE: PRT
<213> ORGANISM: Unknown
<220> FEATURE:
<223> OTHER INFORMATION: Aspartate - rich motif
<220> FEATURE:
<221> NAME/KEY: VARIANT
<222> LOCATION: 3
<223> OTHER INFORMATION: Xaa = Leu or Ile
<220> FEATURE:
<221> NAME/KEY: VARIANT
<222> LOCATION: 7
<223> OTHER INFORMATION: Xaa = Gln or Glu

<400> SEQUENCE: 38

Asn Asp Xaa Phe Ser Tyr Xaa Arg Glu
 1               5

<210> SEQ ID NO 39
<211> LENGTH: 5
<212> TYPE: PRT
<213> ORGANISM: Unknown
<220> FEATURE:
<223> OTHER INFORMATION: Aspartate - rich motif
<220> FEATURE:
<221> NAME/KEY: VARIANT
<222> LOCATION: 3, 4
<223> OTHER INFORMATION: Xaa = any amino acid

<400> SEQUENCE: 39

Asp Asp Xaa Xaa Asp
 1               5

<210> SEQ ID NO 40
<211> LENGTH: 9
<212> TYPE: PRT
<213> ORGANISM: Unknown
<220> FEATURE:
<223> OTHER INFORMATION: NSE triad motif
<220> FEATURE:
<221> NAME/KEY: VARIANT
<222> LOCATION: 1
<223> OTHER INFORMATION: Xaa = Asn or Asp
<220> FEATURE:

-continued

```
<221> NAME/KEY: VARIANT
<222> LOCATION: (3)...(4)
<223> OTHER INFORMATION: Xaa = any amino acid
<220> FEATURE:
<221> NAME/KEY: VARIANT
<222> LOCATION: 5
<223> OTHER INFORMATION: Xaa = Ser or Thr
<220> FEATURE:
<221> NAME/KEY: VARIANT
<222> LOCATION: (6)...(8)
<223> OTHER INFORMATION: Xaa = any amino acid

<400> SEQUENCE: 40

Xaa Asp Xaa Xaa Xaa Xaa Xaa Xaa Glu
 1               5

<210> SEQ ID NO 41
<211> LENGTH: 5
<212> TYPE: PRT
<213> ORGANISM: Unknown
<220> FEATURE:
<223> OTHER INFORMATION: Aspartate - rich motif

<400> SEQUENCE: 41

Asp Asp Tyr Tyr Pro
 1               5

<210> SEQ ID NO 42
<211> LENGTH: 9
<212> TYPE: PRT
<213> ORGANISM: Unknown
<220> FEATURE:
<223> OTHER INFORMATION: NSE triad motif
<220> FEATURE:
<221> NAME/KEY: VARIANT
<222> LOCATION: 3
<223> OTHER INFORMATION: Xaa = Val, Ile or Leu

<400> SEQUENCE: 42

Asn Asp Xaa Phe Ser Tyr Gln Lys Glu
 1               5

<210> SEQ ID NO 43
<211> LENGTH: 763
<212> TYPE: PRT
<213> ORGANISM: Saccharopolyspora erythraea

<400> SEQUENCE: 43

Met Gln Pro Phe Arg Leu Pro Glu Phe Tyr Val Pro Trp Pro Ala Arg
 1               5                  10                  15

Leu Asn Pro His Leu Glu Thr Ala Arg Glu His Ser Lys Ala Trp Ala
                20                  25                  30

Arg Glu Met Gly Met Leu Pro Gly Gly Pro Leu Gly Asp Asp Gln Ala
            35                  40                  45

Val Trp Asp Glu Ala Thr Phe Asp Ala His Asp Tyr Ala Leu Leu Cys
        50                  55                  60

Ala Tyr Thr His Pro Asp Ala Thr Ala His Glu Leu Gly Leu Val Thr
    65                  70                  75                  80

Asp Trp Tyr Val Trp Val Phe Tyr Phe Asp His Phe Leu Glu Tyr
                    85                  90                  95

Tyr Lys Arg Thr Arg Asp Leu Thr Gly Ala Arg Glu Tyr Leu Ala Gly
                100                 105                 110

Leu Ala Ala Phe Met Pro Ala Glu Leu Thr Glu Gln Pro Thr Ala
            115                 120                 125

Lys Asn Pro Val Glu Trp Gly Leu Val Asp Leu Trp Ala Arg Ser Val
```

-continued

```
                130                 135                 140
Pro Ile Met Ser Ala Asp Trp Leu Arg Arg Phe Ser Glu Ser Thr Arg
145                 150                 155                 160

Asn Leu Leu Glu Asp Cys Val Trp Glu Leu Thr Asn Ile Thr His Gly
                165                 170                 175

Gln Val Pro Asn Pro Ile Asp Tyr Val Glu Met Arg Arg Arg Val Gly
                180                 185                 190

Gly Ala Pro Trp Ser Ala Asp Leu Val Glu Leu Ala Ala Arg Val Glu
                195                 200                 205

Val Pro Ala Gln Ile Ala Arg Thr Arg Pro Met Ser Val Leu Lys Asp
210                 215                 220

Thr Phe Ala Asp Ala Val His Leu Arg Asn Asp Ile Phe Ser Tyr Gln
225                 230                 235                 240

Arg Glu Thr Glu Glu Gly Glu Leu Asn Asn Gly Val Leu Val Phe
                245                 250                 255

Glu Arg Phe Leu Asp Cys Gly Pro Gln Glu Ala Ala Asp Thr Thr Asn
                260                 265                 270

Glu Leu Leu Thr Ser Arg Leu Gln Gln Phe Glu Asn Thr Ala Leu Thr
                275                 280                 285

Glu Val Pro Pro Leu Cys Glu Glu Tyr Gly Leu Asp Pro Ala Glu Arg
                290                 295                 300

Ala Ala Val Leu Thr Tyr Val Lys Gly Leu Gln Asp Trp Gln Ser Gly
305                 310                 315                 320

Gly His Glu Trp His Leu Arg Ser Ser Arg Tyr Met Asn Asp Gly Ala
                325                 330                 335

Leu Ala Gly Ala Arg Ser Pro Phe Gly Gly Pro Thr Gly Leu Gly Thr
                340                 345                 350

Ser Ala Ala His Asn Ala Leu Ala Arg Val Arg Pro Gly Ile Arg Arg
                355                 360                 365

His Arg Glu Gln His Ser His Ala Pro Phe Ala Pro Val Gly His Leu
                370                 375                 380

Pro Leu Pro Glu Ile Tyr Met Pro Phe Pro Val Arg Met Ser Pro His
385                 390                 395                 400

Leu Asp Ala Ala Arg Gln His Ala Val Asp Trp Ala Arg Glu Met Gly
                405                 410                 415

Met Phe Asp Ser Val Pro Gly Ser Glu Val Gly Val Trp Asn Glu
                420                 425                 430

Arg Arg Phe Val Gly Phe Asp Phe Pro His Cys Ala Ala Met Ile His
                435                 440                 445

Ala Asp Ala Gly Pro Glu Gln Leu Asp Leu Ser Ser Asp Trp Leu Ala
450                 455                 460

Trp Gly Thr Tyr Gly Asp Asp Phe Pro Val Val Phe Gly Ala Thr
465                 470                 475                 480

Arg Asn Leu Ala Ala Ala Lys Val Cys Asn Asp Arg Leu Ser Ala Phe
                485                 490                 495

Met Pro Ile Asp Gly Gly Val Pro Glu Pro Ala Asn Val Leu Glu
                500                 505                 510

Arg Gly Leu Ala Asp Leu Trp Arg Arg Thr Ala Gly Pro Met Pro Ala
                515                 520                 525

Asp Ser Arg Arg Gln Phe Arg Lys Ala Val Glu Asp Met Thr Ser Ser
                530                 535                 540

Trp Leu Trp Glu Leu Ala Asn Gln Thr Gln Asn Arg Ile Pro Asp Pro
545                 550                 555                 560
```

```
                Val Asp Tyr Ile Glu Met Arg Arg Thr Phe Gly Ser Asp Met Thr
                                565                 570                 575

Met Ser Leu Ser Arg Leu Ala Asn Ala Val Val Pro Ala Glu Ile
                            580                 585                 590

Tyr Arg Thr Arg Val Met Arg Glu Leu Glu Trp Ser Ala Gln Asp Tyr
                        595                 600                 605

Ala Cys Phe Thr Asn Asp Leu Phe Ser Tyr Gln Lys Glu Ile Glu Phe
                        610                 615                 620

Glu Gly Glu Val His Asn Met Val Leu Val Val Glu Asn Phe Leu Gly
                625                 630                 635                 640

Val Asp Arg Leu Thr Ala Arg Asp Val Val Ala Asp Leu Met Lys Ala
                                645                 650                 655

Arg Met Arg Gln Phe Glu Arg Ile Leu Ala Glu Glu Leu Pro Thr Leu
                            660                 665                 670

Ile Asp Glu Phe Glu Leu Asp Glu Ala Ala Arg Thr Ala Leu Thr Arg
                        675                 680                 685

Gln Cys Asp Glu Leu Lys Asp Trp Thr Ser Gly Ile Leu Glu Trp His
                        690                 695                 700

Arg Arg Cys Val Arg Tyr Thr Asp Ala Glu Leu Arg Arg Thr Arg Ser
                705                 710                 715                 720

Glu His His His Gly Thr Gly Pro Glu Pro His Leu Pro Leu Arg Arg
                                725                 730                 735

Arg Leu Ser Gly Pro Thr Gly Ile Gly Thr Ser Ala Ala Arg Leu Ala
                            740                 745                 750

Arg Arg Gly Ser Ser Ala Thr Gly Leu Asn Arg
                        755                 760

<210> SEQ ID NO 44
<211> LENGTH: 9
<212> TYPE: PRT
<213> ORGANISM: Notstoc punctiforme

<400> SEQUENCE: 44

Asn Asp Leu Phe Ser Tyr Gln Arg Glu
 1               5

<210> SEQ ID NO 45
<211> LENGTH: 5
<212> TYPE: PRT
<213> ORGANISM: Notstoc punctiforme

<400> SEQUENCE: 45

Asp Asp Tyr Phe Pro
 1               5

<210> SEQ ID NO 46
<211> LENGTH: 25
<212> TYPE: DNA
<213> ORGANISM: Unknown
<220> FEATURE:
<223> OTHER INFORMATION: Degenerate oligonucleotide primer

<400> SEQUENCE: 46
cgaccatcgt caacgacctc tactc                                        25

<210> SEQ ID NO 47
<211> LENGTH: 20
<212> TYPE: DNA
<213> ORGANISM: Unknown
<220> FEATURE:
<223> OTHER INFORMATION: Degenerate oligonucleotide primer
```

```
<400> SEQUENCE: 47
cggctgatgg tcgcggagaa                                              20

<210> SEQ ID NO 48
<211> LENGTH: 20
<212> TYPE: DNA
<213> ORGANISM: Unknown
<220> FEATURE:
<223> OTHER INFORMATION: Degenerate oligonucleotide primer

<400> SEQUENCE: 48
cgactvatgg tsgcwgagaa                                              20

<210> SEQ ID NO 49
<211> LENGTH: 20
<212> TYPE: DNA
<213> ORGANISM: Unknown
<220> FEATURE:
<223> OTHER INFORMATION: Degenerate oligonucleotide primer

<400> SEQUENCE: 49
tgcggtgcca gtcgtggttg                                              20

<210> SEQ ID NO 50
<211> LENGTH: 20
<212> TYPE: DNA
<213> ORGANISM: Unknown
<220> FEATURE:
<223> OTHER INFORMATION: Degenerate oligonucleotide primer

<400> SEQUENCE: 50
ttcgrtgcca rtcrtggttg                                              20

<210> SEQ ID NO 51
<211> LENGTH: 19
<212> TYPE: DNA
<213> ORGANISM: Unknown
<220> FEATURE:
<223> OTHER INFORMATION: Degenerate oligonucleotide primer

<400> SEQUENCE: 51
ttcgacggct tctcggtgg                                               19

<210> SEQ ID NO 52
<211> LENGTH: 20
<212> TYPE: DNA
<213> ORGANISM: Unknown
<220> FEATURE:
<223> OTHER INFORMATION: Degenerate oligonucleotide primer

<400> SEQUENCE: 52
ttygayggyt tcttwgtggg                                              20

<210> SEQ ID NO 53
<211> LENGTH: 25
<212> TYPE: DNA
<213> ORGANISM: Unknown
<220> FEATURE:
<223> OTHER INFORMATION: Degenerate oligonucleotide primer

<400> SEQUENCE: 53
gtggacgact gctactgcga ggacc                                        25

<210> SEQ ID NO 54
<211> LENGTH: 25
```

```
<212> TYPE: DNA
<213> ORGANISM: Unknown
<220> FEATURE:
<223> OTHER INFORMATION: Degenerate oligonucleotide primer

<400> SEQUENCE: 54
gtsgaygayt gytartgyga agatc                                         25

<210> SEQ ID NO 55
<211> LENGTH: 25
<212> TYPE: DNA
<213> ORGANISM: Unknown
<220> FEATURE:
<223> OTHER INFORMATION: Degenerate oligonucleotide primer

<400> SEQUENCE: 55
gagttccttg gtgtaggagt agagg                                         25

<210> SEQ ID NO 56
<211> LENGTH: 24
<212> TYPE: DNA
<213> ORGANISM: Unknown
<220> FEATURE:
<223> OTHER INFORMATION: Degenerate oligonucleotide primer

<400> SEQUENCE: 56
bagwtctttg tktawaasta gagg                                          24

<210> SEQ ID NO 57
<211> LENGTH: 22
<212> TYPE: DNA
<213> ORGANISM: Unknown
<220> FEATURE:
<223> OTHER INFORMATION: Degenerate oligonucleotide primer

<400> SEQUENCE: 57
ggcaggctgt agcggtaggt gt                                            22

<210> SEQ ID NO 58
<211> LENGTH: 22
<212> TYPE: DNA
<213> ORGANISM: Unknown
<220> FEATURE:
<223> OTHER INFORMATION: Degenerate oligonucleotide primer

<400> SEQUENCE: 58
ggbagwctkt atcgvtaggt gt                                            22

<210> SEQ ID NO 59
<211> LENGTH: 19
<212> TYPE: DNA
<213> ORGANISM: Unknown
<220> FEATURE:
<223> OTHER INFORMATION: Degenerate oligonucleotide primer

<400> SEQUENCE: 59
gagggagtga ccctgtccg                                                19

<210> SEQ ID NO 60
<211> LENGTH: 19
<212> TYPE: DNA
<213> ORGANISM: Unknown
<220> FEATURE:
<223> OTHER INFORMATION: Degenerate oligonucleotide primer

<400> SEQUENCE: 60
gaaggtgtca ctctbtccg                                                19
```

<210> SEQ ID NO 61
<211> LENGTH: 19
<212> TYPE: DNA
<213> ORGANISM: Unknown
<220> FEATURE:
<223> OTHER INFORMATION: Degenerate oligonucleotide primer

<400> SEQUENCE: 61
gaagtgggcg ttgatctgg                                            19

<210> SEQ ID NO 62
<211> LENGTH: 19
<212> TYPE: DNA
<213> ORGANISM: Unknown
<220> FEATURE:
<223> OTHER INFORMATION: Degenerate oligonucleotide primer

<400> SEQUENCE: 62
aaartgwgcr tttatctgg                                            19

<210> SEQ ID NO 63
<211> LENGTH: 25
<212> TYPE: DNA
<213> ORGANISM: Unknown
<220> FEATURE:
<223> OTHER INFORMATION: Degenerate oligonucleotide primer
<220> FEATURE:
<221> NAME/KEY: misc_feature
<222> LOCATION: 11, 14
<223> OTHER INFORMATION: n = a, t, c or g

<400> SEQUENCE: 63
tcaccatwaa nccncctcga gggca                                     25

<210> SEQ ID NO 64
<211> LENGTH: 17
<212> TYPE: DNA
<213> ORGANISM: Unknown
<220> FEATURE:
<223> OTHER INFORMATION: Degenerate oligonucleotide primer

<400> SEQUENCE: 64
gacgccgtac caggagg                                              17

<210> SEQ ID NO 65
<211> LENGTH: 17
<212> TYPE: DNA
<213> ORGANISM: Unknown
<220> FEATURE:
<223> OTHER INFORMATION: Degenerate oligonucleotide primer

<400> SEQUENCE: 65
gactccgtay caygagg                                              17

<210> SEQ ID NO 66
<211> LENGTH: 17
<212> TYPE: DNA
<213> ORGANISM: Unknown
<220> FEATURE:
<223> OTHER INFORMATION: Degenerate oligonucleotide primer

<400> SEQUENCE: 66
ccgggagtgg atgttgc                                              17

<210> SEQ ID NO 67
<211> LENGTH: 17

```
<212> TYPE: DNA
<213> ORGANISM: Unknown
<220> FEATURE:
<223> OTHER INFORMATION: Degenerate oligonucleotide primer
<220> FEATURE:
<221> NAME/KEY: misc_feature
<222> LOCATION: 4
<223> OTHER INFORMATION: n = a, t, c or g

<400> SEQUENCE: 67
yccngartgr atgttgc                                                17

<210> SEQ ID NO 68
<211> LENGTH: 25
<212> TYPE: DNA
<213> ORGANISM: Unknown
<220> FEATURE:
<223> OTHER INFORMATION: Degenerate oligonucleotide primer

<400> SEQUENCE: 68
atcaggacgt actggaagga gccgt                                       25

<210> SEQ ID NO 69
<211> LENGTH: 25
<212> TYPE: DNA
<213> ORGANISM: Unknown
<220> FEATURE:
<223> OTHER INFORMATION: Degenerate oligonucleotide primer

<400> SEQUENCE: 69
tgaccatgga accgccgcgt ccgca                                       25

<210> SEQ ID NO 70
<211> LENGTH: 39
<212> TYPE: DNA
<213> ORGANISM: Unknown
<220> FEATURE:
<223> OTHER INFORMATION: Degenerate oligonucleotide primer

<400> SEQUENCE: 70
attttatcca tggttatgca acccttgaa ctgccagaa                         39

<210> SEQ ID NO 71
<211> LENGTH: 30
<212> TYPE: DNA
<213> ORGANISM: Unknown
<220> FEATURE:
<223> OTHER INFORMATION: oligonucleotide primer

<400> SEQUENCE: 71
taataactcg agttatggat ttcgccctcg                                  30

<210> SEQ ID NO 72
<211> LENGTH: 31
<212> TYPE: DNA
<213> ORGANISM: Unknown
<220> FEATURE:
<223> OTHER INFORMATION: oligonucleotide primer

<400> SEQUENCE: 72
taataactcg agtaattgac cgagtaatga c                                31

<210> SEQ ID NO 73
<211> LENGTH: 27
<212> TYPE: DNA
<213> ORGANISM: Unknown
<220> FEATURE:
<223> OTHER INFORMATION: oligonucleotide primer
```

```
<400> SEQUENCE: 73
ttactcggtc aatgattact cgagcac                                          27

<210> SEQ ID NO 74
<211> LENGTH: 27
<212> TYPE: DNA
<213> ORGANISM: Unknown
<220> FEATURE:
<223> OTHER INFORMATION: Oligonucleotide primer

<400> SEQUENCE: 74
gtgctcgagt aatcattgac cgagtaa                                          27

<210> SEQ ID NO 75
<211> LENGTH: 9
<212> TYPE: PRT
<213> ORGANISM: Unknown
<220> FEATURE:
<223> OTHER INFORMATION: Conserved Mg2+ -binding motif

<400> SEQUENCE: 75

Asn Asp Val Phe Ser Tyr Gln Lys Glu
 1               5

<210> SEQ ID NO 76
<211> LENGTH: 9
<212> TYPE: PRT
<213> ORGANISM: Unknown
<220> FEATURE:
<223> OTHER INFORMATION: Conserved Mg2+ -binding motif

<400> SEQUENCE: 76

Asn Asp Leu Phe Ser Tyr Glu Arg Glu
 1               5

<210> SEQ ID NO 77
<211> LENGTH: 12
<212> TYPE: PRT
<213> ORGANISM: Unknown
<220> FEATURE:
<223> OTHER INFORMATION: Conserved Mg2+ -binding motif

<400> SEQUENCE: 77

Asn Glu Val Leu Thr Ser Arg Leu Gln Gln Phe Glu
 1               5                  10

<210> SEQ ID NO 78
<211> LENGTH: 734
<212> TYPE: PRT
<213> ORGANISM: Streptomyces scabies

<400> SEQUENCE: 78

Met Thr Gln Pro Phe Ala Leu Pro His Phe Tyr Leu Pro Tyr Pro Ala
 1               5                  10                  15

Arg Leu Asn Pro His Leu Glu Glu Ala Arg Ala His Ser Ser Val Trp
                20                  25                  30

Ala Arg Glu Met Gly Met Leu Glu Gly Ser Gly Val Trp Asn Gln Ala
            35                  40                  45

Asp Leu Asp Ala His Asp Tyr Gly Leu Leu Cys Ala Tyr Thr His Pro
        50                  55                  60

Asp Cys Asp Gly Pro Ala Leu Ser Leu Ile Thr Asp Trp Tyr Val Trp
    65                  70                  75                  80

Val Phe Phe Phe Asp Asp His Phe Leu Glu Leu Tyr Lys Arg Ser Gln
```

-continued

```
                85                  90                  95
Asp Arg Pro Gly Gly Lys Ala His Leu Asp Arg Leu Pro Leu Phe Met
            100                 105                 110
Pro Leu Asp Leu Ser Thr Pro Val Pro Glu Pro Arg Asn Pro Val Glu
            115                 120                 125
Ala Gly Leu Ala Asp Leu Trp Ala Arg Thr Val Pro Ser Met Ser Met
            130                 135                 140
Asp Trp Arg Arg Arg Phe Ala Val Ala Thr Glu His Leu Leu Asn Glu
145                 150                 155                 160
Ser Met Trp Glu Leu Ser Asn Ile Asn Glu Gly Arg Ile Ala Asn Pro
                165                 170                 175
Val Glu Tyr Ile Glu Met Arg Arg Lys Val Gly Gly Ala Pro Trp Ser
            180                 185                 190
Ala Gly Leu Val Glu Tyr Ala Thr Ala Glu Val Pro Glu Ser Val Ala
            195                 200                 205
Asp Thr Arg Pro Leu Arg Val Leu Met Glu Thr Phe Ser Asp Ala Val
            210                 215                 220
His Leu Arg Asn Asp Leu Phe Ser Tyr Gln Arg Glu Val Glu Glu Glu
225                 230                 235                 240
Gly Glu Asn Ser Asn Gly Val Leu Val Leu Glu Thr Phe Phe Gly Cys
                245                 250                 255
Gly Thr Gln Gln Ala Ala Glu Thr Val Asn Asp Ile Leu Thr Ser Arg
            260                 265                 270
Leu His Gln Phe Glu Asp Thr Ala Leu Thr Glu Val Pro Ala Ile Ala
            275                 280                 285
Val Glu Lys Gly Leu Thr Pro Gly Glu Val Ala Ala Val Ala Ala Tyr
            290                 295                 300
Thr Lys Gly Leu Gln Asp Trp Gln Ser Gly Gly His Glu Trp His Met
305                 310                 315                 320
Arg Ser Ser Arg Tyr Met Asn Glu Gly Ala Thr Ser Ala Arg Gly Pro
                325                 330                 335
Leu Asp Leu Gly Gly Ala Val Leu Ser Gly Pro Ala Leu Val Thr Arg
            340                 345                 350
Ala Gly His Gly Thr Ser Ala Ala Asp Val Gly Ala Leu Leu Ala Thr
            355                 360                 365
Ala Ala Ala Gln Arg Leu Arg Ala His Thr His Gln Pro Tyr Gln Lys
            370                 375                 380
Val Gly Pro Ser Leu Leu Pro Asp Phe His Met Pro Phe Arg Val Ala
385                 390                 395                 400
Leu Cys Pro His Leu Asp Gly Ala Arg Pro Arg Leu Thr Ala Trp Ala
                405                 410                 415
His Ala Met Gly Ile Leu Ser Glu Gly Val Trp Asp Glu Glu Arg Leu
            420                 425                 430
Ala Ala Ala Asp Leu Pro Leu Cys Ser Ala Gly Leu Asp Pro Asp Ala
            435                 440                 445
Thr Pro Glu Gln Leu Asp Leu Ser Ser Ala Trp Leu Ala Trp Gly Thr
            450                 455                 460
Tyr Gly Asp Asp Tyr Tyr Pro Leu Val Phe Gly His Arg Arg Asp Leu
465                 470                 475                 480
Ala Ala Ala Arg Leu Thr Thr Ala Arg Leu Ser Asp Cys Met Pro Leu
                485                 490                 495
Asp Gly Glu Arg Ala Pro Leu Pro Ser Asn Ala Met Glu Arg Ala Leu
            500                 505                 510
```

-continued

```
Val Asp Leu Trp Thr Arg Thr Thr Ala Ala Met Thr Pro Asp Glu Arg
            515                 520                 525

Arg Gly Leu Lys Glu Ser Val Asp Lys Met Thr Glu Ser Trp Val Trp
        530                 535                 540

Glu Val Phe Asn Gln Ile His His Arg Val Pro Asp Pro Val Asp Tyr
545                 550                 555                 560

Leu Glu Met Arg Arg Ala Thr Phe Gly Ser Asp Leu Thr Leu Ser Met
                565                 570                 575

Cys Arg Met Gly His Gly Pro Gln Ile Pro Pro Glu Val Tyr Arg Ser
                580                 585                 590

Gly Pro Val Arg Ser Leu Glu Asn Ala Ala Ile Asp Tyr Gly Cys Leu
            595                 600                 605

Ile Asn Asp Val Phe Ser Tyr Gln Lys Glu Ile Glu Tyr Glu Gly Glu
610                 615                 620

Val His Asn Ala Ile Leu Val Val Gln Asn Phe Phe Gly Cys Asp Tyr
625                 630                 635                 640

Pro Ala Ala Leu Gly Val Val His Asp Leu Met Thr Gln Arg Met Arg
                645                 650                 655

Gln Phe Glu His Val Val Ala His Glu Leu Pro Val Val Tyr Asp Asp
                660                 665                 670

Phe Arg Leu Ser Arg Glu Ala Arg Asp Ile Met Gly Gly Tyr Val Thr
            675                 680                 685

Asp Leu Gln Asn Trp Met Ala Gly Ile Leu Asn Trp His Arg Asn Val
690                 695                 700

Asp Arg Tyr Lys Pro Glu Phe Leu Ala Arg Arg Ala His Asn Phe Val
705                 710                 715                 720

Pro Asp Arg Pro Pro Thr Leu Ser Leu Thr Pro Leu Arg Thr
                725                 730

<210> SEQ ID NO 79
<211> LENGTH: 732
<212> TYPE: PRT
<213> ORGANISM: Streptomyces peucetius

<400> SEQUENCE: 79

Met Ala Gln Pro Phe Val Leu Pro Asp Phe Tyr Val Pro Tyr Pro Ala
1               5                   10                  15

Arg Leu Asn Arg His Val Glu Glu Ala Arg Arg His Ser Lys Lys Trp
            20                  25                  30

Ala Arg Arg Met Gly Met Leu Glu Gly Ser Gly Ile Trp Glu Glu Ser
        35                  40                  45

Asp Leu Asp Ala His Asp Tyr Ala Leu Leu Cys Ala Tyr Thr His Pro
    50                  55                  60

Asp Cys Asp Ala Asp Ala Leu Gly Leu Val Thr Asp Trp Tyr Val Trp
65                  70                  75                  80

Val Phe Phe Phe Asp Asp His Phe Leu Glu Val Phe Lys Arg Ser Gln
                85                  90                  95

Asp Leu Ala Gly Gly Lys Ala Tyr Leu Asp Arg Leu Pro Ala Phe Met
            100                 105                 110

Pro Met Asp Leu Ser Arg Gly Thr Pro Glu Pro Arg Asn Pro Val Glu
        115                 120                 125

Ala Gly Leu Ala Asp Leu Trp Gln Arg Thr Val Pro Ser Met Ser Pro
    130                 135                 140

Ala Trp Arg Thr Arg Phe Ala Glu Ala Thr Glu His Leu Leu Asn Glu
145                 150                 155                 160
```

-continued

```
Ser Met Trp Glu Leu Thr Asn Ile Asp Ala Gly Arg Val Ala Asn Pro
            165                 170                 175

Val Glu Tyr Ile Glu Met Arg Arg Lys Val Gly Gly Ala Pro Trp Ser
            180                 185                 190

Ala Gly Leu Val Glu Tyr Ala Ala Gln Ala Glu Val Pro Glu Ser Val
            195                 200                 205

Ala Gly Ala Arg Pro Leu Arg Val Leu Arg Asp Ser Phe Ser Asp Ala
            210                 215                 220

Val His Leu Arg Asn Asp Leu Phe Ser Tyr Gln Arg Glu Val Glu Asp
225                 230                 235                 240

Glu Gly Glu Asn Ser Asn Gly Val Leu Val Leu Glu Arg Phe Leu Gly
            245                 250                 255

Cys Gly Thr Gln Glu Ala Ala Glu Val Val Asn Asp Leu Leu Thr Ser
            260                 265                 270

Arg Val Gln Gln Phe Glu Asn Thr Ala Leu Thr Glu Val Pro Ala Leu
            275                 280                 285

Cys Val Gln Lys Gly Leu Ala Pro Ala Glu Cys Ala Ala Ile Ala Ala
            290                 295                 300

Tyr Thr Lys Gly Leu Gln Asp Trp Gln Ser Gly Gly His Glu Trp His
305                 310                 315                 320

Met Arg Ser Ser Arg Tyr Met Asn Glu Gly Val Glu Thr Glu Arg Ser
            325                 330                 335

Arg Phe Glu Gly Val Leu Ala Thr Ser Ala Leu Asp Ile Arg Thr Leu
            340                 345                 350

Phe Gly Arg Pro Ala Ala Ala Arg Met Arg Thr Leu Thr His Arg Pro
            355                 360                 365

Gln Gln Val Gly Pro Ser Trp Leu Pro Asp Phe Asp Leu Pro Phe Pro
            370                 375                 380

Leu Ser Leu Ser Pro His Leu Glu Gln Ala Arg Ala Ala Ser Val Ala
385                 390                 395                 400

Trp Ala Gly Arg Met Gly Leu Leu Gly Asp Ile Trp Asp Glu Ala Lys
            405                 410                 415

Leu Thr Gly Phe Asp Phe Ala Leu Cys Ser Ala Gly Leu Asp Pro Asp
            420                 425                 430

Ala Thr Pro Glu Glu Leu Glu Leu Ser Ala Glu Trp Leu Thr Trp Gly
            435                 440                 445

Thr Tyr Gly Asp Asp Tyr Tyr Pro Leu Val Phe Gly Arg Ala Arg Ala
450                 455                 460

Leu Glu Gly Ala Arg Leu Cys Asn Glu Arg Leu Lys Ala Cys Met Pro
465                 470                 475                 480

Val Asp Glu Pro Ala Gly Ala Ala Val Ala Val Ala Pro Met Glu
            485                 490                 495

Arg Ser Leu Ala Asp Leu Trp Ala Arg Thr Ala Gly Pro Met Ser Pro
            500                 505                 510

Gly Ala Arg Ser Ser Leu Arg Ser Ala Ile Asp Val Met Leu Asp Ser
            515                 520                 525

Trp Leu Trp Glu Leu His Asn Gln Ala Gln His Arg Val Pro Asp Pro
            530                 535                 540

Val Asp Tyr Ile Glu Met Arg Arg Leu Thr Phe Gly Ser Asp Leu Thr
545                 550                 555                 560

Met Ser Leu Cys Arg Leu Arg His Glu Gly Glu Leu Pro Pro Glu Leu
            565                 570                 575

Tyr Ala Ser Gly Pro Val Arg Gly Leu Glu Asn Ala Ala Met Asp Tyr
            580                 585                 590
```

```
Ala Cys Leu Ile Asn Asp Leu Phe Ser Tyr Gln Lys Glu Ile Glu Tyr
        595             600             605

Glu Gly Glu Val His Asn Ala Val Leu Val Val Gln Thr Phe Phe Asp
        610             615             620

Cys Asp Arg Pro Thr Ala Ala Ala Met Thr Asp Ala Leu Met Arg Ser
625             630             635                         640

Arg Leu Glu Gln Phe Leu His Thr Lys Glu His Glu Leu Pro Leu Val
                645             650                     655

Cys Glu Glu Phe Gly Leu Asp Glu Gly Gly Ser Ala Ala Leu Gly Thr
            660             665             670

Tyr Val Arg Glu Leu Glu Asp Trp Leu Ala Gly Ile Leu Asn Trp His
        675             680             685

Arg Lys Val Arg Arg Tyr Lys Glu Glu Asp Leu Arg Gly Gly Ala Val
        690             695             700

Pro Arg Arg Leu Gly Ala Pro Thr Gly Leu Gly Thr Ser Ala Ala Arg
705             710             715                         720

Leu Ser Leu Pro Ser Arg Leu Ser Gly Val Gly Val
                725             730
```